United States Patent [19]
Findeis et al.

[11] Patent Number: 5,985,242
[45] Date of Patent: Nov. 16, 1999

[54] MODULATORS OF β-AMYLOID PEPTIDE AGGREGATION COMPRISING D-AMINO ACIDS

[75] Inventors: Mark A. Findeis, Cambridge; Malcolm L. Gefter, Lincoln; Gary Musso, Hopkinton; Ethan R. Signer, Cambridge; James Wakefield; Susan Molineaux, both of Brookline; Joseph Chin, Salem; Jung-Ja Lee, Wayland; Michael Kelley, Arlington; Sonja Komar-Panicucci, Bedford; Christopher C. Arico-Muendel, Watertown; Kathryn Phillips, Marlborough; Neil J. Hayward, North Grafton, all of Mass.

[73] Assignee: Praecis Pharmaceuticals, Inc., Cambridge, Mass.

[21] Appl. No.: 08/920,162

[22] Filed: Aug. 27, 1997

Related U.S. Application Data

[63] Continuation-in-part of application No. 08/548,998, Oct. 27, 1995, abandoned, application No. 08/616,081, Mar. 14, 1996, abandoned, application No. 08/703,675, Aug. 27, 1996, and application No. 08/897,342, Jul. 21, 1997, abandoned.

[51] Int. Cl.[6] .......................... A61K 38/06; A61K 38/07; A61K 38/08; C07K 7/06
[52] U.S. Cl. ....................... 424/9.1; 424/9.42; 424/9.45; 436/501; 514/17; 514/18; 530/330; 530/331
[58] Field of Search ................... 530/330, 331, 530/345; 514/17, 18; 436/501; 424/9.1, 9.42, 9.45

[56] References Cited

U.S. PATENT DOCUMENTS

| | | | |
|---|---|---|---|
| 4,119,493 | 10/1978 | Isowa et al. | 195/29 |
| 5,338,663 | 8/1994 | Potter et al. | 435/4 |
| 5,470,951 | 11/1995 | Roberts | 530/330 |
| 5,541,290 | 7/1996 | Harbeson et al. | 530/330 |
| 5,593,846 | 1/1997 | Schenk et al. | 435/7.9 |

FOREIGN PATENT DOCUMENTS

| | | |
|---|---|---|
| 554 887 | 8/1993 | European Pat. Off. |
| 641 861 | 3/1995 | European Pat. Off. |
| 681 844 | 11/1995 | European Pat. Off. |
| WO 93/04194 | 3/1993 | WIPO |
| WO 93/11772 | 6/1993 | WIPO |

(List continued on next page.)

OTHER PUBLICATIONS

Soto et al, Inhibition of Alzheimers Amyloidosis . . . Biochem. Biophys. Res. Comm. vol. 226, pp. 672–680. 1996.

(List continued on next page.)

*Primary Examiner*—Jeffrey E. Russel
*Attorney, Agent, or Firm*—Lahive & Cockfield, LLP; Amy E. Mandragouras; Guilio A. DeConti, Jr.

[57] ABSTRACT

Compounds that modulate natural β amyloid peptide aggregation are provided. The modulators of the invention comprise a peptide, preferably based on a β amyloid peptide, that is comprised entirely of D-amino acids. Preferably, the peptide comprises 3–5 D-amino acid residues and includes at least two D-amino acid residues independently selected from the group consisting of D-leucine, D-phenylalanine and D-valine. In a particularly preferred embodiment, the peptide is a retro-inverso isomer of a β amyloid peptide, preferably a retro-inverso isomer of $A\beta_{17-21}$. In certain embodiments, the peptide is modified at the amino-terminus, the carboxy-terminus, or both. Preferred amino-terminal modifying groups include cyclic, heterocyclic, polycyclic and branched alkyl groups. Preferred carboxy-terminal modifying groups include an amide group, an alkyl amide group, an aryl amide group or a hydroxy group. Pharmaceutical compositions comprising the compounds of the invention, and diagnostic and treatment methods for amyloidogenic diseases using the compounds of the invention, are also disclosed.

19 Claims, 4 Drawing Sheets

FOREIGN PATENT DOCUMENTS

| | | |
|---|---|---|
| WO 94/28412 | 12/1994 | WIPO . |
| WO 95/05394 | 2/1995 | WIPO . |
| WO 95/05604 | 2/1995 | WIPO . |
| WO 95/07093 | 3/1995 | WIPO . |
| WO 95/08999 | 4/1995 | WIPO . |
| WO 95/12815 | 5/1995 | WIPO . |
| WO 95/20979 | 8/1995 | WIPO . |
| WO 96/28471 | 9/1996 | WIPO . |
| WO 97/21728 | 6/1997 | WIPO . |
| WO 98/08868 | 3/1998 | WIPO . |

OTHER PUBLICATIONS

Tjernberg et al, Controlling Amyloid β–Peptide Fibril Formation . . . J. Biol. Chem., vol. 272, No. 19, pp. 12601–12605. May 9, 1997.

Barrow, Colin J and Michael G. Zagorski (1991) "Solution Structures of β Peptide and Its Constituent Fragments: Relation to Amyloid Deposition", Science 253: 179–182.

Barrow, Colin J. et al (1992) "Solution Conformations and Aggregational Properties of Synthetic Amyloid β–Peptides of Alzheimer's Disease: Analysis of Circular Dichroism Spectra" J. Mol. Biol. 225: 1075–1093.

Brown, Abraham M et al. (1994) "Biotinylated and Cysteine–Modified Peptides as Useful Reagents for Studying the Inhibition of Cathepsin G" Analytical Biochemistry 217: 139–147.

Burdick, Debra et al. (1992) "Assembly and Aggregation Properties of Synthetic Alzheimer's A4/ β Amyloid Peptide Analogs" Journal of Biological Chemistry 267(1): 546–554.

Chantry, Andrew et al. (1992) "Biotinyl Analogues of Amylin as Biologically Active Probes for Amylin/CGRP Receptor Recognition" FEBS 296(2): 123–127.

Clements, Angela et al. (1993) "Aggregation of Alzheimer's Peptides" Biochemical Society Transactions 22: 16S.

Clemens J.A.et al. (1992) "Implants Containing β–Amyloid Protein Are Not Neurotoxic to Young and Old Rat Brain" Neurobiology of Aging 13: 581–586.

Come, Jon H et al. (1993) "A Kinetic Model for Amyloid Formation in the Prion Diseases: Importance of Seeding" Proc. Natl. Acad. Sci. USA 90: 5959–5963.

Evans, Krista C et al. (1995) "Apolipoprotein E Is a Kinetic But Not a Thermodynamic Inhibitor of Amyloid Formation: Implications for the Pathogenesis and Treatment of Alzheimer Disease" Proc. Natl Acad. Sci. USA 92: 763–767.

Fabian, Heinz et al (1993) "Comparative Analysis of Human and Dutch–Type Alzheimer β–Amyloid Peptides by Infrared Spectroscopy and Circular Dichroism" Biochemical and Biophysical Research Communications 191(1) 232–239.

Fabian, Heinz et al. (1994) "Synthetic Post–Translationally Modified Human Aβ Peptide Exhibits a Markedly Increased Tendency to Form β–Pleated Sheets in vitro" Eur. J. Biochem. 221. 959–964.

Flood, J. et al. (1994) "Topography of a Binding Site for Small Amnestic Peptides Deduced from Structure–activity Studies. Relation to Amnestic Effect of Amyloid β Protein," PNAS, 91:380–4.

Fraser, Paul E. et al. (1994) "Conformation and Fibrillogenesis of Alzheimer Aβ Peptides with Selected Substitution of Charges Residues" J. Mol Biol. 224: 64–73.

Fraser, Paul E. et al. (1992) "Fibril Formation by Primate, Rodent, and Dutch–Hemorrhagic Analogues of Alzheimer Amyloid β–Protein" Biochemistry 31: 10716–10723.

Gorevic, PD et al. (1987) "Ten to Fourteen Residue Peptides of Alzheimer's Disease Protein are Sufficient for Amyloid Fibril Formation and Its Characteristic Xray Diffraction Pattern" Biochemical and Biophysical Research Communications 147(2) 854–862.

Gowing, Eric et al. (1994) "Chemical Characterization of Aβ 17–42 Peptide, a Component of Diffuse Amyloid Deposits of Alzheimer Disease" J. Biol. Chem. 269(15): 10987–10990.

Halverson, Kurt et al. (1990) "Molecular Determinants of Amyloid Deposition in Alzheimer's Disease: Conformational Studies of Synthetic β–Protein Fragments" Biochemistry 29(11) 2639–2644.

Hansen, Morten B. et al. (1989) "Re–examination and Further Development of a Precise and Rapid Dye Method for Measuring Cell Growth/Cell Kill" J. Immunol. Meth. 119: 203–210.

Hardy, John A and Gerald A. Higgins (1992) "Alzheimer's Disease: The Amyloid Cascade Hypothesis" Science 256. 184–185.

Hendrix, Julia et al. (1992) "A Convergent Synthesis of the Amyload Protein of Alzheimer's Disease" J. Am. Che. Soc. 114: 7930–7931.

Hilbich, Caroline et al. (1991) "Aggregation and Secondary Structure of Synthetic Amyloid βA4 Peptides of Alzheimer's Disease" J. Mol Biol. 218: 149–163.

Hilbich, Caroline et al. (1991) "Human and Rodent Sequence Analogs of Alzheimer's Amyloid βA4 Share Similar Properties and Can Be Solubilized in Buffers of pH 7 4" Eur. J. Biochem. 201: 61–69.

Hilbich, Caroline et al. (1992) "Substitutions of Hydrophobic Amino Acids Reduce the Amyloidogenicity of Alzheimer's Disease βA4 Peptides" J. Mol. Biol. 228: 460–473.

Inouye, H. et al. (1993) "Structure of β–Crystallite Assemblies Formed by Alzheimer β–Amyloid Protein Analogues: Analysis by X–ray Diffraction," Biophys J. 64: 502–19.

Isowa, Yoshikazu et al. (1977) "The Synthesis of Peptides of Means of Proteolytic Enzymes" Bulletin of the Chemical Society of Japan 50: 2762–2765.

Jarrett, Joseph T. and Peter T. Lansbury, Jr. (1993) "Seeding 'One–Dimensional Crystallization' of Amyloid. A Pathogenic Mechanism in Alzheimer's Disease and Scrapie?" Cell 73: 1055–1058.

Jarrett, Joseph T. et al. (1993) "The Carboxy Terminus of the β Amyloid Protein Is Critical for the Seeding of Amyloid Formation: Implications of the Pathogenesis of Alzheimer's Disease" Biochemistry 32(18): 4693–4697.

Katakai, Ryoichi (1977) "Sequential Polypeptides. The Steric Hindrance of L–Valine Residues in the Polycondensation of Peptide Active Esters" Bulletin of the Chemical Society of Japan 50(5):1173–1178.

Kelly, Jeffery W and Peter T. Lansbury, Jr. (1994) "A Chemical Approach to Elucidate the Mechanism of Transthyretin and β–Protein Amyloid Fibril Formation" Int. J. Exp. Clin. Invest 1: 186–205.

Kirschner, Daniel A. et al. (1987) "Synthetic Peptide Homologous to β Protein from Alzheimer Disease forms Amyloid–like Fibrils in vitro" Proc. Natl Acad. Sci. USA 84: 6953–6957.

Klunk, William E. and Jay W. Pettegrew (1990) "Alzheimer's β–Amyloid Protein Is Covalently Modified When Dissolved in Formic Acid" Journal of Neurochemistry 54(6) 2050–2054.

Koudinov, Alexei (1994) "The Soluble Form of Alzheimer's Amyloid Beta Protein is Complexed to High Density Lipoprotein 3 and Very High Density Lipoprotein in Normal Human Plasma" *Biochemical and Biophysical Research Communications* 205(2) 1164–1171.

Lansbury, Jr., Peter T (1992) "In Pursuit of the Molecular Structure of Amyloid Plaque. New Technology Provides Unexpected and Critical Information" *Biochemistry* 31(30): 6866–6870.

LeVine, III, Harry (1993) "Thioflavine T Interaction with Synthetic Alzheimer's Disease β–Amyloid Peptides: Detection of Amyloid Aggregation in Solution" *Protein Science* 2 404–410.

Maggio, John E. et al (1992) "Reversible in vitro Growth of Alzheimer Disease β–Amyloid Plaques by Deposition of Labeled Amyloid Peptide" *Proc. Natl. Acad. Sci. USA* 89: 5462–5466.

Miller, Brian T et al. (1994) "Identification and Characterization of O–Biotinylated Hydroxy Amino Acid Residues in Peptides" *Analytical Biochemistry* 219. 240–248.

Orlando, Ron et al. (1992) "Covalent Modification of Alzheimer's Amyloid β–Peptide in Formic Acid Solutions" *Biochemical and Biophysical Research Communications* 184(2): 686–691.

Pike, Christian J. et al. (1993) "Neurodegeneration Induced by β–Amyloid Peptides in vitro: the Role of Peptide Assembly State" *Journal of Neuroscience* 13(4): 1676–1687.

Pike, Christian J. et al. (1995) "Structure–Activity Analyses of β–Amyloid Peptides Contributions of the β25–35 Region to Aggregation and Neurotoxicity" *Journal of Neurochemistry* 64(1): 253–265.

Saito, Yasunari et al. (1995) "Vector–mediated Delivery of $^{125}$I–labeled B–amyloid Peptide Aβ$^{1-40}$ Through the Blood–brain Barrier and Binding to Alzheimer disease Amyloid of the AB$^{1-40}$/Vector Complex" *Proc. Natl Acad. Sci. USA* vol. 91 10227–10231.

Schwarzman, Alexander L. et al. (1994) "Transthyretin Sequesters Amyloid β Protein and Prevents Amyloid Formation" *Proc Natl. Acad. Sci USA* 91: 8368–8372.

Shearman, Mark S. et al (1994) "Inhibition of PC12 Cell Redox Activity is a Specific Early Indicator of the Mechanism of β–Amyloid–Mediated Cell Death" *Proc. Natl. Acad. Sci USA* 91 1470–1474.

Shen, Chih–Lung et al (1994) "Effect of Acid Predissolution on Fibril Size and Fibril Flexibility of Synthetic β–Amyloid Peptide" *Biophysical Journal* 67: 1238–1246.

Shen, Chih–Lung et al. (1993) "Light Scattering Analysis of Fibril Growth from the Amino–Terminal Fragment β(1–28) of β–Amyloid Peptide" *Biophysical Journal* 65: 2383–2395.

Snyder, Seth W. et al (1994) "Amyloid–β Aggregation: Selective Inhibition of Aggregation in Mixtures of Amyloid with Different Chain Lengths" *Biophysical Journal* 67: 1216–1228.

Sonnenberg–Reines, J. et al. (1993) "Biothylated and Cysteine Modified Peptides as Useful Reagents for Studying the Inhibition of Putative N–terminal B–Amyloid Peptide Enzymes," *Society for Neuroscience Abstracts* 19:861.

Soreghan, Brian et al. (1994) "Surfactant Properties of Alzheimer's Aβ Peptides and the Mechanism of Amyloid Aggregation" *The Journal of Biological Chemistry* 269(46): 28551–28554.

Sorimachi, Kay and David J. Craik (1994) "Structure Determination of Extracellular Fragments of Amyloid Proteins Involved in Alzheimer's Disease and Dutch–type Hereditary Cerebral Haemorrhage with Amyloidosis" *Eur. J. Biochem* 219: 237–251.

Soto, C. et al. (1996) "Inhibition of Alzheimer's Amyloidosis by Peptides that Prevent β–Sheet Conformation," *Biochemical and Biophysical Research Communications* 226 672–80.

Strittmatter, Warren J. et al (1993) "Binding of Human Apolipoprotein E to Synthetic Amyloid β Peptide: Isoform–Specific Effects and Implications for Late–Onset Alzheimer Disease" *Proc. Natl. Acad. Sci. USA* 90. 8098–8102.

Tjernberg, L. et al. (1996) "Arrest of β–Amyloid Fibril Formation by a Pentapeptide Ligand," *The Journal of Biological Chemistry* 271(15):8545–8.

Tjernberg, L et al. (1997) "Controlling Amyloid β–Peptide Fibril Formation with Protease–stable Ligands," *The Journal of Biological Chemistry* 272(19): 12601–6.

Tomiyama, Takami et al (1994) "Racemization of Asp$^{23}$ Residue Affects the Aggregation Properties of Alzheimer Amyloid β Protein Analogues" *J. Biol. Chem.* 269(14) 10205–10208.

Tomski, Sharon J and Regina M Murphy (1992) "Kinetics of Aggregation of Synthetic β–Amyloid Peptide" *Archives of Biochemistry and Biophysics* 294(2): 630–638.

Vitek, Michael P. et al. (1994) "Advanced Glycation End Products Contribute to Amyloidosis in Alzheimer Disease" *Proc. Natl Acad. Sci. USA* 91: 4766–4770.

Vogler, K. et al. (1965) "Synthese von All–D–Val$^5$–Angiotensin il–Asp$^1$–β–Amid$^1$)," *Helv. Chim. Acta* 48(152):1407–14.

Vogler, K et al. (1966) "Synthesen von Bradykinn–Analogen mit D–Aminosauren (all–D–Bradykinin und all–D–retro–Bradikinin$^1$)$^2$)," *Helv. Chim. Acta.* 49(43):390–403.

Vyas, S. B. et al (1992) "Characterization of Aggregation in Alzheimer β–protein Using Synthetic Peptide Fragments on Reverse–Phase Matrix," *Peptides, Chemistry and Biology* (J.A. Smith and J.E. Rivier, eds,), ESCOM, Leiden, 278–279.

Weinreb, Paul H. et al (1994) "Peptide Models of a Hydrophobic Cluster at the C–Terminus of the β–Amyloid Protein" *Journal of the American Chemical Society* 116(23) 10835–10836;.

Wood, S. et al. (1995) "Prolines and Amyloidogenicity in Fragments of the Alzheimer's Peptide βIA4," *Biochemistry* 34.724–30.

```
                          SEQUENCE LISTING (1) GENERAL INFORMATION:

(iii) NUMBER OF SEQUENCES: 34

(2) INFORMATION FOR SEQ ID NO:1:

(i) SEQUENCE CHARACTERISTICS:
          (A) LENGTH: 43 amino acids
          (B) TYPE: amino acid
          (D) TOPOLOGY: linear (ii) MOLECULE TYPE: peptide (v) FRAGMENT TYPE: internal (xi) SEQUENCE DESCRIPTION: SEQ ID NO:1:

Asp Ala Glu Phe Arg His Asp Ser Gly Tyr Glu Val His His Gln Lys
1               5                  10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr
            35                  40

(2) INFORMATION FOR SEQ ID NO:2:

(i) SEQUENCE CHARACTERISTICS:
          (A) LENGTH: 103 amino acids
          (B) TYPE: amino acid
          (D) TOPOLOGY: linear (ii) MOLECULE TYPE: peptide (v) FRAGMENT TYPE: internal (xi) SEQUENCE DESCRIPTION: SEQ ID NO:2:

Glu Val Lys Met Asp Ala Glu Phe Arg His Asp Ser Gly Tyr Glu Val
1               5                  10                  15

His His Gln Lys Leu Val Phe Phe Ala Glu Asp Val Gly Ser Asn Lys
            20                  25                  30

Gly Ala Ile Ile Gly Leu Met Val Gly Gly Val Val Ile Ala Thr Val
            35                  40                  45

Ile Val Ile Thr Leu Val Met Leu Lys Lys Lys Gln Tyr Thr Ser Ile
    50                  55                  60

His His Gly Val Val Glu Val Asp Ala Ala Val Thr Pro Glu Glu Arg
65                  70                  75                  80

His Leu Ser Lys Met Gln Gln Asn Gly Tyr Glu Asn Pro Thr Tyr Lys
            85                  90                  95

Phe Phe Glu Gln Met Gln Asn
            100

(2) INFORMATION FOR SEQ ID NO:3:

(i) SEQUENCE CHARACTERISTICS:
          (A) LENGTH: 5 amino acids
          (B) TYPE: amino acid
          (D) TOPOLOGY: linear (ii) MOLECULE TYPE: peptide
```

(xi) SEQUENCE DESCRIPTION: SEQ ID NO:3:

Leu Val Phe Phe Ala
                5

(2) INFORMATION FOR SEQ ID NO:4:

(i) SEQUENCE CHARACTERISTICS:
          (A) LENGTH: 5 amino acids
          (B) TYPE: amino acid
          (D) TOPOLOGY: linear (ii) MOLECULE TYPE: peptide (ix) FEATURE:
          (A) NAME/KEY: Modified site
          (B) LOCATION: 1-5
          (D) OTHER INFORMATION: /note= D amino acid (xi) SEQUENCE DESCRIPTION: SEQ ID NO:4:

Ala Phe Phe Val Leu
                5

(2) INFORMATION FOR SEQ ID NO:5:

(i) SEQUENCE CHARACTERISTICS:
          (A) LENGTH: 5 amino acids
          (B) TYPE: amino acid
          (D) TOPOLOGY: linear (ii) MOLECULE TYPE: peptide (ix) FEATURE:
          (A) NAME/KEY: Modified site
          (B) LOCATION: 1-5
          (D) OTHER INFORMATION: /note= D amino acid (xi) SEQUENCE DESCRIPTION: SEQ ID NO:5:

Ala Phe Phe Leu Leu
                5

(2) INFORMATION FOR SEQ ID NO:6:

(i) SEQUENCE CHARACTERISTICS:
          (A) LENGTH: 5 amino acids
          (B) TYPE: amino acid
          (D) TOPOLOGY: linear (ii) MOLECULE TYPE: peptide (ix) FEATURE:
          (A) NAME/KEY: Modified site
          (B) LOCATION: 1-5
          (D) OTHER INFORMATION: /note= D amino acid (xi) SEQUENCE DESCRIPTION: SEQ ID NO:6:

Leu Phe Phe Val Leu
                5

(2) INFORMATION FOR SEQ ID NO:7:

(i) SEQUENCE CHARACTERISTICS:
          (A) LENGTH: 5 amino acids
          (B) TYPE: amino acid
          (D) TOPOLOGY: linear (ii) MOLECULE TYPE: peptide (ix) FEATURE:
          (A) NAME/KEY: Modified site
          (B) LOCATION: 1-5
          (D) OTHER INFORMATION: /note= D amino acid (xi) SEQUENCE DESCRIPTION: SEQ ID NO:7:

Phe Phe Phe Val Leu
                5

(2) INFORMATION FOR SEQ ID NO:8:

(i) SEQUENCE CHARACTERISTICS:
         (A) LENGTH: 4 amino acids
         (B) TYPE: amino acid
         (D) TOPOLOGY: linear (ii) MOLECULE TYPE: peptide (xi) SEQUENCE DESCRIPTION: SEQ ID NO:8:

Leu Val Phe Phe (2) INFORMATION FOR SEQ ID NO:9:

(i) SEQUENCE CHARACTERISTICS:
         (A) LENGTH: 4 amino acids
         (B) TYPE: amino acid
         (D) TOPOLOGY: linear (ii) MOLECULE TYPE: peptide (ix) FEATURE:
         (A) NAME/KEY: Modified site
         (B) LOCATION: 1-4
         (D) OTHER INFORMATION: /note= D amino acid (xi) SEQUENCE DESCRIPTION: SEQ ID NO:9:

Leu Val Phe Phe (2) INFORMATION FOR SEQ ID NO:10:

(i) SEQUENCE CHARACTERISTICS:
         (A) LENGTH: 3 amino acids
         (B) TYPE: amino acid
         (D) TOPOLOGY: linear (ii) MOLECULE TYPE: peptide (ix) FEATURE:
         (A) NAME/KEY: Modified site
         (B) LOCATION: 1-3
         (D) OTHER INFORMATION: /note= D amino acid (ix) FEATURE:
         (A) NAME/KEY: Modified site
         (B) LOCATION: 3
         (D) OTHER INFORMATION: /note= phenethylamide C-terminal
              modification (xi) SEQUENCE DESCRIPTION: SEQ ID NO:10:

Leu Val Phe (2) INFORMATION FOR SEQ ID NO:11:

(i) SEQUENCE CHARACTERISTICS:
         (A) LENGTH: 4 amino acids
         (B) TYPE: amino acid
         (D) TOPOLOGY: linear (ii) MOLECULE TYPE: peptide (ix) FEATURE:
         (A) NAME/KEY: Modified site
         (B) LOCATION: 1-4
         (D) OTHER INFORMATION: /note= D amino acid (xi) SEQUENCE DESCRIPTION: SEQ ID NO:11:

```
Leu Val Tyr Phe (2) INFORMATION FOR SEQ ID NO:12:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (ix) FEATURE:
        (A) NAME/KEY: Modified site
        (B) LOCATION: 1-4
        (D) OTHER INFORMATION: /note= D amino acid (ix) FEATURE:
        (A) NAME/KEY: Modified site
        (B) LOCATION: 3
        (D) OTHER INFORMATION: /note= Xaa=iodotyrosine (xi) SEQUENCE DESCRIPTION: SEQ ID NO:12:

Leu Val Xaa Phe (2) INFORMATION FOR SEQ ID NO:13:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (ix) FEATURE:
        (A) NAME/KEY: Modified site
        (B) LOCATION: 1-4
        (D) OTHER INFORMATION: /note= D amino acid (xi) SEQUENCE DESCRIPTION: SEQ ID NO:13:

Leu Val Phe Tyr (2) INFORMATION FOR SEQ ID NO:14:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (ix) FEATURE:
        (A) NAME/KEY: Modified site
        (B) LOCATION: 1-4
        (D) OTHER INFORMATION: /note= D amino acid (ix) FEATURE:
        (A) NAME/KEY: Modified site
        (B) LOCATION: 4
        (D) OTHER INFORMATION: /note= Xaa=iodotyrosine (xi) SEQUENCE DESCRIPTION: SEQ ID NO:14:

Leu Val Phe Xaa (2) INFORMATION FOR SEQ ID NO:15:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (ix) FEATURE:
```

```
            (A) NAME/KEY: Modified site
            (B) LOCATION: 1-4
            (D) OTHER INFORMATION: /note= D amino acid (xi) SEQUENCE DESCRIPTION: SEQ ID NO:15:

Leu Val Phe Ala (2) INFORMATION FOR SEQ ID NO:16:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (ix) FEATURE:
            (A) NAME/KEY: Modified site
            (B) LOCATION: 1-5
            (D) OTHER INFORMATION: /note= D amino acid (xi) SEQUENCE DESCRIPTION: SEQ ID NO:16:

Leu Val Phe Phe Ala
                5

(2) INFORMATION FOR SEQ ID NO:17:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (ix) FEATURE:
            (A) NAME/KEY: Modified site
            (B) LOCATION: 1-5
            (D) OTHER INFORMATION: /note= D amino acid (xi) SEQUENCE DESCRIPTION: SEQ ID NO:17:

Ala Val Phe Phe Leu
                5

(2) INFORMATION FOR SEQ ID NO:18:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (ix) FEATURE:
            (A) NAME/KEY: Modified site
            (B) LOCATION: 1-5
            (D) OTHER INFORMATION: /note= D amino acid (xi) SEQUENCE DESCRIPTION: SEQ ID NO:18:

Leu Val Tyr Phe Ala
                5

(2) INFORMATION FOR SEQ ID NO:19:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (ix) FEATURE:
            (A) NAME/KEY: Modified site
```

(B) LOCATION: 1-5
            (D) OTHER INFORMATION: /note= D amino acid (ix) FEATURE:
            (A) NAME/KEY: Modified site
            (B) LOCATION: 3
            (D) OTHER INFORMATION: /note= Xaa=iodotyrosine (xi) SEQUENCE DESCRIPTION: SEQ ID NO:19:

Leu Val Xaa Phe Ala
                5

(2) INFORMATION FOR SEQ ID NO:20:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (ix) FEATURE:
            (A) NAME/KEY: Modified site
            (B) LOCATION: 1-5
            (D) OTHER INFORMATION: /note= D amino acid (xi) SEQUENCE DESCRIPTION: SEQ ID NO:20:

Leu Val Phe Tyr Ala
                5

(2) INFORMATION FOR SEQ ID NO:21:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (ix) FEATURE:
            (A) NAME/KEY: Modified site
            (B) LOCATION: 1-5
            (D) OTHER INFORMATION: /note= D amino acid (ix) FEATURE:
            (A) NAME/KEY: Modified site
            (B) LOCATION: 4
            (D) OTHER INFORMATION: /note= Xaa=iodotyrosine (xi) SEQUENCE DESCRIPTION: SEQ ID NO:21:

Leu Val Phe Xaa Ala
                5

(2) INFORMATION FOR SEQ ID NO:22:

(i) SEQUENCE CHARACTERISTICS:
            (A) LENGTH: 4 amino acids
            (B) TYPE: amino acid
            (D) TOPOLOGY: linear (ii) MOLECULE TYPE: peptide (ix) FEATURE:
            (A) NAME/KEY: Modified site
            (B) LOCATION: 1-4
            (D) OTHER INFORMATION: /note= D amino acid (xi) SEQUENCE DESCRIPTION: SEQ ID NO:22:

Phe Phe Val Leu (2) INFORMATION FOR SEQ ID NO:23:

```
        (i) SEQUENCE CHARACTERISTICS:
            (A) LENGTH: 4 amino acids
            (B) TYPE: amino acid
            (D) TOPOLOGY: linear (ii) MOLECULE TYPE: peptide (ix) FEATURE:
            (A) NAME/KEY: Modified site
            (B) LOCATION: 1-4
            (D) OTHER INFORMATION: /note= D amino acid (xi) SEQUENCE DESCRIPTION: SEQ ID NO:23:

Ala Phe Phe Val (2) INFORMATION FOR SEQ ID NO:24:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (ix) FEATURE:
            (A) NAME/KEY: Modified site
            (B) LOCATION: 1-5
            (D) OTHER INFORMATION: /note= D amino acid (xi) SEQUENCE DESCRIPTION: SEQ ID NO:24:

Phe Phe Phe Leu Val
                 5

(2) INFORMATION FOR SEQ ID NO:25:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (ix) FEATURE:
            (A) NAME/KEY: Modified site
            (B) LOCATION: 1-5
            (D) OTHER INFORMATION: /note= D amino acid (xi) SEQUENCE DESCRIPTION: SEQ ID NO:25:

Phe Phe Phe Phe Leu
                 5

(2) INFORMATION FOR SEQ ID NO:26:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (ix) FEATURE:
            (A) NAME/KEY: Modified site
            (B) LOCATION: 1-5
            (D) OTHER INFORMATION: /note= D amino acid (xi) SEQUENCE DESCRIPTION: SEQ ID NO:26:

Ala Phe Phe Phe Leu
                 5

(2) INFORMATION FOR SEQ ID NO:27:

(i) SEQUENCE CHARACTERISTICS:
```

(A) LENGTH: 5 amino acids
            (B) TYPE: amino acid
            (D) TOPOLOGY: linear (ii) MOLECULE TYPE: peptide (ix) FEATURE:
            (A) NAME/KEY: Modified site
            (B) LOCATION: 1-5
            (D) OTHER INFORMATION: /note= D amino acid (xi) SEQUENCE DESCRIPTION: SEQ ID NO:27:

Leu Val Phe Phe Phe
                5

(2) INFORMATION FOR SEQ ID NO:28:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (ix) FEATURE:
            (A) NAME/KEY: Modified site
            (B) LOCATION: 1-5
            (D) OTHER INFORMATION: /note= D amino acid (xi) SEQUENCE DESCRIPTION: SEQ ID NO:28:

Leu Val Phe Phe Val
                5

(2) INFORMATION FOR SEQ ID NO:29:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (ix) FEATURE:
            (A) NAME/KEY: Modified site
            (B) LOCATION: 1-5
            (D) OTHER INFORMATION: /note= D amino acid (xi) SEQUENCE DESCRIPTION: SEQ ID NO:29:

Leu Val Tyr Tyr Ala
                5

(2) INFORMATION FOR SEQ ID NO:30:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (ix) FEATURE:
            (A) NAME/KEY: Modified site
            (B) LOCATION: 1-5
            (D) OTHER INFORMATION: /note= D amino acid (xi) SEQUENCE DESCRIPTION: SEQ ID NO:30:

Leu Phe Phe Phe Leu
                5

(2) INFORMATION FOR SEQ ID NO:31:

(i) SEQUENCE CHARACTERISTICS:

(A) LENGTH: 5 amino acids
            (B) TYPE: amino acid
            (D) TOPOLOGY: linear (ii) MOLECULE TYPE: peptide (ix) FEATURE:
            (A) NAME/KEY: Modified site
            (B) LOCATION: 5
            (D) OTHER INFORMATION: /note= Adp modification (xi) SEQUENCE DESCRIPTION: SEQ ID NO:31:

Asp Asp Ile Ile Leu
                5

(2) INFORMATION FOR SEQ ID NO:32:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (xi) SEQUENCE DESCRIPTION: SEQ ID NO:32:

Leu Val Tyr Phe Ala
                5

(2) INFORMATION FOR SEQ ID NO:33:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (ix) FEATURE:
            (A) NAME/KEY: Modified site
            (B) LOCATION: 1
            (D) OTHER INFORMATION: /note= cholyl modification (ix) FEATURE:
            (A) NAME/KEY: Modified site
            (B) LOCATION: 5
            (D) OTHER INFORMATION: /note= amide modification (xi) SEQUENCE DESCRIPTION: SEQ ID NO:33:

Leu Val Phe Phe Ala
                5

(2) INFORMATION FOR SEQ ID NO:34:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (ix) FEATURE:
            (A) NAME/KEY: Modified site
            (B) LOCATION: 1
            (D) OTHER INFORMATION: /note= cholyl modification (ix) FEATURE:
            (A) NAME/KEY: Modified site
            (B) LOCATION: 5
            (D) OTHER INFORMATION: /note= hydroxyl modification (xi) SEQUENCE DESCRIPTION: SEQ ID NO:34:

Leu Val Phe Phe Ala

1

MODULATORS OF β-AMYLOID PEPTIDE AGGREGATION COMPRISING D-AMINO ACIDS

RELATED APPLICATIONS

This application is a continuation-in-part of U.S. patent application Ser. No. 08/548,998, filed Oct. 27, 1995, now abandoned, U.S. patent application Ser. No. 08/616,081, filed Mar. 14, 1996, now abandoned, U.S. patent application Ser. No. 08/703,675, filed Aug. 27, 1996, and U.S. patent application Ser. No. 08/897,342, filed Jul. 21, 1997, now abandoned, the entire contents of each of which are hereby incorporated by reference.

BACKGROUND OF THE INVENTION

Alzheimer's disease (AD), first described by the Bavarian psychiatrist Alois Alzheimer in 1907, is a progressive neurological disorder that begins with short term memory loss and proceeds to disorientation, impairment of judgment and reasoning and, ultimately, dementia. The course of the disease usually leads to death in a severely debilitated, immobile state between four and 12 years after onset. AD has been estimated to afflict 5 to 11 percent of the population over age 65 and as much as 47 percent of the population over age 85. The societal cost for managing AD is upwards of 80 billion dollars annually, primarily due to the extensive custodial care required for AD patients. Moreover, as adults born during the population boom of the 1940's and 1950's approach the age when AD becomes more prevalent, the control and treatment of AD will become an even more significant health care problem. Currently, there is no treatment that significantly retards the progression of the disease. For reviews on AD, see Selkoe, D. J. *Sci. Amer.*, November 1991, pp. 68–78; and Yankner, B. A. et al. (1991) *N. Eng. J. Med.* 325:1849–1857.

It has recently been reported (Games et al. (1995) *Nature* 373:523–527) that an Alzheimer-type neuropathology has been created in transgenic mice. The transgenic mice express high levels of human mutant amyloid precursor protein and progressively develop many of the pathological conditions associated with AD.

Pathologically, AD is characterized by the presence of distinctive lesions in the victim's brain. These brain lesions include abnormal intracellular filaments called neurofibrillary tangles (NTFs) and extracellular deposits of amyloidogenic proteins in senile, or amyloid, plaques. Amyloid deposits are also present in the walls of cerebral blood vessels of AD patients. The major protein constituent of amyloid plaques has been identified as a 4 kilodalton peptide called β-amyloid peptide (β-AP)(Glenner, G. G. and Wong, C. W. (1984) *Biochem. Biophys. Res. Commun.* 120:885–890; Masters, C. et al. (1985) *Proc. Natl. Acad Sci. USA* 82:4245–4249). Diffuse deposits of β-AP are frequently observed in normal adult brains, whereas AD brain tissue is characterized by more compacted, dense-core β-amyloid plaques. (See e.g., Davies, L. et al. (1988) *Neurology* 38:1688–1693). These observations suggest that β-AP deposition precedes, and contributes to, the destruction of neurons that occurs in AD. In further support of a direct pathogenic role for β-AP, β-amyloid has been shown to be toxic to mature neurons, both in culture and in vivo. Yankner, B. A. et al. (1989) *Science* 245:417–420; Yankner, B. A. et al. (1990) *Proc. Natl. Acad. Sci. USA* 87:9020–9023; Roher, A. E. et al. (1991) *Biochem. Biophys. Res. Commun.* 174:572–579; Kowall, N. W. et al. (1991) *Proc. Natl. Acad. Sci. USA* 88:7247–7251. Furthermore, patients with heredi-

2 tary cerebral hemorrhage with amyloidosis-Dutch-type (HCHWA-D), which is characterized by diffuse β-amyloid deposits within the cerebral cortex and cerebrovasculature, have been shown to have a point mutation that leads to an amino acid substitution within β-AP. Levy, E. et al. (1990) *Science* 248:1124–1126. This observation demonstrates that a specific alteration of the β-AP sequence can cause β-amyloid to be deposited.

Natural β-AP is derived by proteolysis from a much larger protein called the amyloid precursor protein (APP). Kang, J. et al. (1987) *Nature* 325:733; Goldgaber, D. et al. (1987) *Science* 235:877; Robakis, N. K. et al. (1987) *Proc. Natl. Acad. Sci. USA* 84:4190; Tanzi, R. E. et al. (1987) *Science* 235:880. The APP gene maps to chromosome 21, thereby providing an explanation for the β-amyloid deposition seen at an early age in individuals with Down's syndrome, which is caused by trisomy of chromosome 21. Mann, D. M. et al. (1989) *Neuropathol. Appl. Neurobiol.* 15:317; Rumble, B. et al. (1989) *N. Eng. J. Med.* 320:1446. APP contains a single membrane spanning domain, with a long amino terminal region (about two-thirds of the protein) extending into the extracellular environment and a shorter carboxy-terminal region projecting into the cytoplasm. Differential splicing of the APP messenger RNA leads to at least five forms of APP, composed of either 563 amino acids (APP-563), 695 amino acids (APP-695), 714 amino acids (APP-714), 751 amino acids (APP-751) or 770 amino acids (APP-770).

Within APP, naturally-occurring β amyloid peptide begins at an aspartic acid residue at amino acid position 672 of APP-770. Naturally-occurring β-AP derived from proteolysis of APP is 39 to 43 amino acid residues in length, depending on the carboxy-terminal end point, which exhibits heterogeneity. The predominant circulating form of β-AP in the blood and cerebrospinal fluid of both AD patients and normal adults is β1-40 ("short β"). Seubert, P. et al. (1992) *Nature* 359:325; Shoji, M. et al. (1992) *Science* 258:126. However, β1-42 and β1-43 ("long β") also are forms in β-amyloid plaques. Masters, C. et al. (1985) *Proc. Natl. Acad. Sci. USA* 82:4245; Miller, D. et al. (1993) *Arch. Biochem. Biophys.* 301:41; Mori, H. et al. (1992) *J. Biol. Chem.* 267:17082. Although the precise molecular mechanism leading to β-APP aggregation and deposition is unknown, the process has been likened to that of nucleation-dependent polymerizations, such as protein crystallization, microtubule formation and actin polymerization. See e.g., Jarrett, J. T. and Lansbury, P. T. (1993) *Cell* 73:1055–1058. In such processes, polymerization of monomer components does not occur until nucleus formation. Thus, these processes are characterized by a lag time before aggregation occurs, followed by rapid polymerization after nucleation. Nucleation can be accelerated by the addition of a "seed" or preformed nucleus, which results in rapid polymerization. The long β forms of β-AP have been shown to act as seeds, thereby accelerating polymerization of both long and short β-AP forms. Jarrett, J. T. et al. (1993) *Biochemistry* 32:4693.

In one study, in which amino acid substitutions were made in β-AP, two mutant β peptides were reported to interfere with polymerization of non-mutated β-AP when the mutant and non-mutant forms of peptide were mixed. Hilbich, C. et al. (1992) *J. Mol. Biol.* 228:460–473. Equimolar amounts of the mutant and non-mutant (i.e., natural) β amyloid peptides were used to see this effect and the mutant peptides were reported to be unsuitable for use in vivo. Hilbich, C. et al. (1992), supra.

SUMMARY OF THE INVENTION

This invention pertains to compounds, and pharmaceutical compositions thereof, that can bind to natural β amyloid peptides (β-AP), modulate the aggregation of natural β-AP and/or inhibit the neurotoxicity of natural β-APs. The β-amyloid modulator compounds of the invention comprise a peptidic structure, preferably based on β-amyloid peptide, that is composed entirely of D-amino acids. In various embodiments, the peptidic structure of the modulator compound comprises a D-amino acid sequence corresponding to a L-amino acid sequence found within natural β-AP, a D-amino acid sequence which is a retro-inverso isomer of an L-amino acid sequence found within natural β-AP or a D-amino acid sequence that is a scrambled or substituted version of an L-amino acid sequence found within natural β-AP. Preferably, the D-amino acid peptidic structure of the modulator is designed based upon a subregion of natural β-AP at positions 17–21 (Aβ$_{17-20}$ and Aβ$_{17-21}$, respectively), which has the amino acid sequences Leu-Val-Phe-Phe-Ala (SEQ ID NO: 3).

A modulator compound of the invention preferably comprises 3–20 D-amino acids, more preferably 3–10 D-amino acids and even more preferably 3–5 D-amino acids. The D-amino acid peptidic structure of the modulator can have free amino- and carboxy-termini. Alternatively, the amino-terminus, the carboxy-terminus or both may be modified. For example, an N-terminal modifying group can be used that enhances the ability of the compound to inhibit Aβ aggregation. Moreover, the amino- and/or carboxy termini of the peptide can be modified to alter a pharmacokinetic property of the compound (such as stability, bioavailability and the like). Preferred carboxy-terminal modifying groups include amide groups, alkyl or aryl amide groups (e.g., phenethylamide) and hydroxy groups (i.e., reduction products of peptide acids, resulting in peptide alcohols). Still further, a modulator compound can be modified to label the compound with a detectable substance (e.g., a radioactive label).

In certain preferred embodiments, the invention provides a compound having the structure:

A-(Xaa)-B wherein (Xaa) is a peptidic structure selected from the group consisting of D-Leu-D-Val-D-Phe-D-Phe, D-Leu-D-Val-D-Phe-phenethylamide, D-Leu-D-Val-D-Tyr-D-Phe, D-Leu-D-Val-D-IodoTyr-D-Phe, D-Leu-D-Val-D-Phe-D-Tyr, D-Leu-D-Val-D-Phe-D-IodoTyr, D-Leu-D-Val-D-Phe-D-Ala, D-Leu-D-Val-D-Phe-D-Phe-D-Ala, D-Ala-D-Val-D-Phe-D-Phe-D-Leu, D-Leu-D-Val-D-Tyr-D-Phe-D-Ala, D-Leu-D-Val-D-IodoTyr-D-Phe-D-Ala, D-Leu-D-Val-D-Phe-D-Tyr-D-Ala, D-Leu-D-Val-D-Phe-D-IodoTyr-D-Ala, D-Phe-D-Phe-D-Val-D-Leu, D-Ala-D-Phe-D-Phe-D-Val, D-Ala-D-Phe-D-Phe-D-Val-D-Leu, D-Ala-D-Phe-D-Phe-D-Leu-D-Leu, D-Leu-D-Phe-D-Phe-D-Val-D-Leu, D-Phe-D-Phe-D-Phe-D-Val-D-Leu, D-Phe-D-Phe-D-Phe-D-Leu-D-Val, D-Phe-D-Phe-D-Phe-D-Phe-D-Leu and D-Ala-D-Phe-D-Phe-D-Phe-D-Leu.

A is an amino-terminal modifying group selected from the group consisting of phenylacetyl, diphenylacetyl, triphenylacetyl, butanoyl, isobutanoyl hexanoyl, propionyl, 3-hydroxybutanoyl, 4-hydroxybutanoyl, 3-hydroxypropionoyl, 2,4-dihydroxybutyroyl, 1-Adamantanecarbonyl, 4-methylvaleryl, 2-hydroxyphenylacetyl, 3-hydroxyphenylacetyl, 4-hydroxyphenylacetyl, 3,5-dihydroxy-2-naphthoyl, 3,7-dihydroxy-2-naphthoyl, 2-hydroxycinnamoyl, 3-hydroxycinnamoyl, 4-hydroxycinnamoyl, hydrocinnamoyl, 4-formylcinnamoyl, 3-hydroxy-4-methoxycinnamoyl, 4-hydroxy-3-methoxycinnamoyl, 2-carboxycinnamoyl, 3,4,-dihydroxyhydrocinnamoyl, 3,4-dihydroxycinnamoyl, trans-Cinnamoyl, (±)-mandelyl, (±)-mandelyl-(±)-mandelyl, glycolyl, 3-formylbenzoyl, 4-formylbenzoyl, 2-formylphenoxyacetyl, 8-formyl-1-naphthoyl, 4-(hydroxymethyl)benzoyl, 3-hydroxybenzoyl, 4-hydroxybenzoyl, 5-hydantoinacetyl, L-hydroorotyl, 2,4-dihydroxybenzoyl, 3-benzoylpropanoyl, (±)-2,4-dihydroxy-3,3-dimethylbutanoyl, DL-3-(4-hydroxyphenyl)lactyl, 3-(2-hydroxyphenyl)propionyl, 4-(2-hydroxyphenyl)propionyl, D-3-phenyllactyl, 3-(4-hydroxyphenyl)propionyl, L-3-phenyllactyl, 3-pyridylacetyl, 4-pyridylacetyl, isonicotinoyl, 4-quinolinecarboxyl, 1-isoquinolinecarboxyl and 3-isoquinolinecarboxyl.

and B is a carboxy-terminal modifying group selected from the group consisting of an amide group, an alkyl amide group, an aryl amide group and a hydroxy group.

In another embodiment, (Xaa) is a peptidic structure as described above, B is a carboxyl-terminal modifying group as described above and A is an amino-terminal modifying group selected from the group consisting of cholyl, lithocholyl, hyodeoxycholyl, chenodeoxycholyl and ursodeoxycholyl. In a preferred subembodiment, A is selected from the group consisting of lithocholyl, hyodeoxycholyl, chenodeoxycholyl and ursodeoxycholyl.

Particularly preferred compounds of the invention are set forth in the Examples.

Another aspect of the invention pertains to pharmaceutical compositions. Typically, the pharmaceutical composition comprises a therapeutically effective amount of a modulator compound of the invention and a pharmaceutically acceptable carrier.

Yet another aspect of the invention pertains to methods for inhibiting aggregation of natural β-amyloid peptides. These methods comprise contacting the natural β-amyloid peptides with a modulator compound of the invention such that aggregation of the natural β-amyloid peptides is inhibited.

Yet another aspect of the invention pertains to methods for detecting the presence or absence of natural β-amyloid peptides in a biological sample. These methods comprise contacting a biological sample with a compound of the invention, wherein the compound is labeled with a detectable substance, and detecting the compound bound to natural β-amyloid peptides to thereby detect the presence or absence of natural β-amyloid peptides in the biological sample.

Still another aspect of the invention pertains to methods for treating a subject for a disorder associated with β-amyloidosis. These methods comprise administering to the subject a therapeutically effective amount of a modulator compound of the invention such that the subject is treated for a disorder associated with β-amyloidosis. Preferably, the disorder is Alzheimer's disease. Use of the modulators of the invention for therapy or for the manufacture of a medicament for the treatment of a disorder associated with b-amyloidosis is also encompassed by the invention.

DETAILED DESCRIPTION OF THE INVENTION

Figure 1:
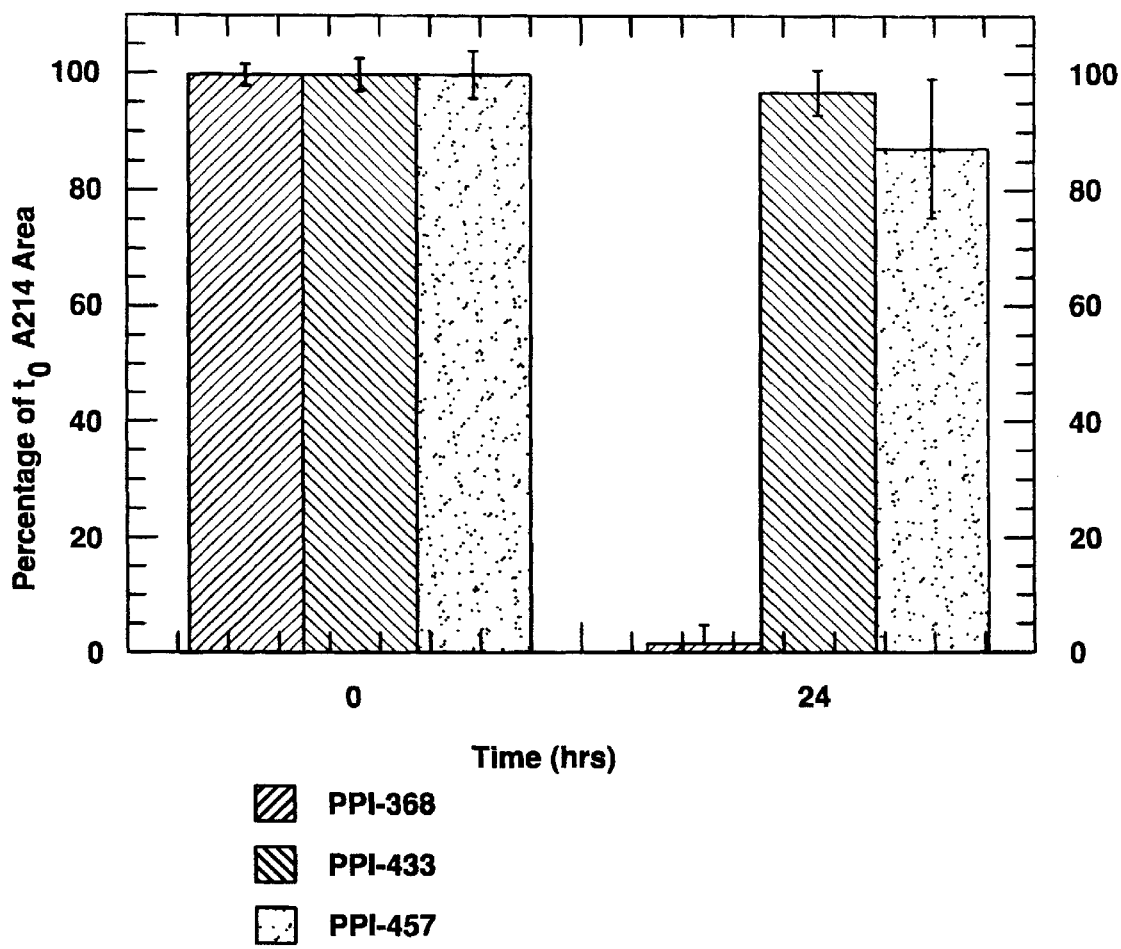
FIG. 1 is a bar graph depicting the stability of an L-amino acid-based modulator compound (PPI-368) and two D-amino acid-based modulator compounds (PPI-433 and PPI-457) in cerebrospinal fluid.

This invention pertains to compounds, and pharmaceutical compositions thereof, that can bind to natural β-amyloid peptides, modulate the aggregation of natural β amyloid peptides (β-AP) and/or inhibit the neurotoxicity of natural β-APs. A compound of the invention that modulates aggregation of natural β-AP, referred to herein interchangeably as a β amyloid modulator compound, a β amyloid modulator or simply a modulator, alters the aggregation of natural β-AP when the modulator is contacted with natural β-AP. Thus, a compound of the invention acts to alter the natural aggregation process or rate for β-AP, thereby disrupting this process. Preferably, the compounds inhibit β-AP aggregation. The compounds of the invention are characterized in that they comprise a peptidic structure composed entirely of D-amino acid residues. This peptidic structure is preferably based on β-amyloid peptide and can comprise, for example, a D-amino acid sequence corresponding to a L-amino acid sequence found within natural β-AP, a D-amino acid sequence which is a retro-inverso isomer of an L-amino acid sequence found within natural β-AP or a D-amino acid sequence that is a scrambled or substituted version of an L-amino acid sequence found within natural β-AP. The invention encompasses modulator compounds comprising a D-amino acid peptidic structure having free amino- and carboxy-termini, as well as modulator compounds in which the amino-terminus, the carboxy-terminus, and/or side chain (s) of the peptidic structure are modified.

The β amyloid modulator compounds of the invention can be selected based upon their ability to bind to natural β-amyloid peptides, modulate the aggregation of natural β-AP in vitro and/or inhibit the neurotoxicity of natural β-AP fibrils for cultured cells (using assays described herein). Preferred modulator compounds inhibit the aggregation of natural β-AP and/or inhibit the neurotoxicity of natural β-AP. However, modulator compounds selected based on one or both of these properties may have additional properties in vivo that may be beneficial in the treatment of amyloidosis. For example, the modulator compound may interfere with processing of natural β-AP (either by direct or indirect protease inhibition) or by modulation of processes that produce toxic β-AP, or other APP fragments, in vivo. Alternatively, modulator compounds may be selected based on these latter properties, rather than inhibition of Aβ aggregation in vitro. Moreover, modulator compounds of the invention that are selected based upon their interaction with natural β-AP also may interact with APP or with other APP fragments. Still further, a modulator compound of the invention can be characterized by its ability to bind to β-amyloid fibrils (which can be determined, for example, by radiolabeling the compound, contacting the compound with β-amyloid plaque and imaging the compound bound to the plaque), while not significantly altering the aggregation of the β-amyloid fibrils. Such a compound that binds efficiently to β-amyloid fibrils while not significantly altering the aggregation of the β-amyloid fibrils can be used, for example, to detect β-amyloid fibrils (e.g., for diagnostic purposes, as described further herein). It should be appreciated, however, that the ability of a particular compound to bind to β-amyloid fibrils and/or modulate their aggregation may vary depending upon the concentration of the compound. Accordingly, a compound that, at a low concentration, binds to β-amyloid fibrils without altering their aggregation may nevertheless inhibit aggregation of the fibrils at a higher concentration. All such compounds having the property of binding to β-amyloid fibrils and/or modulating the aggregation of the fibrils are intended to be encompassed by the invention.

As used herein, a "modulator" of β-amyloid aggregation is intended to refer to an agent that, when contacted with natural β amyloid peptides, alters the aggregation of the natural β amyloid peptides. The term "aggregation of β amyloid peptides" refers to a process whereby the peptides associate with each other to form a multimeric, largely insoluble complex. The term "aggregation" further is intended to encompass β amyloid fibril formation and also encompasses β-amyloid plaques.

The terms "natural β-amyloid peptide", "natural β-AP" and "natural Aβ peptide", used interchangeably herein, are intended to encompass naturally occurring proteolytic cleavage products of the β amyloid precursor protein (APP) which are involved in β-AP aggregation and β-amyloidosis. These natural peptides include β-amyloid peptides having 39–43 amino acids (i.e., $A\beta_{1-39}$, $A\beta_{1-40}$, $A\beta_{1-41}$, $A\beta_{1-42}$ and $A\beta_{1-43}$). The amino-terminal amino acid residue of natural β-AP corresponds to the aspartic acid residue at position 672 of the 770 amino acid residue form of the amyloid precursor protein ("APP-770"). The 43 amino acid long form of natural β-AP has the amino acid sequence

DAEFRHDSGYEVHHQKLVFFAEDVGSNK-GAIIGLMVGGVVIAT (also shown in SEQ ID NO: 1), whereas the shorter forms have 1–4 amino acid residues deleted from the carboxy-terminal end. The amino acid sequence of APP-770 from position 672 (i.e., the amino-terminus of natural β-AP) to its C-terminal end (103 amino acids) is shown in SEQ ID NO: 2. The preferred form of natural β-AP for use in the aggregation assays described herein is $A\beta_{1-40}$.

In the presence of a modulator of the invention, aggregation of natural β amyloid peptides is "altered" or "modulated". The various forms of the term "alteration" or "modulation" are intended to encompass both inhibition of β-AP aggregation and promotion of β-AP aggregation. Aggregation of natural β-AP is "inhibited" in the presence of the modulator when there is a decrease in the amount and/or rate of β-AP aggregation as compared to the amount and/or rate of β-AP aggregation in the absence of the modulator. The various forms of the term "inhibition" are intended to include both complete and partial inhibition of β-AP aggregation. Inhibition of aggregation can be quantitated as the fold increase in the lag time for aggregation or as the decrease in the overall plateau level of aggregation (i.e., total amount of aggregation), using an aggregation assay as described in the Examples. In various embodiments, a modulator of the invention increases the lag time of aggregation at least 1.2-fold, 1.5-fold, 1.8-fold, 2-fold, 2.5-fold, 3-fold, 4-fold or 5-fold. In various other embodiments, a modulator of the invention inhibits the plateau level of aggregation at least 10%, 20%, 30%, 40%, 50%, 75% or 100%.

A modulator which inhibits β-AP aggregation (an "inhibitory modulator compound") can be used to prevent or delay the onset of β-amyloid deposition. Preferably, inhibitory modulator compounds of the invention inhibit the formation and/or activity of neurotoxic aggregates of natural Aβ peptide (i.e., the inhibitory compounds can be used to inhibit the neurotoxicity of β-AP). Additionally, the inhibitory compounds of the invention preferably reduce the neurotoxicity of preformed β-AP aggregates, indicating that the inhibitory modulators can either bind to preformed Aβ fibrils or soluble aggregate and modulate their inherent neurotoxicity or that the modulators can perturb the equilibrium between monomeric and aggregated forms of β-AP in favor of the non-neurotoxic form.

Alternatively, in another embodiment, a modulator compound of the invention promotes the aggregation of natural Aβ peptides. The various forms of the term "promotion" refer to an increase in the amount and/or rate of β-AP aggregation in the presence of the modulator, as compared to the amount and/or rate of β-AP aggregation in the absence of the modulator. Such a compound which promotes Aβ aggregation is referred to as a stimulatory modulator compound. Stimulatory modulator compounds may be useful for sequestering β-amyloid peptides, for example in a biological compartment where aggregation of β-AP may not be deleterious to thereby deplete β-AP from a biological compartment where aggregation of β-AP is deleterious. Moreover, stimulatory modulator compounds can be used to promote Aβ aggregation in in vitro aggregation assays (e.g., assays such as those described in Example 2), for example in screening assays for test compounds that can then inhibit or reverse this Aβ aggregation (i.e., a stimulatory modulator compound can act as a "seed" to promote the formation of Aβ aggregates).

In a preferred embodiment, the modulators of the invention are capable of altering β-AP aggregation when contacted with a molar excess amount of natural β-AP. A "molar excess amount of natural β-AP" refers to a concentration of natural β-AP, in moles, that is greater than the concentration, in moles, of the modulator. For example, if the modulator and β-AP are both present at a concentration of 1 $\mu$M, they are said to be "equimolar", whereas if the modulator is present at a concentration of 1 $\mu$M and the β-AP is present at a concentration of 5 $\mu$M, the β-AP is said to be present at a 5-fold molar excess amount compared to the modulator. In preferred embodiments, a modulator of the invention is effective at altering natural β-AP aggregation when the natural β-AP is present at at least a 2-fold, 3-fold or 5-fold molar excess compared to the concentration of the modulator. In other embodiments, the modulator is effective at altering β-AP aggregation when the natural β-AP is present at at least a 10-fold, 20-fold, 33-fold, 50-fold, 100-fold, 500-fold or 1000-fold molar excess compared to the concentration of the modulator.

As used herein, the term "β amyloid peptide comprised entirely of D-amino acids", as used in a modulator of the invention, is intended to encompass peptides having an amino acid sequence identical to that of the natural sequence in APP, as well as peptides having acceptable amino acid substitutions from the natural sequence, but which is composed of D-amino acids rather than the natural L-amino acids present in natural β-AP. Acceptable amino acid substitutions are those that do not affect the ability of the D-amino acid-containing peptide to alter natural β-AP aggregation. Moreover, particular amino acid substitutions may further contribute to the ability of the peptide to alter natural β-AP aggregation and/or may confer additional beneficial properties on the peptide (e.g., increased solubility, reduced association with other amyloid proteins, etc.). A peptide having an identical amino acid sequence to that found within a parent peptide but in which all L-amino acids have been substituted with all D-amino acids is also referred to as an "inverso" compounds. For example, if a parent peptide is Thr-Ala-Tyr, the inverso form is D-Thr-D-Ala-D-Tyr.

As used herein, the term "retro-inverso isomer of a β amyloid peptide", as used in a modulator of the invention, is intended to encompass peptides in which the sequence of the amino acids is reversed as compared to the sequence in natural β-AP and all L-amino acids are replaced with D-amino acids. For example, if a parent peptide is Thr-Ala-Tyr, the retro-inverso form is D-Tyr-D-Ala-D-Thr. Compared to the parent peptide, a retro-inverso peptide has a reversed backbone while retaining substantially the original spatial conformation of the side chains, resulting in a retro-inverso isomer with a topology that closely resembles the parent peptide. See Goodman et al. "*Perspectives in Peptide Chemistry*" pp. 283–294 (1981). See also U.S. Pat. No. 4,522,752 by Sisto for further description of "retro-inverso" peptides.

Various additional aspects of the modulators of the invention, and the uses thereof, are described in further detail in the following subsections.

I. Modulator Compounds

In one embodiment, a modulator compound of the invention comprises a β-amyloid peptide, the β-amyloid peptide being comprised entirely of D-amino acids, wherein the compound binds to natural β-amyloid peptides or modulates the aggregation or inhibits the neurotoxicity of natural β-amyloid peptides when contacted with the natural β-amyloid peptides. Preferably, the β-amyloid peptide of the modulator is comprised of 3–20 D-amino acids, more preferably 3–10 D-amino acids, and even more preferably 3–5 D-amino acids. In one embodiment, the β-amyloid peptide of the modulator is amino-terminally modified, for example with a modifying group comprising a cyclic, heterocyclic, polycyclic or branched alkyl group. Examples of suitable N-terminal modifying groups are described further in subsection II below. In another embodiment, the β-amyloid peptide of the modulator is carboxy-terminally modified, for example the modulator can comprise a peptide amide, a peptide alkyl or aryl amide (e.g., a peptide phenethylamide) or a peptide alcohol. Examples of suitable C-terminal modifying groups are described further in subsections II and III below. The β-amyloid peptide of the modulator may be modified to enhance the ability of the modulator to alter β-AP aggregation or neurotoxicity. Additionally or alternatively, β-amyloid peptide of the modulator may be modified to alter a pharmacokinetic property of the modulator and/or to label the modulator with a detectable substance (described further in subsection III below).

In another embodiment, a modulator compound of the invention comprises a retro-inverso isomer of a β-amyloid peptide, wherein the compound binds to natural β-amyloid peptides or modulates the aggregation or inhibits the neurotoxicity of natural β-amyloid peptides when contacted with the natural β-amyloid peptides. Preferably, the retro-inverso isomer of the β-amyloid peptide is comprised of 3–20 D-amino acids, more preferably 3–10 D-amino acids, and even more preferably 3–5 D-amino acids. In one embodiment, the retro-inverso isomer is amino-terminally modified, for example with a modifying group comprising a cyclic, heterocyclic, polycyclic or branched alkyl group. Examples of suitable N-terminal modifying groups are described further in subsection II below. In another embodiment, the retro-inverso isomer is carboxy-terminally modified, for example with an amide group, an alkyl or aryl amide group (e.g., phenethylamide) or a hydroxy group (i.e., the reduction product of a peptide acid, resulting in a peptide alcohol). Examples of suitable C-terminal modifying groups are described further in subsections II and III below. The retro-inverso isomer may be modified to enhance the ability of the modulator to alter β-AP aggregation or neurotoxicity. Additionally or alternatively, the retro-inverso isomer may be modified to alter a pharmacokinetic property of the modulator and/or to label the modulator with a detectable substance (described further in subsection III below).

The modulators of the invention preferably are designed based upon the amino acid sequence of a subregion of natural β-AP. The term "subregion of a natural β-amyloid peptide" is intended to include amino-terminal and/or carboxy-terminal deletions of natural β-AP. The term "subregion of natural β-AP" is not intended to include full-length natural β-AP (i.e., "subregion" does not include $A\beta_{1-39}$, $A\beta_{1-40}$, $A\beta_{1-41}$, $A\beta_{1-42}$ and $A\beta_{1-43}$). A preferred subregion of natural β-amyloid peptide is an "Aβ aggregation core domain" (ACD). As used herein, the term "Aβ aggregation core domain" refers to a subregion of a natural β-amyloid peptide that is sufficient to modulate aggregation of natural β-APs when this subregion, in its L-amino acid form, is appropriately modified (e.g., modified at the amino-terminus), as described in detail in U.S. patent application Ser. No. 08/548,998 and U.S. patent application Ser. No. 08/616,081, the entire contents of each of which are expressly incorporated herein by reference. Preferably, the ACD is modeled after a subregion of natural β-AP that is less than 15 amino acids in length and more preferably is between 3–10 amino acids in length. In various embodiments, the ACD is modeled after a subregion of β-AP that is 10, 9, 8, 7, 6, 5, 4 or 3 amino acids in length. In one embodiment, the subregion of β-AP upon which the ACD is modeled is an internal or carboxy-terminal region of β-AP (i.e., downstream of the amino-terminus at amino acid position 1). In another embodiment, the ACD is modeled after a subregion of β-AP that is hydrophobic. Preferred Aβ aggregation core domains encompass amino acid residues 17–20 or 17–21 of natural β-AP ($A\beta_{17-20}$ and $A\beta_{17-21}$, respectively). The amino acid sequences of $A\beta_{17-20}$ and $A\beta_{17-21}$ are Leu-Val-Phe-Phe (SEQ ID NO: 8) and Leu-Val-Phe-Phe-Ala (SEQ ID NO: 3), respectively.

As demonstrated in the Examples, D-amino acid-containing modulators designed based upon the amino acid sequences of $A\beta_{17-20}$ and $A\beta_{17-21}$ are particularly effective inhibitors of Aβ aggregation. These modulators can comprises a D-amino acid sequence corresponding to the L-amino acid sequence of $A\beta_{17-20}$ or $A\beta_{17-21}$, a D-amino acid sequence which is a retro-inverso isomer of the L-amino acid sequence of $A\beta_{17-20}$ or $A\beta_{17-21}$, or a D-amino acid sequence that is a scrambled or substituted version of the L-amino acid sequence of $A\beta_{17-20}$ or $A\beta_{17-21}$. The D-amino acid-based modulators may have unmodified amino- and/or carboxy-termini or, alternatively, the amino-terminus, the carboxy-terminus, or both, may be modified (described further below). The peptidic structures of effective modulators generally are hydrophobic and are characterized by the presence of at least two D-amino acid structures independently selected from the group consisting of a D-leucine structure, a D-phenylalanine structure and a D-valine structure. An used herein, the term a "D-amino acid structure" (such as a "D-leucine structure", a "D-phenylalanine structure" or a "D-valine structure") is intended to include the D-amino acid, as well as analogues, derivatives and mimetics of the D-amino acid that maintain the functional activity of the compound (discussed further below). For example, the term "D-phenylalanine structure" is intended to include D-phenylalanine as well as D-pyridylalanine and D-homophenylalanine. The term "D-leucine structure" is intended to include D-leucine, as well as substitution with D-valine or other natural or non-natural amino acid having an aliphatic side chain, such as D-norleucine. The term "D-valine structure" is intended to include D-valine, as well as substitution with D-leucine or other natural or non-natural amino acid having an aliphatic side chain.

In other embodiments, the peptidic structure of the modulator comprises at least two D-amino acid structures independently selected from the group consisting of a D-leucine structure, a D-phenylalanine structure, a D-valine structure, a D-alanine structure, a D-tyrosine structure and a D-iodotyrosine structure. In another embodiment, the peptidic structure is comprised of at least three D-amino acid structures independently selected from the group consisting of a D-leucine structure, a D-phenylalanine structure and a D-valine structure. In yet another embodiment, the peptidic structure is comprised of at least three D-amino acid structures independently selected from the group consisting of a D-leucine structure, a D-phenylalanine structure, a D-valine structure, a D-alanine structure, a D-tyrosine structure and a D-iodotyrosine structure. In yet another embodiment, the peptidic structure comprises at least four D-amino acid structures independently selected from the group consisting of a D-leucine structure, a D-phenylalanine structure and a D-valine structure. In yet another embodiment, the peptidic structure is comprised of at least four D-amino acid structures independently selected from the group consisting of a D-leucine structure, a D-phenylalanine structure and a D-valine structure. In a preferred embodiment, the peptidic structure includes a D-amino acid dipeptide selected from the group consisting of D-Phe-D-Phe, D-Phe-D-Tyr, D-Tyr-D-Phe, D-Phe-D-IodoTyr and D-IodoTyr-D-Phe.

In one embodiment, the invention provides a β-amyloid modulator compound comprising a formula (I):

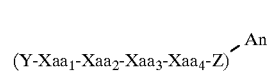

(I)

$$(Y\text{-}Xaa_1\text{-}Xaa_2\text{-}Xaa_3\text{-}Xaa_4\text{-}Z)\text{-}An$$

wherein $Xaa_1$, $Xaa_2$, $Xaa_3$ and $Xaa_4$ are each D-amino acid structures and at least two of $Xaa_1$, $Xaa_2$, $Xaa_3$ and $Xaa_4$ are, independently, selected from the group consisting of a D-leucine structure, a D-phenylalanine structure and a D-valine structure;

Y, which may or may not be present, is a structure having the formula $(Xaa)_a$, wherein Xaa is any D-amino acid structure and a is an integer from 1 to 15;

Z, which may or may not be present, is a structure having the formula $(Xaa)_b$, wherein Xaa is any D-amino acid structure and b is an integer from 1 to 15;

A, which may or may not be present, is a modifying group attached directly or indirectly to the compound; and n is an integer from 1 to 15;

wherein $Xaa_1$, $Xaa_2$, $Xaa_3$, $Xaa_4$, Y, Z, A and n are selected such that the compound binds to natural β-amyloid peptides or modulates the aggregation or inhibits the neurotoxicity of natural β-amyloid peptides when contacted with the natural β-amyloid peptides.

In a subembodiment of this formula, a fifth amino acid residue, $Xaa_5$, is specified C-terminal to $Xaa_4$ and Z, which may or may not be present, is a structure having the formula (Xaa)$_b$, wherein Xaa is any D-amino acid structure and b is an integer from 1 to 14. Accordingly, the invention provides a β-amyloid modulator compound comprising a formula (II):

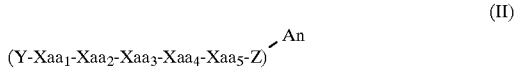

wherein b is an integer from 1 to 14.

In a preferred embodiment, Xaa$_1$, Xaa$_2$, Xaa$_3$, Xaa$_4$ of formula (I) are selected based on the sequence of Aβ$_{17-20}$, or acceptable substitutions thereof. Accordingly, in preferred embodiments, Xaa$_1$ is a D-alanine structure or a D-leucine structure, Xaa$_2$ is a D-valine structure, Xaa$_3$ is a D-phenylalanine structure, a D-tyrosine structure or a D-iodotyrosine structure and Xaa$_4$ is a D-phenylalanine structure, a D-tyrosine structure or a D-iodotyrosine structure.

In another preferred embodiment, Xaa$_1$, Xaa$_2$, Xaa$_3$, Xaa$_4$ and Xaa$_5$ of formula (II) are selected based on the sequence of Aβ$_{17-21}$, or acceptable substitutions thereof. Accordingly, in preferred embodiments, Xaa$_1$ is a D-alanine structure or a D-leucine structure, Xaa$_2$ is a D-valine structure, Xaa$_3$ is a D-phenylalanine structure, a D-tyrosine structure or a D-iodotyrosine structure, Xaa$_4$ is a D-phenylalanine structure, a D-tyrosine structure or a D-iodotyrosine structure, and Xaa$_5$ is a D-alanine structure or a D-leucine structure.

In another preferred embodiment, Xaa$_1$, Xaa$_2$, Xaa$_3$ and Xaa$_4$ of formula (I) are selected based on the retro-inverso isomer of Aβ$_{17-20}$, or acceptable substitutions thereof. Accordingly, in preferred embodiments, Xaa$_1$ is a D-alanine structure, a D-leucine structure or a D-phenylalanine structure, Xaa$_2$ is a D-phenylalanine structure, a D-tyrosine structure or a D-iodotyrosine structure, Xaa$_3$ is a D-phenylalanine structure, a D-tyrosine structure or a D-iodotyrosine structure and Xaa$_4$ is a D-valine structure or a D-leucine structure.

In another preferred embodiment, Xaa$_1$, Xaa$_2$, Xaa$_3$, Xaa$_4$ and Xaa$_5$ of formula (II) are selected based on the retroinverso isomer of Aβ$_{17-21}$, or acceptable substitutions thereof. Accordingly, in preferred embodiments, Xaa$_1$ is a D-alanine structure, a D-leucine structure or a D-phenylalanine structure, Xaa$_2$ is a D-phenylalanine structure, a D-tyrosine structure or a D-iodotyrosine structure, Xaa$_3$ is a D-phenylalanine structure, a D-tyrosine structure or a D-iodotyrosine structure, Xaa$_4$ is a D-valine structure or a D-leucine structure and Xaa$_5$ is a D-leucine structure.

In the modulators of the invention having the formula (I) or (II) shown above, an optional modifying group ("A") is attached directly or indirectly to the peptidic structure of the modulator. (As used herein, the term "modulating group" and "modifying group" are used interchangeably to describe a chemical group directly or indirectly attached to a peptidic structure). For example, a modifying group(s) can be directly attached by covalent coupling to the peptidic structure or a modifying group(s) can be attached indirectly by a stable non-covalent association. In one embodiment of the invention, a modifying group is attached to the amino-terminus of the peptidic structure of the modulator. Alternatively, in another embodiment of the invention, a modifying group is attached to the carboxy-terminus of the peptidic structure of the modulator. In yet another embodiment, a modulating group(s) is attached to the side chain of at least one amino acid residues of the peptidic structure of the modulator (e.g., through the epsilon amino group of a lysyl residue(s), through the carboxyl group of an aspartic acid residue(s) or a glutamic acid residue(s), through a hydroxy group of a tyrosyl residue(s), a serine residue(s) or a threonine residue(s) or other suitable reactive group on an amino acid side chain).

If a modifying group(s) is present, the modifying group is selected such that the compound inhibits aggregation of natural β-amyloid peptides when contacted with the natural β-amyloid peptides. Accordingly, since the β-AP peptide of the compound is modified from its natural state, the modifying group "A" as used herein is not intended to include hydrogen. In a modulator of the invention, a single modifying group may be attached to the peptidic structure or multiple modifying groups may be attached to the peptidic structure. The number of modifying groups is selected such that the compound inhibits aggregation of natural β-amyloid peptides when contacted with the natural β-amyloid peptides. However, n preferably is an integer between 1 and 60, more preferably between 1 and 30 and even more preferably between 1 and 10 or 1 and 5. In a preferred embodiment, A is an amino-terminal modifying group comprising a cyclic, heterocyclic, polycyclic or branched alkyl group and n=1. In another preferred embodiment, A is carboxy-terminally modifying group comprising an amide group, an alkyl amide group, an aryl amide group or a hydroxy group, and n=1. Suitable modifying groups are described further in subsections II and III below.

In another embodiment, the invention provides a β-amyloid modulator compound comprising a formula (III):

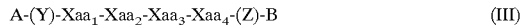

wherein Xaa$_1$, Xaa$_2$, Xaa$_3$ and Xaa$_4$ are each D-amino acid structures and at least two of Xaa$_1$, Xaa$_2$, Xaa$_3$ and Xaa$_4$ are, independently, selected from the group consisting of a D-leucine structure, a D-phenylalanine structure and a D-valine structure;

Y, which may or may not be present, is a peptidic structure having the formula (Xaa)$_a$, wherein Xaa is any amino acid structure and a is an integer from 1 to 15;

Z, which may or may not be present, is a peptidic structure having the formula (Xaa)$_b$, wherein Xaa is any amino acid structure and b is an integer from 1 to 15; and A, which may or may not be present, is a modifying group attached directly or indirectly to the amino terminus of the compound; and B, which may or may not be present, is a modifying group attached directly or indirectly to the carboxy terminus of the compound;

Xaa$_1$, Xaa$_2$, Xaa$_3$, Xaa$_4$, Y, Z, A and B being selected such that the compound binds to natural β-amyloid peptides or modulates the aggregation or inhibits the neurotoxicity of natural β-amyloid peptides when contacted with the natural β-amyloid peptides.

In a subembodiment of formula (III), a fifth amino acid residue, Xaa$_5$, is specified C-terminal to Xaa$_4$ and Z, which may or may not be present, is a structure having the formula (Xaa)$_b$, wherein Xaa is any D-amino acid structure and b is an integer from 1 to 14. Accordingly, the invention provides a β-amyloid modulator compound comprising a formula (IV):

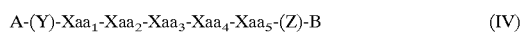

wherein b is an integer from 1 to 14.

In a preferred embodiment, $Xaa_1$, $Xaa_2$, $Xaa_3$, $Xaa_4$ of formula (III) are selected based on the sequence of $A\beta_{17-20}$, or acceptable substitutions thereof. Accordingly, in preferred embodiments, $Xaa_1$ is a D-alanine structure or a D-leucine structure, $Xaa_2$ is a D-valine structure, $Xaa_3$ is a D-phenylalanine structure, a D-tyrosine structure or a D-iodotyrosine structure and $Xaa_4$ is a D-phenylalanine structure, a D-tyrosine structure or a D-iodotyrosine structure.

In another preferred embodiment, $Xaa_1$, $Xaa_2$, $Xaa_3$, $Xaa_4$ and $Xaa_5$ of formula (IV) are selected based on the sequence of $A\beta_{17-21}$, or acceptable substitutions thereof. Accordingly, in preferred embodiments, $Xaa_1$ is a D-alanine structure or a D-leucine structure, $Xaa_2$ is a D-valine structure, $Xaa_3$ is a D-phenylalanine structure, a D-tyrosine structure or a D-iodotyrosine structure, $Xaa_4$ is a D-phenylalanine structure, a D-tyrosine structure or a D-iodotyrosine structure, and $Xaa_5$ is a D-alanine structure or a D-leucine structure.

In another preferred embodiment, $Xaa_1$, $Xaa_2$, $Xaa_3$ and $Xaa_4$ of formula (III) are selected based on the retro-inverso isomer of $A\beta_{17-20}$, or acceptable substitutions thereof. Accordingly, in preferred embodiments, $Xaa_1$ is a D-alanine structure, a D-leucine structure or a D-phenylalanine structure, $Xaa_2$ is a D-phenylalanine structure, a D-tyrosine structure or a D-iodotyrosine structure, $Xaa_3$ is a D-phenylalanine structure, a D-tyrosine structure or a D-iodotyrosine structure and $Xaa_4$ is a D-valine structure or a D-leucine structure.

In another preferred embodiment, $Xaa_1$, $Xaa_2$, $Xaa_3$, $Xaa_4$ and $Xaa_5$ of formula (IV) are selected based on the retro-inverso isomer of $A\beta_{17-21}$, or acceptable substitutions thereof. Accordingly, in preferred embodiments, $Xaa_1$ is a D-alanine structure, a D-leucine structure or a D-phenylalanine structure, $Xaa_2$ is a D-phenylalanine structure, a D-tyrosine structure or a D-iodotyrosine structure, $Xaa_3$ is a D-phenylalanine structure, a D-tyrosine structure or a D-iodotyrosine structure, $Xaa_4$ is a D-valine structure or a D-leucine structure and $Xaa_5$ is a D-leucine structure.

In one embodiment of the compounds of formulas (III) and/or (IV), A is present and comprises a cyclic, heterocyclic, polycyclic or branched alkyl group. In another embodiment of the compounds of formulas (III) and/or (IV), B is present and comprises an amide group, an alkyl amide group, an aryl amide group or a hydroxy group. In yet another embodiment of the compounds of formulas (III) and/or (IV), both A and B are present.

In preferred specific embodiments, the invention provides a β-amyloid modulator compound comprising a peptidic structure selected from the group consisting of D-Leu-D-Val-D-Phe-D-Phe (SEQ ID NO: 9), D-Leu-D-Val-D-Phe-phenethylamide (SEQ ID NO: 10), D-Leu-D-Val-D-Tyr-D-Phe (SEQ ID NO: 11), D-Leu-D-Val-D-IodoTyr-D-Phe (SEQ ID NO: 12), D-Leu-D-Val-D-Phe-D-Tyr (SEQ ID NO: 13), D-Leu-D-Val-D-Phe-D-IodoTyr (SEQ ID NO: 14), D-Leu-D-Val-D-Phe-D-Ala (SEQ ID NO: 15), D-Leu-D-Val-D-Phe-D-Phe-D-Ala (SEQ ID NO: 16), D-Ala-D-Val-D-Phe-D-Phe-D-Leu (SEQ ID NO: 17), D-Leu-D-Val-D-Tyr-D-Phe-D-Ala (SEQ ID NO: 18), D-Leu-D-Val-D-IodoTyr-D-Phe-D-Ala (SEQ ID NO: 19), D-Leu-D-Val-D-Phe-D-Tyr-D-Ala (SEQ ID NO: 20), D-Leu-D-Val-D-Phe-D-IodoTyr-D-Ala (SEQ ID NO: 21), D-Phe-D-Phe-D-Val-D-Leu (SEQ ID NO: 22), D-Ala-D-Phe-D-Phe-D-Val (SEQ ID NO: 23), D-Ala-D-Phe-D-Phe-D-Val-D-Leu (SEQ ID NO: 4), D-Ala-D-Phe-D-Phe-D-Leu-D-Leu (SEQ ID NO: 5), D-Leu-D-Phe-D-Phe-D-Val-D-Leu (SEQ ID NO: 6), D-Phe-D-Phe-D-Phe-D-Val-D-Leu (SEQ ID NO: 7), D-Phe-D-Phe-D-Phe-D-Leu-D-Val (SEQ ID NO: 24), D-Phe-D-Phe-D-Phe-D-Phe-D-Leu (SEQ ID NO: 25) and D-Ala-D-Phe-D-Phe-D-Phe-D-Leu (SEQ ID NO: 26). Any of the aforementioned specific peptidic structures can be amino-terminally and/or carboxy-terminally modified and described further in subsections II and/or III below.

Particularly preferred modulators comprise D-amino acid peptide amides designed based on the retro-inverso isomer of $A\beta_{17-21}$, or acceptable substitutions thereof, including compounds selected from the group consisting of D-Ala-D-Phe-D-Phe-D-Val-D-Leu-amide (SEQ ID NO: 4; C-terminal amide), D-Ala-D-Phe-D-Phe-D-Leu-D-Leu-amide (SEQ ID NO: 5; C-terminal amide), D-Leu-D-Phe-D-Phe-D-Val-D-Leu-amide (SEQ ID NO: 6; C-terminal amide) and D-Phe-D-Phe-D-Phe-D-Val-D-Leu-amide (SEQ ID NO: 7; C-terminal amide), D-Phe-D-Phe-D-Phe-D-Leu-D-Val-amide (SEQ ID NO: 24; C-terminal amide), D-Phe-D-Phe-D-Phe-D-Phe-D-Leu-amide (SEQ ID NO: 25; C-terminal amide) and D-Ala-D-Phe-D-Phe-D-Phe-D-Leu-amide (SEQ ID NO: 26; C-terminal amide).

The D-amino acid peptidic structures of the modulators of the invention are further intended to include other peptide modifications, including analogues, derivatives and mimetics, that retain the ability of the modulator to alter natural β-AP aggregation as described herein. For example, a D-amino acid peptidic structure of a modulator of the invention may be further modified to increase its stability, bioavailability, solubility, etc. The terms "analogue", "derivative" and "mimetic" as used herein are intended to include molecules which mimic the chemical structure of a D-peptidic structure and retain the functional properties of the D-peptidic structure. Approaches to designing peptide analogs, derivatives and mimetics are known in the art. For example, see Farmer, P. S. in *Drug Design* (E. J. Ariens, ed.) Academic Press, New York, 1980, vol. 10, pp. 119–143; Ball. J. B. and Alewood, P. F. (1990) *J. Mol. Recognition* 3:55; Morgan, B. A. and Gainor, J. A. (1989) *Ann. Rep. Med. Chem.* 24:243; and Freidinger, R. M. (1989) *Trends Pharmacol. Sci.* 10:270. See also Sawyer, T. K. (1995) "Peptidomimetic Design and Chemical Approaches to Peptide Metabolism" in Taylor, M. D. and Amidon, G. L. (eds.) *Peptide-Based Drug Design: Controlling Transport and Metabolism*, Chapter 17; Smith, A. B. 3rd, et al. (1995) *J. Am. Chem. Soc.* 117:11113–11123; Smith, A. B. 3rd, et al. (1994) *J. Am. Chem. Soc.* 116:9947–9962; and Hirschman, R., et al. (1993) *J. Am. Chem. Soc.* 115:12550–12568.

As used herein, a "derivative" of a compound X (e.g., a peptide or amino acid) refers to a form of X in which one or more reaction groups on the compound have been derivatized with a substituent group. Examples of peptide derivatives include peptides in which an amino acid side chain, the peptide backbone, or the amino- or carboxy-terminus has been derivatized (e.g., peptidic compounds with methylated amide linkages). As used herein an "analogue" of a compound X refers to a compound which retains chemical structures of X necessary for functional activity of X yet which also contains certain chemical structures which differ from X. An examples of an analogue of a naturally-occurring peptide is a peptide which includes one or more non-naturally-occurring amino acids. As used herein, a "mimetic" of a compound X refers to a compound in which chemical structures of X necessary for functional activity of X have been replaced with other chemical structures which mimic the conformation of X. Examples of peptidomimetics include peptidic compounds in which the peptide backbone is substituted with one or more benzodiazepine molecules (see e.g., James, G. L. et al. (1993) *Science* 260:1937–1942).

Analogues of the modulator compounds of the invention are intended to include compounds in which one or more D-amino acids of the peptidic structure are substituted with a homologous amino acid such that the properties of the original modulator are maintained. Preferably conservative amino acid substitutions are made at one or more amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine). Non-limiting examples of homologous substitutions that can be made in the peptidic structures of the modulators of the invention include substitution of D-phenylalanine with D-tyrosine, D-pyridylalanine or D-homophenylalanine, substitution of D-leucine with D-valine or other natural or non-natural amino acid having an aliphatic side chain and/or substitution of D-valine with D-leucine or other natural or non-natural amino acid having an aliphatic side chain.

The term mimetic, and in particular, peptidomimetic, is intended to include isosteres. The term "isostere" as used herein is intended to include a chemical structure that can be substituted for a second chemical structure because the steric conformation of the first structure fits a binding site specific for the second structure. The term specifically includes peptide back-bone modifications (i.e., amide bond mimetics) well known to those skilled in the art. Such modifications include modifications of the amide nitrogen, the α-carbon, amide carbonyl, complete replacement of the amide bond, extensions, deletions or backbone crosslinks. Several peptide backbone modifications are known, including ψ[CH$_2$S], ψ[CH$_2$NH], ψ[CSNH$_2$], ψ[NHCO], ψ[COCH$_2$], and ψ[(E) or (Z) CH=CH]. In the nomenclature used above, ψ indicates the absence of an amide bond. The structure that replaces the amide group is specified within the brackets.

Other possible modifications include an N-alkyl (or aryl) substitution (ψ[CONR]), or backbone crosslinking to construct lactams and other cyclic structures. Other derivatives of the modulator compounds of the invention include C-terminal hydroxymethyl derivatives, O-modified derivatives (e.g., C-terminal hydroxymethyl benzyl ether), N-terminally modified derivatives including substituted amides such as alkylamides and hydrazides and compounds in which a C-terminal phenylalanine residue is replaced with a phenethylamide analogue (e.g., Val-Phe-phenethylamide as an analogue of the tripeptide Val-Phe-Phe).

The modulator compounds of the invention can be incorporated into pharmaceutical compositions (described further in subsection V below) and can be used in detection and treatment methods as described further in subsection VI below.

II. Modifying Groups

In certain embodiments of the modulator compounds of the invention, a D-amino acid peptidic structure (such as an Aβ derived peptide, or an Aβ aggregation core domain, or an amino acid sequence corresponding to a rearranged Aβ aggregation core domain) is coupled directly or indirectly to at least one modifying group (abbreviated as MG). The term "modifying group" is intended to include structures that are directly attached to the D-amino acid peptidic structure (e.g., by covalent coupling), as well as those that are indirectly attached to the peptidic structure (e.g., by a stable non-covalent association or by covalent coupling to additional amino acid residues, or mimetics, analogues or derivatives thereof, which may flank the Aβ-derived D-amino acid peptidic structure). For example, the modifying group can be coupled to the amino-terminus or carboxy-terminus of an Aβ-derived D-amino acid peptidic structure, or to a peptidic or peptidomimetic region flanking the core domain. Alternatively, the modifying group can be coupled to a side chain of at least one D-amino acid residue of an Aβ-derived D-amino acid peptidic structure, or to a peptidic or peptidomimetic region flanking the core domain (e.g., through the epsilon amino group of a lysyl residue(s), through the carboxyl group of an aspartic acid residue(s) or a glutamic acid residue(s), through a hydroxy group of a tyrosyl residue(s), a serine residue(s) or a threonine residue(s) or other suitable reactive group on an amino acid side chain). Modifying groups covalently coupled to the D-amino acid peptidic structure can be attached by means and using methods well known in the art for linking chemical structures, including, for example, amide, alkylamino, carbamate, urea or ester bonds.

The term "modifying group" is intended to include groups that are not naturally coupled to natural Aβ peptides in their native form. Accordingly, the term "modifying group" is not intended to include hydrogen. The modifying group(s) is selected such that the modulator compound alters, and preferably inhibits, aggregation of natural β-amyloid peptides when contacted with the natural β-amyloid peptides or inhibits the neurotoxicity of natural β-amyloid peptides when contacted with the natural β-amyloid peptides. Although not intending to be limited by mechanism, in embodiments where the modulator comprises a modifying group(s), the modifying group(s) is thought to function as a key pharmacophore that enhances the ability of the modulator to disrupt Aβ polymerization.

In a preferred embodiment, the modifying group(s) comprises a cyclic, heterocyclic, polycyclic or branched alkyl group. The term "cyclic group", as used herein, is intended to include cyclic saturated or unsaturated (i.e., aromatic) group having from about 3 to 10, preferably about 4 to 8, and more preferably about 5 to 7, carbon atoms. Exemplary cyclic groups include cyclopropyl, cyclobutyl, cyclopentyl, cyclohexyl, and cyclooctyl. Cyclic groups may be unsubstituted or substituted at one or more ring positions. Thus, a cyclic group may be substituted with, e.g., halogens, alkyls, cycloalkyls, alkenyls, alkynyls, aryls, heterocycles, hydroxyls, aminos, nitros, thiols amines, imines, amides, phosphonates, phosphines, carbonyls, carboxyls, silyls, ethers, thioethers, sulfonyls, sulfonates, selenoethers, ketones, aldehydes, esters, —CF$_3$, —CN, or the like.

The term "heterocyclic group" is intended to include cyclic saturated or unsaturated (i.e., aromatic) group having from about 3 to 10, preferably about 4 to 8, and more preferably about 5 to 7, carbon atoms, wherein the ring structure includes about one to four heteroatoms. Heterocyclic groups include pyrrolidine, oxolane, thiolane, imidazole, oxazole, piperidine, piperazine, morpholine and pyridine. The heterocyclic ring can be substituted at one or more positions with such substituents as, for example, halogens, alkyls, cycloalkyls, alkenyls, alkynyls, aryls, other heterocycles, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, —CF$_3$, —CN, or the like. Heterocycles may also be bridged or fused to other cyclic groups as described below.

The term "polycyclic group" as used herein is intended to refer to two or more saturated or unsaturated (i.e., aromatic) cyclic rings in which two or more carbons are common to two adjoining rings, e.g., the rings are "fused rings". Rings that are joined through non-adjacent atoms are termed "bridged" rings. Each of the rings of the polycyclic group can be substituted with such substituents as described above, as for example, halogens, alkyls, cycloalkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, —CF$_3$, —CN, or the like.

A preferred polycyclic group is a group containing a cis-decalin structure. Although not intending to be limited by mechanism, it is thought that the "bent" conformation conferred on a modifying group by the presence of a cis-decalin structure contributes to the efficacy of the modifying group in disrupting Aβ polymerization. Accordingly, other structures which mimic the "bent" configuration of the cis-decalin structure can also be used as modifying groups. An example of a cis-decalin containing structure that can be used as a modifying group is a cholanoyl structure, such as a cholyl group. For example, a modulator compound can be modified at its amino terminus with a cholyl group by reacting the aggregation core domain with cholic acid, a bile acid. Moreover, a modulator compound can be modified at its carboxy terminus with a cholyl group according to methods known in the art (see e.g., Wess, G. et al. (1993) *Tetrahedron Letters,* 34:817–822; Wess, G. et al. (1992) *Tetrahedron Letters* 33:195–198; and Kramer, W. et al. (1992) *J. Biol. Chem.* 267:18598–18604). Cholyl derivatives and analogues can also be used as modifying groups. For example, a preferred cholyl derivative is Aic (3-(O-aminoethyl-iso)-cholyl), which has a free amino group that can be used to further modify the modulator compound (e.g., a chelation group for $^{99m}$Tc can be introduced through the free amino group of Aic). As used herein, the term "cholanoyl structure" is intended to include the cholyl group and derivatives and analogues thereof, in particular those which retain a four-ring cis-decalin configuration. Examples of cholanoyl structures include groups derived from other bile acids, such as deoxycholic acid, lithocholic acid, ursodeoxycholic acid, chenodeoxycholic acid and hyodeoxycholic acid, as well as other related structures such as cholanic acid, bufalin and resibufogenin (although the latter two compounds are not preferred for use as a modifying group). Another example of a cis-decalin containing compound is 5β-cholestan-3α-ol (the cis-decalin isomer of (+)-dihydrocholesterol). For further description of bile acid and steroid structure and nomenclature, see Nes, W. R. and McKean, M. L. *Biochemistry of Steroids and Other Isopentanoids*, University Park Press, Baltimore, Md., Chapter 2.

In addition to cis-decalin containing groups, other polycyclic groups may be used as modifying groups. For example, modifying groups derived from steroids or β-lactams may be suitable modifying groups. In one embodiment, the modifying group is a "biotinyl structure", which includes biotinyl groups and analogues and derivatives thereof (such as a 2-iminobiotinyl group). In another embodiment, the modifying group can comprise a "fluorescein-containing group", such as a group derived from reacting an Aβ-derived peptidic structure with 5-(and 6-)-carboxyfluorescein, succinimidyl ester or fluorescein isothiocyanate. In various other embodiments, the modifying group(s) can comprise an N-acetylneuraminyl group, a trans-4-cotininecarboxyl group, a 2-imino-1-imidazolidineacetyl group, an (S)-(−)-indoline-2-carboxyl group, a (−)-menthoxyacetyl group, a 2-norbornaneacetyl group, a γ-oxo-5-acenaphthenebutyryl, a (−)-2-oxo-4-thiazolidinecarboxyl group, a tetrahydro-3-furoyl group, a 2-iminobiotinyl group, a diethylenetriaminepentaacetyl group, a 4-morpholinecarbonyl group, a 2-thiopheneacetyl group or a 2-thiophenesulfonyl group.

In addition to the cyclic, heterocyclic and polycyclic groups discussed above, other types of modifying groups can be used in a modulator of the invention. For example, hydrophobic groups and branched alkyl groups may be suitable modifying groups. Examples include acetyl groups, phenylacetyl groups, phenylacetyl groups, diphenylacetyl groups, triphenylacetyl groups, isobutanoyl groups, 4-methylvaleryl groups, trans-cinnamoyl groups, butanoyl groups and 1-adamantanecarbonyl groups.

Yet another type of modifying group is a compound that contains a non-natural amino acid that acts as a beta-turn mimetic, such as a dibenzofuran-based amino acid described in Tsang, K. Y. et al. (1994) *J. Am. Chem. Soc.* 116:3988–4005; Diaz, H and Kelly, J. W. (1991) *Tetrahedron Letters* 41:5725–5728; and Diaz. H et al. (1992) *J. Am. Chem. Soc.* 114:8316–8318. An example of such a modifying group is a peptide-aminoethyldibenzofuranyl-proprionic acid (Adp) group (e.g., DDIIL-Adp) (SEQ ID NO: 31). This type of modifying group further can comprise one or more N-methyl peptide bonds to introduce additional steric hindrance to the aggregation of natural β-AP when compounds of this type interact with natural β-AP.

Non-limiting examples of suitable modifying groups, with their corresponding modifying reagents, are listed below:

| Modifying Group | Modifying Reagent |
|---|---|
| Cholyl- | Cholic acid |
| Lithocholyl- | Lithocholic acid |
| Hyodeoxycholyl- | Hyodeoxycholic acid |
| Chenodeoxycholyl- | Chenodeoxycholic acid |
| Ursodeoxycholyl- | Ursodeoxycholic acid |
| 3-Hydroxycinnamoyl- | 3-Hydroxycinnamic acid |
| 4-Hydroxycinnamoyl- | 4-Hydroxycinnamic acid |
| 2-Hydroxycinnamoyl- | 2-Hydroxycinnamic acid |
| 3-Hydroxy-4-methoxycinnamoyl- | 3-Hydroxy-4-methoxycinnamic acid |
| 4-Hydroxy-3-methoxycinnamoyl- | 4-Hydroxy-3-methoxycinnamic acid |
| 2-Carboxycinnamoyl- | 2-Carboxycinnamic acid |
| 3-Formylbenzoyl | 3-Carboxybenzaldehyde |
| 4-Formylbenzoyl | 4-Carboxybenzaldehyde |
| 3,4,-Dihydroxyhydrocinnamoyl- | 3,4,-Dihydroxyhydrocinnamic acid |
| 3,7-Dihydroxy-2-napthoyl- | 3,7-Dihydroxy-2-naphthoic acid |
| 4-Formylcinnamoyl- | 4-Formylcinnamic acid |
| 2-Formylphenoxyacetyl- | 2-Formylphenoxyacetic acid |
| 8-Formyl-1-napthoyl | 1,8-napthaldehydic acid |
| 4-(hydroxymethyl)benzoyl- | 4-(hydroxymethyl)benzoic acid |
| 4-Hydroxyphenylacetyl- | 4-Hydroxyphenylacetic acid |
| 3-Hydroxybenzoyl- | 3-Hydroxybenzoic acid |
| 4-Hydroxybenzoyl- | 4-Hydroxybenzoic acid |
| 5-Hydantoinacetyl- | 5-Hydantoinacetic acid |
| L-Hydroorotyl- | L-Hydroorotic acid |
| 4-Methylvaleryl- | 4-Methylvaleric acid |
| 2,4-Dihydroxybenzoyl- | 2,4-Dihydroxybenzoic acid |
| 3,4-Dihydroxycinnamoyl- | 3,4-Dihydroxycinnamic acid |
| 3,5-Dihydroxy-2-naphthoyl- | 3,5-Dihydroxy-2-naphthoic acid |
| 3-Benzoylpropanoyl- | 3-Benzoylpropanoic acid |
| trans-Cinnamoyl- | trans-Cinnamic acid |
| Phenylacetyl- | Phenylacetic acid |
| Diphenylacetyl- | Diphenylacetic acid |
| Triphenylacetyl- | Triphenylacetic acid |
| 2-Hydroxyphenylacetyl- | 2-Hydroxyphenylacetic acid |
| 3-Hydroxyphenylacetyl- | 3-Hydroxyphenylacetic acid |
| 4-Hydroxyphenylacetyl- | 4-Hydroxyphenylacetic acid |

-continued

| Modifying Group | Modifying Reagent |
| --- | --- |
| (±)-Mandelyl- | (±)-Mandelic acid |
| (±)-2,4-Dihydroxy-3,3-dimethylbutanoyl | (±)-Pantolactone |
| Butanoyl- | Butanoic anhydride |
| Isobutanoyl- | Isobutanoic anhydride |
| Hexanoyl- | Hexanoic anhydride |
| Propionyl- | Propionic anhydride |
| 3-Hydroxybutyroyl | β-Butyrolactone |
| 4-Hydroxybutyroyl | γ-Butyrolactone |
| 3-Hydroxypropionoyl | α-Propiolactone |
| 2,4-Dihydroxybutyroyl | 1-Hydroxy-β-Butyrolactone |
| 1-Adamantanecarbonyl- | 1-Adamantanecarbonic acid |
| Glycolyl- | Glycolic acid |
| DL-3-(4-hydroxyphenyl)lactyl- | DL-3-(4-hydroxyphenyl)lactic acid |
| 3-(2-Hydroxyphenyl)propionyl- | 3-(2-Hydroxyphenyl)propionic acid |
| 4-(2-Hydroxyphenyl)propionyl- | 4-(2-Hydroxyphenyl)propionic acid |
| D-3-Phenyllactyl- | D-3-Phenyllactic acid |
| Hydrocinnamoyl- | Hydrocinnamic acid |
| 3-(4-Hydroxyphenyl)propionyl- | 3-(4-Hydroxyphenyl)propionic acid |
| L-3-Phenyllactyl- | L-3-Phenyllactic acid |
| 4-methylvaleryl | 4-methylvaleric acid |
| 3-pyridylacetyl | 3-pyridylacetic acid |
| 4-pyridylacetyl | 4-pyridylacetic acid |
| Isonicotinoyl | |
| 4-quinolinecarboxyl | 4-quinolinecarboxylic acid |
| 1-isoquinolinecarboxyl | 1-isoquinolinecarboxylic acid |
| 3-isoquinolinecarboxyl | 3-isoquinolinecarboxylic acid |

Preferred modifying groups include cis-decalin-containing groups, biotin-containing groups, fluorescein-containing groups, a diethylene-triaminepentaacetyl group, a (−)-menthoxyacetyl group, an N-acetylneuraminyl group, a phenylacetyl group, a diphenylacetyl group, a triphenylacetyl group, an isobutanoyl group, a 4-methylvaleryl group, a 3-hydroxyphenylacetyl group, a 2-hydroxyphenylacetyl group, a 3,5-dihydroxy-2-naphthoyl group, a 3,4-dihydroxycinnamoyl group, a (±)-mandelyl group, a (±)-mandelyl-(±)-mandelyl group, a glycolyl group, a benzoylpropanoyl group and a 2,4-dihydroxybenzoyl group.

III. Additional Chemical Modifications of Aβ Modulators

A β-amyloid modulator compound of the invention can be further modified to alter the specific properties of the compound while retaining the ability of the compound to alter Aβ aggregation and inhibit Aβ neurotoxicity. For example, in one embodiment, the compound is further modified to alter a pharmacokinetic property of the compound, such as in vivo stability or half-life. In another embodiment, the compound is further modified to label the compound with a detectable substance. In yet another embodiment, the compound is further modified to couple the compound to an additional therapeutic moiety. Schematically, a modulator of the invention comprising a D-amino acid Aβ aggregation core domain coupled directly or indirectly to at least one modifying group can be illustrated as MG-ACD, whereas this compound which has been further modified to alter the properties of the modulator can be illustrated as MG-ACD-CM, wherein CM represents an additional chemical modification.

To further chemically modify the compound, such as to alter the pharmacokinetic properties of the compound, reactive groups can be derivatized. For example, when the modifying group is attached to the amino-terminal end of the aggregation core domain, the carboxy-terminal end of the compound can be further modified. Preferred C-terminal modifications include those which reduce the ability of the compound to act as a substrate for carboxypeptidases. Examples of preferred C-terminal modifiers include an amide group (i.e., a peptide amide), an alkyl or aryl amide group (e.g., an ethylamide group or a phenethylamide group) a hydroxy group (i.e., a peptide alcohol) and various non-natural amino acids, such as D-amino acids and β-alanine. Alternatively, when the modifying group is attached to the carboxy-terminal end of the aggregation core domain, the amino-terminal end of the compound can be further modified, for example, to reduce the ability of the compound to act as a substrate for aminopeptidases.

A modulator compound can be further modified to label the compound by reacting the compound with a detectable substance. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{14}C$, $^{123}I$, $^{124}I$, $^{125}I$, $^{131}I$, $^{99m}Tc$, $^{35}S$ or $^{3}H$. In a preferred embodiment, a modulator compound is radioactively labeled with $^{14}C$, either by incorporation of $^{14}C$ into the modifying group or one or more amino acid structures in the modulator compound. Labeled modulator compounds can be used to assess the in vivo pharmacokinetics of the compounds, as well as to detect Aβ aggregation, for example for diagnostic purposes. Aβ aggregation can be detected using a labeled modulator compound either in vivo or in an in vitro sample derived from a subject.

Preferably, for use as an in vivo diagnostic agent, a modulator compound of the invention is labeled with radioactive technetium or iodine. Accordingly, in one embodiment, the invention provides a modulator compound labeled with technetium, preferably $^{99m}Tc$. Methods for labeling peptide compounds with technetium are known in the art (see e.g., U.S. Pat. Nos. 5,443,815, 5,225,180 and 5,405,597, all by Dean et al.; Stepniak-Biniakiewicz, D., et al. (1992) J. Med. Chem. 35:274–279; Fritzberg, A. R., et al. (1988) Proc. Natl. Acad. Sci. USA 85:4025–4029; Baidoo, K. E., et al. (1990) Cancer Res. Suppl. 50:799s–803s; and Regan, L. and Smith, C. K. (1995) Science 270:980–982). A modifying group can be chosen that provides a site at which a chelation group for $^{99m}Tc$ can be introduced, such as the Aic derivative of cholic acid, which has a free amino group. In another embodiment, the invention provides a modulator compound labeled with radioactive iodine. For example, a phenylalanine residue within the Aβ sequence (such as $Phe_{19}$ or $Phe_{20}$) can be substituted with radioactive iodotyrosyl. Any of the various isotopes of radioactive iodine can be incorporated to create a diagnostic agent. Preferably, $^{123}I$ (half-life=13.2 hours) is used for whole body scintigraphy, $^{124}I$ (half life=4 days) is used for positron emission tomography (PET), $^{125}I$ (half life=60 days) is used for metabolic turnover studies and $^{131}I$ (half life=8 days) is used for whole body counting and delayed low resolution imaging studies.

Furthermore, an additional modification of a modulator compound of the invention can serve to confer an additional therapeutic property on the compound. That is, the additional chemical modification can comprise an additional functional moiety. For example, a functional moiety which serves to break down or dissolve amyloid plaques can be coupled to the modulator compound. In this form, the MG-ACD portion of the modulator serves to target the compound to Aβ peptides and disrupt the polymerization of the Aβ peptides, whereas the additional functional moiety serves to break down or dissolve amyloid plaques after the compound has been targeted to these sites.

In an alternative chemical modification, a β-amyloid compound of the invention is prepared in a "prodrug" form, wherein the compound itself does not modulate Aβ aggregation, but rather is capable of being transformed, upon metabolism in vivo, into a β-amyloid modulator compound as defined herein. For example, in this type of compound, the modulating group can be present in a prodrug form that is capable of being converted upon metabolism into the form of an active modulating group. Such a prodrug form of a modifying group is referred to herein as a "secondary modifying group." A variety of strategies are known in the art for preparing peptide prodrugs that limit metabolism in order to optimize delivery of the active form of the peptide-based drug (see e.g., Moss, J. (1995) in *Peptide-Based Drug Design: Controlling Transport and Metabolism*, Taylor, M. D. and Amidon, G. L. (eds), Chapter 18. Additionally strategies have been specifically tailored to achieving CNS delivery based on "sequential metabolism" (see e.g., Bodor, N., et al. (1992) *Science* 257:1698–1700; Prokai, L., et al. (1994) *J. Am. Chem. Soc.* 116:2643–2644; Bodor, N. and Prokai, L. (1995) in *Peptide-Based Drug Design: Controlling Transport and Metabolism*, Taylor, M. D. and Amidon, G. L. (eds), Chapter 14. In one embodiment of a prodrug form of a modulator of the invention, the modifying group comprises an alkyl ester to facilitate blood-brain barrier permeability.

Modulator compounds of the invention can be prepared by standard techniques known in the art. The peptide component of a modulator can be synthesized using standard techniques such as those described in Bodansky, M. *Principles of Peptide Synthesis*, Springer Verlag, Berlin (1993) and Grant, G. A (ed.). *Synthetic Peptides: A User's Guide*, W. H. Freeman and Company, New York (1992). Automated peptide synthesizers are commercially available (e.g., Advanced ChemTech Model 396; Milligen/Biosearch 9600). Additionally, one or more modulating groups can be attached to the Aβ-derived peptidic component (e.g., an Aβ aggregation core domain) by standard methods, for example using methods for reaction through an amino group (e.g., the alpha-amino group at the amino-terminus of a peptide), a carboxyl group (e.g., at the carboxy terminus of a peptide), a hydroxyl group (e.g., on a tyrosine, serine or threonine residue) or other suitable reactive group on an amino acid side chain (see e.g., Greene, T. W and Wuts, P. G. M. *Protective Groups in Organic Synthesis*, John Wiley and Sons, Inc., New York (1991). Exemplary syntheses of D-amino acid β amyloid modulator are described further in Example 1.

IV. Screening Assays

Another aspect of the invention pertains to a method for selecting a modulator of β-amyloid aggregation. In the method, a test compound is contacted with natural β amyloid peptides, the aggregation of the natural β-AP is measured and a modulator is selected based on the ability of the test compound to alter the aggregation of the natural β-AP (e.g., inhibit or promote aggregation). In a preferred embodiment, the test compound is contacted with a molar excess amount of the natural β-AP. The amount and/or rate of natural β-AP aggregation in the presence of the test compound can be determined by a suitable assay indicative of β-AP aggregation, as described herein (see e.g., Example 2).

In a preferred assay, the natural β-AP is dissolved in solution in the presence of the test compound and aggregation of the natural β-AP is assessed in a nucleation assay (see Example 2) by assessing the turbidity of the solution over time, as measured by the apparent absorbance of the solution at 405 nm (described further in Example 2; see also Jarrett et al. (1993) *Biochemistry* 32:4693–4697). In the absence of a β-amyloid modulator, the $A_{405\ nm}$ of the solution typically stays relatively constant during a lag time in which the β-AP remains in solution, but then the $A_{405\ nm}$ of the solution rapidly increases as the β-AP aggregates and comes out of solution, ultimately reaching a plateau level (i.e., the $A_{405\ nm}$ of the solution exhibits sigmoidal kinetics over time). In contrast, in the presence of a test compound that inhibits β-AP aggregation, the $A_{405\ nm}$ of the solution is reduced compared to when the modulator is absent. Thus, in the presence of the inhibitory modulator, the solution may exhibit an increased lag time, a decreased slope of aggregation and/or a lower plateau level compared to when the modulator is absent. This method for selecting a modulator of β-amyloid polymerization can similarly be used to select modulators that promote β-AP aggregation. Thus, in the presence of a modulator that promotes β-AP aggregation, the $A_{405\ nm}$ of the solution is increased compared to when the modulator is absent (e.g., the solution may exhibit an decreased lag time, increase slope of aggregation and/or a higher plateau level compared to when the modulator is absent).

Another assay suitable for use in the screening method of the invention, a seeded extension assay, is also described further in Example 2. In this assay, β-AP monomer and an aggregated β-AP "seed" are combined, in the presence and absence of a test compound, and the amount of β-fibril formation is assayed based on enhanced emission of the dye Thioflavine T when contacted with β-AP fibrils. Moreover, β-AP aggregation can be assessed by electron microscopy (EM) of the β-AP preparation in the presence or absence of the modulator. For example, β amyloid fibril formation, which is detectable by EM, is reduced in the presence of a modulator that inhibits β-AP aggregation (i.e., there is a reduced amount or number of β-fibrils in the presence of the modulator), whereas β fibril formation is increased in the presence of a modulator that promotes β-AP aggregation (i.e., there is an increased amount or number of β-fibrils in the presence of the modulator).

Another preferred assay for use in the screening method of the invention to select suitable modulators is the neurotoxicity assay described in Example 3. Compounds are selected which inhibit the formation of neurotoxic Aβ aggregates and/or which inhibit the neurotoxicity of preformed Aβ fibrils. This neurotoxicity assay is considered to be predictive of neurotoxicity in vivo. Accordingly, inhibitory activity of a modulator compound in the in vitro neurotoxicity assay is predictive of similar inhibitory activity of the compound for neurotoxicity in vivo.

V. Pharmaceutical Compositions

Another aspect of the invention pertains to pharmaceutical compositions of the β-amyloid modulator compounds of the invention. In one embodiment, the composition includes a β amyloid modulator compound in a therapeutically or prophylactically effective amount sufficient to alter, and preferably inhibit, aggregation of natural β-amyloid peptides, and a pharmaceutically acceptable carrier. In another embodiment, the composition includes a β amyloid modulator compound in a therapeutically or prophylactically effective amount sufficient to inhibit the neurotoxicity of natural β-amyloid peptides, and a pharmaceutically acceptable carrier. A "therapeutically effective amount" refers to an amount effective, at dosages and for periods of time necessary, to achieve the desired therapeutic result, such as reduction or reversal or β-amyloid deposition and/or reduction or reversal of Aβ neurotoxicity. A therapeutically effective amount of modulator may vary according to factors such as the disease state, age, sex, and weight of the individual, and the ability of the modulator to elicit a desired response in the individual. Dosage regimens may be adjusted to provide the optimum therapeutic response. A therapeutically effective amount is also one in which any toxic or detrimental effects of the modulator are outweighed by the therapeutically beneficial effects. The potential neurotoxicity of the modulators of the invention can be assayed using the cell-based assay described in Example 6 and a therapeutically effective modulator can be selected which does not exhibit significant neurotoxicity. In a preferred embodiment, a therapeutically effective amount of a modulator is sufficient to alter, and preferably inhibit, aggregation of a molar excess amount of natural β-amyloid peptides. A "prophylactically effective amount" refers to an amount effective, at dosages and for periods of time necessary, to achieve the desired prophylactic result, such as preventing or inhibiting the rate of β-amyloid deposition and/or Aβ neurotoxicity in a subject predisposed to β-amyloid deposition. A prophylactically effective amount can be determined as described above for the therapeutically effective amount. Typically, since a prophylactic dose is used in subjects prior to or at an earlier stage of disease, the prophylactically effective amount will be less than the therapeutically effective amount.

One factor that may be considered when determining a therapeutically or prophylactically effective amount of a β amyloid modulator is the concentration of natural β-AP in a biological compartment of a subject, such as in the cerebrospinal fluid (CSF) of the subject. The concentration of natural β-AP in the CSF has been estimated at 3 nM (Schwartzman, (1994) *Proc. Natl. Acad. Sci. USA* 91:8368–8372). A non-limiting range for a therapeutically or prophylactically effective amounts of a β amyloid modulator is 0.01 nM–10 μM. It is to be noted that dosage values may vary with the severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The amount of active compound in the composition may vary according to factors such as the disease state, age, sex, and weight of the individual, each of which may affect the amount of natural β-AP in the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

As used herein "pharmaceutically acceptable carrier" includes any and all solvents, dispersion media, coatings, antibacterial and antifungal agents, isotonic and absorption delaying agents, and the like that are physiologically compatible. In one embodiment, the carrier is suitable for parenteral administration. Preferably, the carrier is suitable for administration into the central nervous system (e.g., intraspinally or intracerebrally). Alternatively, the carrier can be suitable for intravenous, intraperitoneal or intramuscular administration. In another embodiment, the carrier is suitable for oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as manitol, sorbitol, or sodium chloride in the composition. Prolonged absorption of the injectable compositions can be brought about by including in the composition an agent which delays absorption, for example, monostearate salts and gelatin. Moreover, the modulators can be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Sterile injectable solutions can be prepared by incorporating the active compound (e.g., β-amyloid modulator) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

A modulator compound of the invention can be formulated with one or more additional compounds that enhance the solubility of the modulator compound. Preferred compounds to be added to formulations to enhance the solubility of the modulators are cyclodextrin derivatives, preferably hydroxypropyl-γ-cyclodextrin. Drug delivery vehicles containing a cyclodextrin derivative for delivery of peptides to the central nervous system are described in Bodor, N., et al. (1992) *Science* 257:1698–1700. For the β-amyloid modulators described herein, inclusion in the formulation of hydroxypropyl-γ-cyclodextrin at a concentration 50–200 mM increases the aqueous solubility of the compounds. In addition to increased solubility, inclusion of a cyclodextrin derivative in the formulation may have other beneficial effects, since β-cyclodextrin itself has been reported to interact with the Aβ peptide and inhibit fibril formation in vitro (Camilleri, P., et al. (1994) *FEBS Letters* 341:256–258. Accordingly, use of a modulator compound of the invention in combination with a cyclodextrin derivative may result in greater inhibition of Aβ aggregation than use of the modulator alone. Chemical modifications of cyclodextrins are known in the art (Hanessian, S., et al. (1995) J. Org. Chem. 60:4786–4797). In addition to use as an additive in a pharmaceutical composition containing a modulator of the invention, cyclodextrin derivatives may also be useful as modifying groups and, accordingly, may also be covalently coupled to an Aβ peptide compound to form a modulator compound of the invention.

Another preferred formulation for the modulator compounds to enhance brain uptake comprises the detergent Tween-80, polyethylene glycol (PEG) and ethanol in a saline solution. A non-limiting example of such a preferred formulation is 0.16% Tween-80, 1.3% PEG-3000 and 2% ethanol in saline.

In another embodiment, a pharmaceutical composition comprising a modulator of the invention is formulated such that the modulator is transported across the blood-brain barrier (BBB). Various strategies known in the art for increasing transport across the BBB can be adapted to the modulators of the invention to thereby enhance transport of the modulators across the BBB (for reviews of such strategies, see e.g., Pardridge, W. M. (1994) *Trends in Biotechnol.* 12:239–245; Van Bree, J. B. et al. (1993) *Pharm. World Sci.* 15:2–9; and Pardridge, W. M. et al. (1992) *Pharmacol. Toxicol.* 71:3–10). In one approach, the modulator is chemically modified to form a prodrug with enhanced transmembrane transport. Suitable chemical modifications include covalent linking of a fatty acid to the modulator through an amide or ester linkage (see e.g., U.S. Pat. No. 4,933,324 and PCT Publication WO 89/07938, both by Shashoua; U.S. Pat. No. 5,284,876 by Hesse et al.; Toth, I. et al. (1994) *J. Drug Target.* 2:217–239; and Shashoua, V. E. et al. (1984) *J. Med. Chem.* 27:659–664) and glycating the modulator (see e.g., U.S. Pat. No. 5,260,308 by Poduslo et al.). Also, N-acylamino acid derivatives may be used in a modulator to form a "lipidic" prodrug (see e.g., U.S. Pat. No. 5,112,863 by Hashimoto et al.).

In another approach for enhancing transport across the BBB, a peptidic or peptidomimetic modulator is conjugated to a second peptide or protein, thereby forming a chimeric protein, wherein the second peptide or protein undergoes absorptive-mediated or receptor-mediated transcytosis through the BBB. Accordingly, by coupling the modulator to this second peptide or protein, the chimeric protein is transported across the BBB. The second peptide or protein can be a ligand for a brain capillary endothelial cell receptor ligand. For example, a preferred ligand is a monoclonal antibody that specifically binds to the transferrin receptor on brain capillary endothelial cells (see e.g., U.S. Pat. Nos. 5,182,107 and 5,154,924 and PCT Publications WO 93/10819 and WO 95/02421, all by Friden et al.). Other suitable peptides or proteins that can mediate transport across the BBB include histones (see e.g., U.S. Pat. No. 4,902,505 by Pardridge and Schimmel) and ligands such as biotin, folate, niacin, pantothenic acid, riboflavin, thiamin, pryridoxal and ascorbic acid (see e.g., U.S. Pat. Nos. 5,416, 016 and 5,108,921, both by Heinstein). Additionally, the glucose transporter GLUT-1 has been reported to transport glycopeptides (L-serinyl-β-D-glucoside analogues of [Met5]enkephalin) across the BBB (Polt, R. et al. (1994) *Proc. Natl. Acad. Sci. USA* 91:7114–1778). Accordingly, a modulator compound can be coupled to such a glycopeptide to target the modulator to the GLUT-1 glucose transporter. For example, a modulator compound which is modified at its amino terminus with the modifying group Aic (3-(O-aminoethyl-iso)-cholyl, a derivative of cholic acid having a free amino group) can be coupled to a glycopeptide through the amino group of Aic by standard methods. Chimeric proteins can be formed by recombinant DNA methods (e.g., by formation of a chimeric gene encoding a fusion protein) or by chemical crosslinking of the modulator to the second peptide or protein to form a chimeric protein. Numerous chemical crosslinking agents are known in the (e.g., commercially available from Pierce, Rockford Ill.). A crosslinking agent can be chosen which allows for high yield coupling of the modulator to the second peptide or protein and for subsequent cleavage of the linker to release bioactive modulator. For example, a biotin-avidin-based linker system may be used.

In yet another approach for enhancing transport across the BBB, the modulator is encapsulated in a carrier vector which mediates transport across the BBB. For example, the modulator can be encapsulated in a liposome, such as a positively charged unilamellar liposome (see e.g., PCT Publications WO 88/07851 and WO 88/07852, both by Faden) or in polymeric microspheres (see e.g., U.S. Pat. No. 5,413,797 by Khan et al., U.S. Pat. No. 5,271,961 by Mathiowitz et al. and U.S. Pat. No. 5,019,400 by Gombotz et al.). Moreover, the carrier vector can be modified to target it for transport across the BBB. For example, the carrier vector (e.g., liposome) can be covalently modified with a molecule which is actively transported across the BBB or with a ligand for brain endothelial cell receptors, such as a monoclonal antibody that specifically binds to transferrin receptors (see e.g., PCT Publications WO 91/04014 by Collins et al. and WO 94/02178 by Greig et al.).

In still another approach to enhancing transport of the modulator across the BBB, the modulator is coadministered with another agent which functions to permeabilize the BBB. Examples of such BBB "permeabilizers" include bradykinin and bradykinin agonists (see e.g., U.S. Pat. No. 5,112,596 by Malfroy-Camine) and peptidic compounds disclosed in U.S. Pat. No. 5,268,164 by Kozarich et al.

Assays that measure the in vitro stability of the modulator compounds in cerebrospinal fluid (CSF) and the degree of brain uptake of the modulator compounds in animal models can be used as predictors of in vivo efficacy of the compounds. Suitable assays for measuring CSF stability and brain uptake are described in Examples 7 and 8, respectively.

A modulator compound of the invention can be formulated into a pharmaceutical composition wherein the modulator is the only active compound or, alternatively, the pharmaceutical composition can contain additional active compounds. For example, two or more modulator compounds may be used in combination. Moreover, a modulator compound of the invention can be combined with one or more other agents that have anti-amyloidogenic properties. For example, a modulator compound can be combined with the non-specific cholinesterase inhibitor tacrine (COGNEX®, Parke-Davis).

In another embodiment, a pharmaceutical composition of the invention is provided as a packaged formulation. The packaged formulation may include a pharmaceutical composition of the invention in a container and printed instructions for administration of the composition for treating a subject having a disorder associated with β-amyloidosis, e.g. Alzheimer's disease.

VI. Methods of Using Aβ Modulators

Another aspect of the invention pertains to methods for altering the aggregation or inhibiting the neurotoxicity of natural β-amyloid peptides. In the methods of the invention, natural β amyloid peptides are contacted with a β amyloid modulator such that the aggregation of the natural β amyloid peptides is altered or the neurotoxicity of the natural β amyloid peptides is inhibited. In a preferred embodiment, the modulator inhibits aggregation of the natural β amyloid peptides. In another embodiment, the modulator promotes aggregation of the natural β amyloid peptides. Preferably, aggregation of a molar excess amount of β-AP, relative to the amount of modulator, is altered upon contact with the modulator.

In the method of the invention, natural β amyloid peptides can be contacted with a modulator either in vitro or in vivo. Thus, the term "contacted with" is intended to encompass both incubation of a modulator with a natural β-AP preparation in vitro and delivery of the modulator to a site in vivo where natural β-AP is present. Since the modulator compound interacts with natural β-AP, the modulator compounds can be used to detect natural β-AP, either in vitro or in vivo. Accordingly, one use of the modulator compounds of the invention is as diagnostic agents to detect the presence of natural β-AP, either in a biological sample or in vivo in a subject. Furthermore, detection of natural β-AP utilizing a modulator compound of the invention further can be used to diagnose amyloidosis in a subject. Additionally, since the modulator compounds of the invention disrupt β-AP aggregation and inhibit β-AP neurotoxicity, the modulator compounds also are useful in the treatment of disorders associated with β-amyloidosis, either prophylactically or therapeutically. Accordingly, another use of the modulator compounds of the invention is as therapeutic agents to alter aggregation and/or neurotoxicity of natural β-AP.

In one embodiment, a modulator compound of the invention is used in vitro, for example to detect and quantitate natural β-AP in sample (e.g., a sample of biological fluid). To aid in detection, the modulator compound can be modified with a detectable substance. The source of natural β-AP used in the method can be, for example, a sample of cerebrospinal fluid (e.g., from an AD patient, an adult susceptible to AD due to family history, or a normal adult). The natural β-AP sample is contacted with a modulator of the invention and aggregation of the β-AP is measured, such as by the assays described in Example 2. The degree of aggregation of the β-AP sample can then be compared to that of a control sample(s) of a known concentration of β-AP, similarly contacted with the modulator and the results can be used as an indication of whether a subject is susceptible to or has a disorder associated with β-amyloidosis. Moreover, β-AP can be detected by detecting a modulating group incorporated into the modulator. For example, modulators incorporating a biotin compound as described herein (e.g., an amino-terminally biotinylated β-AP peptide) can be detected using a probe which or avidin probe which is labeled with a detectable substance (e.g., an enzyme, such as peroxidase).

In another embodiment, a modulator compound of the invention is used in vivo to detect, and, if desired, quantitate, natural β-AP deposition in a subject, for example to aid in the diagnosis of β amyloidosis in the subject. To aid in detection, the modulator compound can be modified with a detectable substance, preferably $^{99m}$Tc or radioactive iodine (described further above), which can be detected in vivo in a subject. The labeled β-amyloid modulator compound is administered to the subject and, after sufficient time to allow accumulation of the modulator at sites of amyloid deposition, the labeled modulator compound is detected by standard imaging techniques. The radioactive signal generated by the labeled compound can be directly detected (e.g., whole body counting), or alternatively, the radioactive signal can be converted into an image on an autoradiograph or on a computer screen to allow for imaging of amyloid deposits in the subject. Methods for imaging amyloidosis using radiolabeled proteins are known in the art. For example, serum amyloid P component (SAP), radiolabeled with either $^{123}$I or $^{99m}$Tc, has been used to image systemic amyloidosis (see e.g., Hawkins, P. N. and Pepys, M. B. (1995) *Eur. J. Nucl. Med.* 22:595–599). Of the various isotypes of radioactive iodine, preferably $^{123}$I (half-life=13.2 hours) is used for whole body scintigraphy, 124I (half life=4 days) is used for positron emission tomography (PET), $^{125}$I (half life=60 days) is used for metabolic turnover studies and $^{131}$I (half life=8 days) is used for whole body counting and delayed low resolution imaging studies. Analogous to studies using radiolabeled SAP, a labeled modulator compound of the invention can be delivered to a subject by an appropriate route (e.g., intravenously, intraspinally, intracerebrally) in a single bolus, for example containing 100 μg of labeled compound carrying approximately 180 MBq of radioactivity.

The invention provides a method for detecting the presence or absence of natural β-amyloid peptides in a biological sample, comprising contacting a biological sample with a compound of the invention and detecting the compound bound to natural β-amyloid peptides to thereby detect the presence or absence of natural β-amyloid peptides in the biological sample. In one embodiment, the β-amyloid modulator compound and the biological sample are contacted in vitro. In another embodiment, the β-amyloid modulator compound is contacted with the biological sample by administering the β-amyloid modulator compound to a subject. For in vivo administration, preferably the compound is labeled with radioactive technetium or radioactive iodine.

The invention also provides a method for detecting natural β-amyloid peptides to facilitate diagnosis of a β-amyloidogenic disease, comprising contacting a biological sample with the compound of the invention and detecting the compound bound to natural β-amyloid peptides to facilitate diagnosis of a β-amyloidogenic disease. In one embodiment, the β-amyloid modulator compound and the biological sample are contacted in vitro. In another embodiment, the β-amyloid modulator compound is contacted with the biological sample by administering the β-amyloid modulator compound to a subject. For in vivo administration, preferably the compound is labeled with radioactive technetium or radioactive iodine. Preferably, use of the method facilitates diagnosis of Alzheimer's disease.

In another embodiment, the invention provides a method for altering natural β-AP aggregation or inhibiting β-AP neurotoxicity, which can be used prophylactically or therapeutically in the treatment or prevention of disorders associated with β amyloidosis, e.g., Alzheimer's Disease. Modulator compounds of the invention can reduce the toxicity of natural β-AP aggregates to cultured neuronal cells. Moreover, the modulators also have the ability to reduce the neurotoxicity of preformed Aβ fibrils. Accordingly, the modulator compounds of the invention can be used to inhibit or prevent the formation of neurotoxic Aβ fibrils in subjects (e.g., prophylactically in a subject predisposed to β-amyloid deposition) and can be used to reverse β-amyloidosis therapeutically in subjects already exhibiting β-amyloid deposition.

A modulator of the invention is contacted with natural β amyloid peptides present in a subject (e.g., in the cerebrospinal fluid or cerebrum of the subject) to thereby alter the aggregation of the natural β-AP and/or inhibit the neurotoxicity of the natural β-APs. A modulator compound alone can be administered to the subject, or alternatively, the modulator compound can be administered in combination with other therapeutically active agents (e.g., as discussed above in subsection IV). When combination therapy is employed, the therapeutic agents can be coadministered in a single pharmaceutical composition, coadministered in separate pharmaceutical compositions or administered sequentially.

The modulator may be administered to a subject by any suitable route effective for inhibiting natural β-AP aggregation in the subject, although in a particularly preferred embodiment, the modulator is administered parenterally, most preferably to the central nervous system of the subject. Possible routes of CNS administration include intraspinal administration and intracerebral administration (e.g., intracerebrovascular administration). Alternatively, the compound can be administered, for example, orally, intraperitoneally, intravenously or intramuscularly. For non-CNS administration routes, the compound can be administered in a formulation which allows for transport across the BBB. Certain modulators may be transported across the BBB without any additional further modification whereas others may need further modification as described above in subsection IV.

Suitable modes and devices for delivery of therapeutic compounds to the CNS of a subject are known in the art, including cerebrovascular reservoirs (e.g., Ommaya or Rikker reservoirs; see e.g., Raney, J. P. et al. (1988) *J. Neurosci. Nurs.* 20:23–29; Sundaresan, N. et al. (1989) *Oncology* 3:15–22), catheters for intrathecal delivery (e.g., Port-a-Cath, Y-catheters and the like; see e.g., Plummer, J. L. (1991) *Pain* 44:215–220; Yaksh, T. L. et al. (1986) *Pharmacol. Biochem. Behav.* 25:483–485), injectable intrathecal reservoirs (e.g., Spinalgesic; see e.g., Brazenor, G. A. (1987) *Neurosurgery* 21:484–491), implantable infusion pump systems (e.g., Infusaid; see e.g., Zierski, J. et al. (1988) *Acta Neurochem. Suppl.* 43:94–99; Kanoff, R. B. (1994) *J. Am. Osteopath. Assoc.* 94:487–493) and osmotic pumps (sold by Alza Corporation). A particularly preferred mode of administration is via an implantable, externally programmable infusion pump. Suitable infusion pump systems and reservoir systems are also described in U.S. Pat. No. 5,368,562 by Blomquist and U.S. Pat. No. 4,731,058 by Doan, developed by Pharmacia Deltec Inc.

The method of the invention for altering β-AP aggregation in vivo, and in particular for inhibiting β-AP aggregation, can be used therapeutically in diseases associated with abnormal β amyloid aggregation and deposition to thereby slow the rate of β amyloid deposition and/or lessen the degree of β amyloid deposition, thereby ameliorating the course of the disease. In a preferred embodiment, the method is used to treat Alzheimer's disease (e.g., sporadic or familial AD, including both individuals exhibiting symptoms of AD and individuals susceptible to familial AD). The method can also be used prophylactically or therapeutically to treat other clinical occurrences of β amyloid deposition, such as in Down's syndrome individuals and in patients with hereditary cerebral hemorrhage with amyloidosis-Dutch-type (HCHWA-D). While inhibition of β-AP aggregation is a preferred therapeutic method, modulators that promote β-AP aggregation may also be useful therapeutically by allowing for the sequestration of β-AP at sites that do not lead to neurological impairment.

Additionally, abnormal accumulation of β-amyloid precursor protein in muscle fibers has been implicated in the pathology of sporadic inclusion body myositis (IBM) (Askana, V. et al. (1996) *Proc. Natl. Acad. Sci. USA* 93:1314–1319; Askanas, V. et al. (1995) *Current Opinion in Rheumatology* 7:486–496). Accordingly, the modulators of the invention can be used prophylactically or therapeutically in the treatment of disorders in which β-AP, or APP, is abnormally deposited at non-neurological locations, such as treatment of IBM by delivery of the modulators to muscle fibers.

This invention is further illustrated by the following examples which should not be construed as limiting. A modulator's ability to alter the aggregation of natural β-amyloid peptide and/or inhibit the neurotoxicity of natural β-amyloid peptide in the assays described below are predictive of the modulator's ability to perform the same function in vivo. The contents of all references, patents and published patent applications cited throughout this application are hereby incorporated by reference.

EXAMPLE 1

Preparation of β-Amyloid Modulator Compounds Comprising D-Amino Acids

β-amyloid modulators comprising D-amino acids can be prepared by solid-phase peptide synthesis, for example using an $N^{\alpha}$-9-fluorenylmethyloxycarbonyl (FMOC)-based protection strategy as follows. Starting with 2.5 mmoles of FMOC-D-Val-Wang resin, sequential additions of each amino acid are performed using a four-fold excess of protected amino acids, 1-hydroxybenzotriazole (HOBt) and diisopropyl carbodiimide (DIC). Recouplings are performed when necessary as determined by ninhydrin testing of the resin after coupling. Each synthesis cycle is minimally described by a three minute deprotection (25% piperidine/N-methyl-pyrrolidone (NMP)), a 15 minute deprotection, five one minute NMP washes, a 60 minute coupling cycle, five NMP washes and a ninhydrin test. For N-terminal modification, an N-terminal modifying reagent is substituted for an FMOC-D-amino acid and coupled to a 700 mg portion of the fully assembled peptide-resin by the above protocol. The peptide is removed from the resin by treatment with trifluoroacetic acid (TFA) (82.5%), water (5%), thioanisole (5%), phenol (5%), ethanedithiol (2.5%) for two hours followed by precipitation of the peptide in cold ether. The solid is pelleted by centrifugation (2400 rpm×10 min.), and the ether decanted. The solid is resuspended in ether, pelleted and decanted a second time. The solid is dissolved in 10% acetic acid and lyophilized to dryness. For structural analysis, 60 mg of the solid is dissolved in 25% acetonitrile (ACN)/0.1% TFA and applied to a C18 reversed phase high performance liquid chromatography (HPLC) column.

Alternatively, β-amyloid modulators comprising D-amino acids can be prepared on an Advanced ChemTech Model 396 multiple peptide synthesizer using an automated protocol established by the manufacturer for 0.025 mmole scale synthesis. Double couplings are performed on all cycles using 2-(1H-benzotriazol-1-yl)-1,1,3,3-tetramethyluronium hexafluorophosphate (HBTU)/N,N-diisopropylethylamine (DIEA)/HOBt/FMOC-D-amino acid in four-fold excess for 30 minutes followed by DIC/HOBt/FMOC-D-amino acid in four-fold excess for 45 minutes. The peptide is deprotected and removed from the resin by treatment with TFA/water (95%/5%) for three hours and precipitated with ether as described above. The pellet is resuspended in 10% acetic acid and lyophilized. The material is purified by a preparative HPLC using 15%–40% acetonitrile over 80 minutes on a Vydac C18 column (21×250 mm).

Various N-terminally modified β-amyloid modulator compounds can be synthesized using standard methods. Fully-protected resin-bound peptides are prepared as described above on Wang resin to eventually afford carboxyl terminal peptide acids. Small portions of each peptide resin (e.g., 13–20 μmoles) are aliquoted into the wells of the reaction block of an Advanced ChemTech Model 396 Multiple Peptide Synthesizer. The N-terminal FMOC protecting group of each sample is removed in the standard manner with 25% piperidine in NMP followed by extensive washing with NMP. The unprotected N-terminal α-amino group of each peptide-resin sample can be modified using one of the following methods:

Method A, coupling of modifying reagents containing free carboxylic acid groups: The modifying reagent (five equivalents) is predissolved in NMP, DMSO or a mixture of these two solvents. HOBT and DIC (five equivalents of each reagent) are added to the dissolved modifier and the resulting solution is added to one equivalent of free-amino peptide-resin. Coupling is allowed to proceed overnight, followed by washing. If a ninhydrin test on a small sample of peptide-resin shows that coupling is not complete, the coupling is repeated using 1-hydroxy-7-azabenzotriazole (HOAt) in place of HOBt.

Method B, coupling of modifying reagents obtained in preactivated forms: The modifying reagent (five equivalents) is predissolved in NMP, DMSO or a mixture of these two solvents and added to one equivalent of peptide-resin. Diisopropylethylamine (DIEA; six equivalents) is added to the suspension of activated modifier and peptide-resin. Coupling is allowed to proceed overnight, followed by washing. If a ninhydrin test on a small sample of peptide-resin shows that coupling is not complete, the coupling is repeated.

After the second coupling (if required) the N-terminally modified peptide-resins are dried at reduced pressure and cleaved from the resin with removal of side-chain protecting groups as described above. Analytical reversed-phase HPLC is used to confirm that a major product is present in the resulting crude peptides, which are purified using Millipore Sep-Pak cartridges or preparative reverse-phase HPLC. Mass spectrometry or high-field nuclear magnetic resonance spectrometry is used to confirm the presence of the desired compound in the product.

EXAMPLE 2

β-Amyloid Aggregation Assays

The ability of β-amyloid modulator compounds to modulate (e.g., inhibit or promote) the aggregation of natural β-AP when combined with the natural β-AP can be examined in one or both of the aggregation assays described below. Natural β-AP (β-$AP_{1-40}$) for use in the aggregation assays is commercially available from Bachem (Torrance, Calif.).

A. Nucleation Assay

The nucleation assay is employed to determine the ability of test compounds to alter (e.g. inhibit) the early events in formation of β-AP fibers from monomeric β-AP. Characteristic of a nucleated polymerization mechanism, a lag time is observed prior to nucleation, after which the peptide rapidly forms fibers as reflected in a linear rise in turbidity. The time delay before polymerization of β-AP monomer can be quantified as well as the extent of formation of insoluble fiber by light scattering (turbidity). Polymerization reaches equilibrium when the maximum turbidity reaches a plateau. The turbidity of a solution of natural β-AP in the absence or presence of various concentrations of a β-amyloid modulator compound is determined by measuring the apparent absorbance of the solution at 405 nm ($A_{405\ nm}$) over time. The threshold of sensitivity for the measurement of turbidity is in the range of 15–20 μM β-AP. A decrease in turbidity over time in the presence of the modulator, as compared to the turbidity in the absence of the modulator, indicates that the modulator inhibits formation of β-AP fibers from monomeric β-AP. This assay can be performed using stirring or shaking to accelerate polymerization, thereby increasing the speed of the assay. Moreover the assay can be adapted to a 96-well plate format to screen multiple compounds.

To perform the nucleation assay, first $Aβ_{1-40}$ peptide is dissolved in HFIP (1,1,1,3,3,3-Hexafluoro-2-propanol; Aldrich 10,522-8) at a concentration of 2 mg peptide/ml and incubated at room temperature for 30 min. HFIP-solubilized peptide is sonicated in a waterbath sonicator for 5 min at highest setting, then evaporated to dryness under a stream of argon. The peptide film is resuspended in anhydrous dimethylsulfoxide (DMSO) at a concentration of 6.9 mg/ml (25× concentration), sonicated for 5 min as before, then filtered through a 0.2 micron nylon syringe filter (VWR cat. No. 28196-050). Test compounds are dissolved in DMSO at a 100× concentration. Four volumes of 25× $Aβ_{1-40}$ peptide in DMSO are combined with one volume of test compound in DMSO in a glass vial, and mixed to produce a 1:1 molar ratio of Aβ peptide to test compound. For different molar ratios, test compounds are diluted with DMSO prior to addition to $Aβ_{1-40}$, in order to keep the final DMSO and $Aβ_{1-40}$ concentrations constant. Control samples do not contain the test compound. Ten microliters of the mixture is then added to the bottom of a well of a Corning Costar ultra low binding 96-well plate (Corning Costar, Cambridge Mass.; cat. No. 2500). Ninety microliters of water is added to the well, the plate is shaken on a rotary shaken at a constant speed at room temperature for 30 seconds, an additional 100 μl of 2× PTL buffer (20 mM $NaH_2PO_4$, 300 mM NaCl, pH 7.4) is added to the well, the plate is reshaken for 30 seconds and a baseline (t=0) turbidity reading is taken by measuring the apparent absorbance at 405 nm using a Bio-Rad Model 450 Microplate Reader. The plate is then returned to the shaker and shaken continuously for 5 hours. Turbidity readings are taken at 15 minute intervals.

β-amyloid aggregation in the absence of any modulators results in enhanced turbidity of the natural β-AP solution (i.e., an increase in the apparent absorbance at 405 nm over time). Accordingly, a solution including an effective inhibitory modulator compound exhibits reduced turbidity as compared to the control sample without the modulator compound (i.e., less apparent absorbance at 405 nm over time as compared to the control sample).

Alternative to use of turbidity to quantitate β-amyloid aggregation, fluorescence of thioflavin T (Th-T) also can be used to quantitate β-amyloid aggregation in the nucleation assay (use of Th-T fluorescence for quantitating β-amyloid aggregation is described further below for the seeded extension assay).

B. Seeded Extension Assay

The seeded extension assay can be employed to measure the rate of Aβ fiber formed in a solution of Aβ monomer following addition of polymeric Aβ fiber "seed". The ability of test compounds to prevent further deposition of monomeric Aβ to previously deposited amyloid is determined using a direct indicator of β-sheet formation using fluorescence. In contrast with the nucleation assay, the addition of seed provides immediate nucleation and continued growth of preformed fibrils without the need for continuous mixing, and thus results in the absence of a lag time before polymerization starts. Since this assay uses static polymerization conditions, the activity of positive compounds in the nucleation assay can be confirmed in this second assay under different conditions and with an additional probe of amyloid structure.

In the seeded extension assay, monomeric $A\beta_{1-40}$ is incubated in the presence of a "seed" nucleus (approximately ten mole percent of Aβ that has been previously allowed to polymerize under controlled static conditions). Samples of the solution are then diluted in thioflavin T (Th-T). The polymer-specific association of Th-T with Aβ produces a fluorescent complex that allows the measurement of the extent of fibril formation (Levine, H. (1993) *Protein Science* 2:404–410). In particular, association of Th-T with aggregated β-AP, but not monomeric or loosely associated β-AP, gives rise to a new excitation (ex) maximum at 450 nm and an enhanced emission (em) at 482 nm, compared to the 385 nm (ex) and 445 nm (em) for the free dye. Small aliquots of the polymerization mixture contain sufficient fibril to be mixed with Th-T to allow the monitoring of the reaction mixture by repeated sampling. A linear growth curve is observed in the presence of excess monomer. The formation of thioflavin T responsive β-sheet fibrils parallels the increase in turbidity observed using the nucleation assay.

A solution of Aβ monomer for use in the seeded extension assay is prepared by dissolving an appropriate quantity of $A\beta_{1-40}$ peptide in 1/25 volume of dimethysulfoxide (DMSO), followed by water to 1/2 volume and 1/2 volume 2× PBS (10× PBS: NaCl 137 mM, KCl 2.7 mM $Na_2HPO_4 \cdot 7H_2O$ 4.3 mM, $KH_2PO_4$ 1.4 mM pH 7.2) to a final concentration of 200 μM. To prepare the stock seed, 1 ml of the Aβ monomer preparation, is incubated for approximately 8 days at 37° C. and sheared sequentially through an 18, 23, 26 and 30 gauge needle 25, 25, 50, and 100 times respectively. 2 μl samples of the sheared material is taken for fluorescence measurements after every 50 passes through the 30 gauge needle until the fluorescence units (FU) plateau (approx. 100–150×). Test compounds are prepared by dissolving an appropriate amount of test compound in 1× PBS to a final concentration of 1 mM (10× stock). If insoluble, the compound is dissolved in 1/10 volume of DMSO and diluted in 1× PBS to 1 mM. A further 1/10 dilution is also prepared to test each candidate at both 100 μM and 10 μM.

To perform the seeded extension assay, each sample is set up with 50 μl of 200 μM monomer, 125 FU sheared seed (a variable quantity dependent on the batch of seed, routinely 3–6 μl) and 10 μl of 10× modulator solution. The sample volume is then adjusted to a final volume of 100 μl with 1× PBS. Two concentrations of each modulator typically are tested: 100 μM and 10 μM, equivalent to a 1:1 and a 1:10 molar ratio of monomer to modulator. The controls include an unseeded reaction to confirm that the fresh monomer contains no seed, and a seeded reaction in the absence of any modulators, as a reference to compare against candidate modulators. The assay is incubated at 37° C. for 6 h, taking 2 μl samples hourly for fluorescence measurements. To measure fluorescence, a 2 μl sample of Aβ is added to 400 μl of Thioflavin-T solution (50 mM Potassium Phosphate 10 mM Thioflavin-T pH 7.5). The samples are vortexed and the fluorescence is read in a 0.5 ml micro quartz cuvette at EX 450 nm and EM 482 nm (Hitachi 4500 Fluorimeter).

β-amyloid aggregation results in enhanced emission of Thioflavin-T. Accordingly, samples including an effective inhibitory modulator compound exhibit reduced emission as compared to control samples without the modulator compound.

EXAMPLE 3

Analysis of β-Amyloid Modulator Compounds Comprising D-Amino Acids

In this example, D-amino acid-containing modulator compounds designed based upon the Aβ aggregation core domain $A\beta_{17-21}$ were prepared and tested for their ability to inhibit aggregation of natural β-amyloid peptide using aggregations assays as described in Example 2. Abbreviations used in this example are: h- (free amino terminus), -oh (free carboxylic acid terminus), $-nh_2$ (amide terminus), CA (cholyl, the acyl portion of cholic acid), PEA (phenethylamide) and d (D-amino acid). Compounds in which the amino acid residues are in parentheses and preceded by "d" indicate that all amino acid residues are D-amino acids. For example, d(LVFFA) indicates D-Leu-D-Val-D-Phe-D-Phe-D-Ala.

The results from a first series of experiments, using N-terminally-cholyl modified compounds, are summarized below in Table I. The modulator compounds were evaluated in nucleation assays utilizing 5 μM $A\beta_{1-40}$ and either 2 or 5 μM test compound (i.e., 40 or 100 mole % inhibitor). The change in lag time (ΔLag) is presented as the ratio of the lag time observed in the presence of the test compound (at either 2 or 5 μM) to the lag time of the control.

TABLE I

| | N-Term. | | C-Term. | ΔLag | |
|---|---|---|---|---|---|
| Ref. # | Mod. | Peptide | Mod. | 2 μM | 5 μM |
| PPI-382 | CA- | LVFFA (SEQ ID NO: 3) | $-nh_2$ | >10 | >12 |
| PPI-399 | CA- | LVYFA (SEQ ID NO: 32) | -cooh | 3.0 | 6 |
| PPI-454 | CA- | d(AFFVL) | -cooh | 4.0 | >12 |
| PPI-457 | CA- | d(LVFFA) | $-nh_2$ | ND* | >10 |
| PPI-458 | CA- | d(LVFF) | $-nh_2$ | >10 | 6 |

*ND = not done

The results shown in Table I demonstrate that all D-amino acid-containing modulators designed based on the $A\beta_{17-21}$ region are effective inhibitors of Aβ aggregation. Effective inhibitors can comprise, for example, all D-amino acid compounds corresponding to the entire $A\beta_{17-21}$ region (e.g., PPI-457), to a smaller portion thereof (e.g., PPI-458, comprising $A\beta_{17-20}$) or to a rearranged sequence thereof (e.g., PPI-454). The carboxy terminus of effective inhibitors can comprise, for example, a free carboxylic acid terminus (e.g., PPI-454) or a C-terminal amide modification (e.g., PPI-457 and PPI-458).

In a second series of experiments using all D-amino acid modulators, a different stock of $A\beta_{1-40}$ was used in the nucleation assays from that used for the experiments shown in Table I. This new stock exhibited some delay in lag time even in absence of inhibitor and therefore the fold increase in lag time in the presence of test inhibitors was lower in these experiments compared to previous experiments. Despite this difference, the ability of a variety of all D-amino acid-containing modulators to inhibit Aβ aggregation was evident compared to the negative control, an all D-alanine containing peptide (PPI-473). The results of this series of experiments, in which test compounds were assayed at 2, 3, 4 or 5 μM, are shown below in Table II.

TABLE II

| Ref. # | N-Term. Mod. | Peptide | C-Term. Mod. | ΔLag 2 μM | 3 μM | 4 μM | 5 μM |
|---|---|---|---|---|---|---|---|
| PPI-473 | h- | d(AAAAA) | -nh$_2$ | ND* | 1.0 | 1.0 | 1.0 |
| PPI-368 | CA- | LVFFA (SEQ ID NO: 3) | -oh | ND | 2 | >3.5 | 3.5 |
| | | | | 1.1 | ND | ND | 2.7 |
| | | | | ND | 1.4 | 1.9 | 2.1 |
| | | | | ND | ND | 2.1 | >2.1 |
| | | | | ND | 1.2 | 1.8 | >2.5 |
| PPI-455 | CA- | d(LVYFA) | -oh | 1.8 | 2.0 | 2.3 | >2.7 |
| PPI-458 | CA- | d(LVFF) | -nh$_2$ | 2.1 | 2.5 | 2.1 | 1.1 |
| PPI-462 | CA- | d(LV(IY)FA) | -oh | 2.7 | >2.7 | >2.7 | >2.7 |
| PPI-463 | CA- | d(LVF(IY)A) | -oh | >2.7 | >2.7 | >2.7 | >2.7 |
| PPI-464 | h- | d(LVFFA) | -oh | 1.3 | 1.9 | >2.1 | 1.4 |
| PPI-465 | h- | d(LVFFA) | -nh$_2$ | 1.9 | 3.5 | >3.5 | 2.6 |
| PPI-467 | h- | d(VFF) | -nh$_2$ | 1.2 | 1.4 | 1.0 | 1.1 |
| PPI-471 | h- | d(LVFF) | -nh$_2$ | 2.6 | 2.6 | 2.6 | 2.4 |
| PPI-479 | h- | d(LVFA) | -oh | 1.1 | 0.9 | 1.0 | 1.1 |
| PPI-493 | h- | d(VF) | -PEA | 1.0 | 1.0 | 1.0 | 1.9 |
| PPI-494 | h- | d(LVF) | -PEA | 1.0 | 1.3 | 1.4 | 1.4 |

*ND = not done

The results shown in Table II further demonstrate that all D-amino acid-containing modulators designed based on the Aβ$_{17-21}$ region are effective inhibitors of Aβ aggregation.

EXAMPLE 4
Variation of the N-Terminal Modifying Group on D-Amino Acid-Based Modulator Compounds In this example, a series of modulator compounds were prepared which differed in their N-terminal modifying groups. The ability of the modulator compounds to inhibit aggregation of natural β-amyloid peptide was evaluated using aggregations assays as described in Example 2. Abbreviations used in this example and presentation of the data are the same as described in Example 3. The results for compounds modified with N-terminal modifying groups derived from different bile acids are shown below in Table III. The results for compounds modified with various hydrophobic N-terminal modifying groups are shown below in Table IV. The results for compounds modified with various hydrophobic N-terminal modifying groups are shown below in Table IV. The results for compounds modified with various N-terminal hydroxylated and oxygenated modifying groups are shown below in Table V. Compounds exhibiting a change in lag time (ΔLag) of 1.3 or greater are highlighted in bold.

TABLE III

Modifying Groups Derived from Bile Acids

| Ref. # | N-Term. Mod. | Peptide | C-Term. Mod. | ΔLag 5 μM |
|---|---|---|---|---|
| PPI-424 | Cholyl- | LVFFA (SEQ ID NO: 3) | -oh | >6.0 |
| PPI-425 | Lithocholyl- | LVFFA (SEQ ID NO: 3) | -oh | 1.4 |
| PPI-520 | Hyodeoxycholyl- | LVFFA (SEQ ID NO: 3) | -oh | >2.3 |
| PPI-521 | Chenodeoxycholyl- | LVFFA (SEQ ID NO: 3) | -oh | >2.3 |
| PPI-522 | Ursodeoxycholyl- | LVFFA (SEQ ID NO: 3) | -oh | >2.3 |

TABLE IV

Hydrophobic Modifying Groups

| Ref. # | N-Term. Mod. | Peptide | C-Term. Mod. | ΔLag 5 μM |
|---|---|---|---|---|
| PPI-480 | Phenylacetyl- | d(LVFF) | -nh$_2$ | 1.0 |
| PPI-484 | Diphenylacetyl- | d(LVFF) | -nh$_2$ | 1.3 |
| PPI-485 | Triphenylacetyl- | d(LVFF) | -nh$_2$ | 2.7 |
| PPI-490 | trans-Cinnamoyl- | d(LVFF) | -nh$_2$ | 1.0 |
| PPI-525 | Butanoyl- | d(LVFFA) | -nh$_2$ | 1.0 |
| PPI-526 | Isobutanoyl- | d(LVFFA) | -nh$_2$ | 1.8 |
| PPI-524 | 4-Methylvaleryl- | d(LVFFA) | -nh$_2$ | 1.6 |
| PPI-492 | 1-Adamantanecarbonyl- | d(LVFF) | -nh$_2$ | 1.1 |
| PPI-497 | h- | d(VF) | -PEA | 1.0 |
| PPI-495 | Acetyl- | d(VF) | -PEA | 1.0 |
| PPI-494 | Cholyl- | d(LVF) | -PEA | 1.5 |
| PPI-467 | h- | d(VFF) | -nh$_2$ | 1.0 |
| PPI-502 | h- | d(VFF) | -oh | 1.0 |

TABLE V

Hydroxylated and Oxygenated Modifying Groups

| Ref. # | N-Term. Mod. | Peptide | C-Term. Mod. | ΔLag 5 μM |
|---|---|---|---|---|
| PPI-483 | 3-Hydroxyphenylacetyl- | d(LVFF) | -nh$_2$ | 2.2 |
| PPI-487 | 3,5-Dihydroxy-2-naphthoyl- | d(LVFF) | -nh$_2$ | 2.2 |
| PPI-523 | 3,5-Dihydroxy-2-naphthoyl- | d(LVFFA) | -nh$_2$ | 3.8 |
| PPI-481 | 2-Hydroxyphenylacetyl- | d(LVFF) | -nh$_2$ | 2.0 |
| PPI-486 | 2,4-Dihydroxybenzoyl- | d(LVFF) | -nh$_2$ | 1.2 |
| PPI-489 | Benzoylpropanoyl- | d(LVFF) | -nh$_2$ | 1.2 |
| PPI-491 | 3,4-Dihydroxycinnamoyl- | d(LVFF) | -nh$_2$ | 3.0 |
| PPI-482 (isomer 1) | (±)-Mandelyl- | d(LVFF) | -nh$_2$ | 1.5 |
| PPI-482 (isomer 2) | (±)-Mandelyl- | d(LVFF) | -nh$_2$ | 1.6 |
| PPI-518 | (±)-Mandelyl-(±)-mandelyl- | d(LVFFA) | -nh$_2$ | 1.5 |
| PPI-516 | | Pepstatin A | | 1.6 |
| PPI-537 | 4-Hydroxycinnamoyl- | d(LVFFA) | -nh$_2$ | 1.0 |
| PPI-535 | Glycolyl- | d(LVFFA) | -nh$_2$ | 1.4 |
| PPI-596 | Glycolyl- | d(FFFVL) | -nh$_2$ | 3.6 |

The results shown in Tables III, IV and V demonstrate that a variety of different N-terminal modifying groups can be used in the inhibitory compounds of the invention.

EXAMPLE 5
D-Amino Acid-Based Modulator Compounds Having a Free Amino-Terminus In this example, the necessity for an N-terminal modifying group on the D-amino acid-based modulator compounds was evaluated. Peptides comprised entirely of D-amino acids and having a free amino terminus were prepared and tested for their ability to inhibit aggregation of natural β-amyloid peptide using aggregations assays as described in Example 2. Abbreviations used in this example and presentation of the data are the same as described in Example 3. The results are shown below in Table VI. Compounds exhibiting a change in lag time (ΔLag) of 1.3 or greater are highlighted in bold.

TABLE VI

| Ref. # | N-Term. Mod. | Peptide | C-Term. Mod. | ΔLag 0.5 μM | 1.5 μM | 5.0 μM |
|---|---|---|---|---|---|---|
| PPI-500 | h- | d(AFFVL) | -nh$_2$ | 1.0 | 1.8 | >6.0 |
| PPI-503 | h- | d(LVYFA) | -nh$_2$ | ND | ND | 1.2 |

TABLE VI-continued

| Ref. # | N-Term. Mod. | Peptide | C-Term. Mod. | ΔLag 0.5 μM | 1.5 μM | 5.0 μM |
|---|---|---|---|---|---|---|
| PPI-504 | h- | d(LV(IodoY)FA) | -nh₂ | ND | ND | 2.2 |
| PPI-505 | Acetyl- | d(LVYFA) | -nh₂ | ND | ND | 1.0 |
| PPI-506 | Acetyl- | d(LV(IodoY)FA) | -nh₂ | ND | ND | 1.0 |
| PPI-577 | h- | d(AFFLL) | -nh₂ | 1.0 | 1.3 | >7.5 |
| PPI-578 | h- | d(LFFVL) | -nh₂ | 2.5 | 4.8 | >7.5 |
| PPI-579 | h- | d(FFFVL) | -nh₂ | 1.8 | 6.3 | >7.5 |
| PPI-533 | h- | d(FFFLV) | -nh₂ | 1.5 | 3.8 | >7.5 |
| PPI-589 | h- | d(FFFFL) | -nh₂ | 1.5 | 3.3 | >7.5 |
| PPI-598 | h- | d(AFFFL) | -nh₂ | 1.3 | 2.0 | >6.3 |

*ND = not done

The results shown in Table VI demonstrate that modulators comprising all D-amino acids and having a free amino terminus are effective at inhibiting aggregation of natural β-amyloid peptides (i.e., an N-terminal modifying group is not required for the D-amino acid-containing modulators to effectively inhibit aggregation of natural β-amyloid peptides). A particularly preferred D-amino acid modulator compound having a free amino-terminus is PPI-579, the retro-inverso isomer of Aβ$_{17-21}$ (A$_{21}$→F) with a C-terminal amide.

EXAMPLE 6
Neurotoxicity Assay

The neurotoxicity of natural β-amyloid peptide aggregates, in either the presence or absence of a β-amyloid modulator, can be tested in a cell-based assay using either a rat or human neuronally-derived cell line (PC-12 cells or NT-2 cells, respectively) and the viability indicator 3,(4,4-dimethylthiazol-2-yl)2,5-diphenyl-tetrazolium bromide (MTT). (See e.g., Shearman, M. S. et al. (1994) *Proc. Natl. Acad. Sci. USA* 91:1470–1474; Hansen, M. B. et al. (1989) *J. Immun. Methods* 119:203–210 for a description of similar cell-based viability assays). PC-12 is a rat adrenal pheochromocytoma cell line and is available from the American Type Culture Collection, Rockville, Md. (ATCC CRL 1721). MTT (commercially available from Sigma Chemical Co.) is a chromogenic substrate that is converted from yellow to blue in viable cells, which can be detected spectrophotometrically.

To test the neurotoxicity of natural β-amyloid peptides, stock solutions of fresh Aβ monomers and aged Aβ aggregates are first prepared. Aβ$_{1-40}$ in 100% DMSO is prepared from lyophilized powder and immediately diluted in one half the final volume in H₂O and then one half the final volume in 2× PBS so that a final concentration of 200 μM peptide, 4% DMSO is achieved. Peptide prepared in this way and tested immediately on cells is referred to as "fresh" Aβ monomer. To prepare "aged" Aβ aggregates, peptide solution is placed in a 1.5 ml Eppendorf tube and incubated at 37° C. for eight days to allow fibrils to form. Such "aged" Aβ peptide can be tested directly on cells or frozen at –80° C. The neurotoxicity of fresh monomers and aged aggregates are tested using PC12 and NT2 cells. PC12 cells are routinely cultured in Dulbecco's modified Eagle's medium (DMEM) containing 10% horse serum, 5% fetal calf serum, 4 mM glutamine, and 1% gentamycin. NT2 cells are routinely cultured in OPTI-MEM medium (GIBCO BRL CAT. #31985) supplemented with 10% fetal calf serum, 2 mM glutamine and 1% gentamycin. Cells are plated at 10–15,000 cells per well in 90 μl of fresh medium in a 96-well tissue culture plate 3–4 hours prior to treatment. The fresh or aged Aβ peptide solutions (10 μL) are then diluted 1:10 directly into tissue culture medium so that the final concentration is in the range of 1–10 μM peptide. Cells are incubated in the presence of peptide without a change in media for 48 hours at 37° C. For the final three hours of exposure of the cells to the β-AP preparation, MTT is added to the media to a final concentration of 1 mg/ml and incubation is continued at 37° C. Following the two hour incubation with MTT, the media is removed and the cells are lysed in 100 μL isopropanol/0.4N HCl with agitation. An equal volume of PBS is added to each well and the plates are agitated for an additional 10 minutes. Absorbance of each well at 570 nm is measured using a microtiter plate reader to quantitate viable cell.

Using this assay, the neurotoxicity of aged (5 day or 8 day) Aβ$_{1-40}$ aggregates alone, but not fresh Aβ$_{1-40}$ monomers alone, was confirmed. Experiments demonstrated that incubating the neuronal cells with increasing amounts of fresh Aβ$_{1-40}$ monomers was not significantly toxic to the cells whereas incubating the cells with increasing amounts of 5 day or 8 day Aβ$_{1-40}$ aggregates led to increasing amount of neurotoxicity. The EC$_{50}$ for toxicity of aged Aβ$_{1-40}$ aggregates was 1–2 μM for both the PC12 cells and the NT2 cells.

To determine the effect of a β-amyloid modulator compound on the neurotoxicity of Aβ$_{1-40}$ aggregates, a modulator compound is preincubated with Aβ$_{1-40}$ monomers under standard nucleation assay conditions as described in Example 2 and at particular time intervals post-incubation, aliquots of the β-AP/modulator solution are removed and 1) the turbidity of the solution is assessed as a measure of aggregation and 2) the solution is applied to cultured neuronal cells for 48 hours at which time cell viability is assessed using MTT to determine the neurotoxicity of the solution. Additionally, the ability of β-amyloid modulator compounds to reduce the neurotoxicity of preformed Aβ$_{1-40}$ aggregates can be assayed. In these experiments, Aβ$_{1-40}$ aggregates are preformed by incubation of the monomers in the absence of any modulators. The modulator compound is then incubated with the preformed Aβ$_{1-40}$ aggregates for 24 hours at 37° C., after which time the β-AP/modulator solution is collected and its neurotoxicity evaluated as described above.

EXAMPLE 7
Assay of Modulator Compound Stability in Cerebrospinal Fluid

The stability of a modulator compound in cerebrospinal fluid (CSF) can be assayed in an in vitro assay as follows. A CSF solution is prepared containing 75% Rhesus monkey CSF (commercially available from Northern Biomedical Research), 23% sterile phosphate buffered saline and 2% dimethylsulfoxide (v/v) (Aldrich Chemical Co., Catalog No. 27,685-5). Test modulator compounds are added to the CSF solution to a final concentration of 40 μM or 15 μM. All sample handling is carried out in a laminar flow hood and test solutions are maintained at 37° C. during the assay. After 24 hours, enzymatic activity in the solutions is quenched by adding acetonitrile to produce a final concentration of 25% (v/v). Samples (at the 0 time point and the 24 hour time point) are analyzed at room temperature using reverse-phase HPLC. A microbore column is used to maximize sensitivity. The parameters for analytical HPLC are as follows:

Solvent System
   A: 0.1% Trifluoroacetic acid (TFA) in water (v/v)
   B: 0.085% TFA/Acetonitrile, 1% H₂O (v/v)
Injection and Gradient
   Inject: 100–250 μL of test sample Run: 10% for B for 5 min., then 10–70% B over 60 min. Chromatographic analysis is performed using a Hewlett Packard 1090 series II HPLC. The column used for separation is a C4, 5 µm, 1×250 mm (Vydac #214TP51). The flow rate is 50 µL/min and the elution profile of the test compounds is monitored at 214, 230, 260 and 280 nm.

The above-described CSF stability assay was used to compare the CSF stability of a L-amino acid-based modulator compound (PPI-368, having the structure cholyl-Leu-Val-Phe-Phe-Ala-OH SEQ ID NO: 34) with an analogous D-amino acid-based peptide acid (PPI-433, having the structure cholyl-D-Leu-D-Val-D-Phe-D-Phe-D-Ala-OH) and an analogous D-amino acid-based peptide amide (PPI-457, having the structure cholyl-D-Leu-D-Val-D-Phe-D-Phe-D-Ala-NH$_2$). The results, summarized in the bar graph shown in FIG. 1, demonstrate that both D-amino acid-based compounds exhibit significantly greater stability in CSF than the L-amino acid-based compound.

EXAMPLE 8

Brain Uptake Assay

Brain uptake of test modulator compounds is measured using the technique of Oldendorf (*Brain Research* (1970) 24:372–376). In this established model, the brain uptake index (BUI) is an estimate of the relative ability of a particular compound to cross the blood-brain barrier, expressed as a percentage of that observed by the freely diffusable reference, water. Radiolabelled compounds are administered to a test animal as a rapid bolus (200 µl) into the left common carotid artery (with the left external carotid artery ligated). The animal is sacrificed 15 seconds later and the amount of radioactivity within the ipsilateral forebrain is determined. The BUI is computed using the equation below:

$$\text{Brain Uptake Index } (BUI) = \frac{(\text{dpm of test compound in brain})/(\text{dpm of water in brain})}{(\text{dpm of test compound in injectate})/(\text{dpm of water in injectate})}$$

The above-described assay was used to measure the brain uptake of four cholyl-modified modulator compounds: PPI-382 (having the structure cholyl-Leu-Val-Phe-Phe-Ala-NH$_2$) (SEQ ID NO: 33), PPI-457 (having the structure cholyl-D-Leu-D-Val-D-Phe-D-Phe-D-Ala-NH$_2$), PPI-458 (having the structure cholyl-D-Leu-D-Val-D-Phe-D-Phe-NH$_2$) and PPI-494 (having the structure cholyl-D-Leu-D-Val-D-Phe-phenethylamide). Radiolabel was introduced into the test compounds by using $^{14}$C-labelled cholic acid for modification. The vehicle used for the test compounds was 50 mM cyclodextrin in 75% phosphate buffered saline. Water was used as the freely diffusable reference, sucrose was used as a negative control and cholic acid was used as a control for the diffusability of the modifying group. The results are summarized below in Table VII.

TABLE VII

| Compound | Brain Uptake Index (± SEM) |
| --- | --- |
| Water | 100 |
| Sucrose | 0.78 ± 0.05 |
| Cholic Acid | 1.02 ± 0.09 |
| PPI-382 | 1.79 ± 0.04 |
| PPI-457 | 3.09 ± 0.34 |
| PPI-458 | 4.25 ± 0.49 |
| PPI-494 | 4.78 ± 0.36 |

The results indicate that the D-amino acid-based compounds (PPI-457, PPI-458 and PPI-494) exhibited greater brain uptake than the L-amino acid-based compound (PPI-382). An acetyl-modified D-amino acid based compound (PPI-472, having the structure acetyl-D-Leu-D-Val-D-Phe-D-Phe-NH$_2$) exhibited a similar brain uptake index as PPI-458 and PPI-494 (i.e., about 4.5).

EXAMPLE 9

Analysis of Additional Compounds

Additional compounds were tested using the methods described above. The results are summarized in the following tables.

TABLE VIII

| Ref. # | N-Term. Mod. | Peptide | C-Term. Mod. | ΔLag 5 µM |
| --- | --- | --- | --- | --- |
| PPI-523 | 3,5-Dihydroxy-2-Napthoyl- | d(LVFFA) | -nh$_2$ | 2.1 |
| PPI-548 | 3,7-Dihydroxy-2-naphthoyl- | d(LVFFA) | -nh$_2$ | 2.5 |
| PPI-558 | 4-Hydroxybenzoyl- | d(LVFFA) | -nh$_2$ | 2.0 |
| PPI-559 | 4-Hydroxyphenylacetyl- | d(LVFFA) | -nh$_2$ | 3.5 |

TABLE IX

| Ref. # | N-Term. Mod. | Peptide | C-Term. Mod. | ΔLag 5 µM |
| --- | --- | --- | --- | --- |
| PPI-457 | Cholyl- | d(LVFFA) | -nh$_2$ | >6 |
| PPI-483 | 3-Hydroxyphenylacetyl- | d(LVFF) | -nh$_2$ | 2.9 |
| PPI-494 | Cholyl- | d(LVF) | Phenethylamide | 1.3 |
| PPI-501 | Ac- | d(LVFFA) | -nh$_2$ | 1.4 |
| PPI-520 | Hyodeoxycholyl- | (LVFFA) | -oh | 1.5 |
| PPI-521 | Chenodeoxycholyl- | (LVFFA) | -oh | 3.6 |
| PPI-522 | Ursodeoxycholyl- | (LVFFA) | -oh | 1.2 |
| PPI-532 | 2,4-Dihydroxybenzoyl- | d(LVFFA) | -nh$_2$ | 1.7 |
| PPI-535 | Glycolyl- | d(LVFFA) | -nh$_2$ | 1.3 |
| PPI-536 | 2-Hydroxycinnamoyl- | d(LVFFA) | -nh$_2$ | 1.4 |
| PPI-537 | 4-Hydroxycinnamoyl- | d(LVFFA) | -nh$_2$ | 1.6 |
| PPI-538 | 3-Hydroxycinnamoyl- | d(LVFFA) | -nh$_2$ | 2.0 |
| PPI-539 | 5-Hydantoinacetyl- | d(LVFFA) | -nh$_2$ | 2.4 |
| PPI-543 | 3,4-Dihydroxycinnamoyl- | d(LVFFA) | -nh$_2$ | 1.6 |
| PPI-546 | 3-Formylbenzoyl- | d(LVFFA) | -nh$_2$ | 1.9 |
| PPI-554 | 2-Formylphenoxyacetyl- | d(LVFFA) | -nh$_2$ | 2.6 |
| PPI-555 | 4-Hydroxy-3-methoxy-cinnamoyl- | d(LVFFA) | -nh$_2$ | 1.7 |
| PPI-568 | 3,5-Dihydroxy-2-naphthoyl- | d(AFFVL) | -nh$_2$ | >6 |
| PPI-569 | 3,4-Dihydroxycinnamoyl- | d(AFFVL) | -nh$_2$ | 2.6 |
| PPI-584 | (±)-Mandelyl- | d(AFFVL) | -nh$_2$ | 4.8 |
| PPI-587 | 4-Hydroxycinnamoyl- | d(AFFVL) | -nh$_2$ | 3.7 |
| PPI-592 | Glycolyl- | d(AFFLL) | -nh$_2$ | 1.8 |
| PPI-593 | 3,4-Dihydroxycinnamoyl- | d(LFFVL) | -nh$_2$ | 2.0 |
| PPI-596 | Glycolyl- | d(FFFVL) | -nh$_2$ | 3.6 |
| PPI-599 | DL-3-(4-Hydroxyphenyl)Lactyl- | d(LVFFA) | -nh$_2$ | 1.4 |
| PPI-607 | D-3-Phenyllactyl- | d(AFFVL) | -nh$_2$ | 3.1 |
| PPI-608 | L-3-Phenyllactyl- | d(AFFVL) | -nh$_2$ | >6 |
| PPI-610 | 3-(2-Hydroxyphenyl)propionyl- | d(AFFVL) | -nh$_2$ | 4.5 |
| PPI-611 | 4-(2-Hydroxyphenyl)propionyl- | d(AFFVL) | -nh$_2$ | 3.2 |
| PPI-612 | D-3-Phenyllactyl- | d(FFVL) | -nh$_2$ | 2.1 |
| PPI-615 | 3-(2-Hydroxyphenyl)propionyl- | d(FFVL) | -nh$_2$ | 2.0 |
| PPI-616 | 3-(4-Hydroxyphenyl)propionyl- | d(FFVL) | -nh$_2$ | 1.5 |
| PPI-619 | Hydrocinnamoyl- | d(FFVL) | -oh | 2.0 |
| PPI-629 | 4-Hydroxybenzoyl- | d(AFFVL) | -nh$_2$ | 2.9 |
| PPI-635 | D-3-Phenyllactyl- | d(FFFVL) | -nh$_2$ | 2.5 |
| PPI-636 | Hydrocinnamoyl- | d(FFFVL) | -nh$_2$ | 1.7 |
| PPI-643 | 4-Hydroxybenzoyl- | d(LFFFL) | -nh$_2$ | 2.2 |
| PPI-644 | Ac- | d(LFFFL) | -nh$_2$ | 2.1 |
| PPI-648 | 3,7-Dihydroxy-2-naphthoyl- | d(LFFVL) | -nh$_2$ | 3.1 |
| PPI-649 | 4-Hydroxyphenylacetyl- | d(LFFVL) | -nh$_2$ | 5.1 |
| PPI-650 | 3,7-Dihydroxy-2-naphthoyl- | d(FFFVL) | -nh$_2$ | 2.2 |
| PPI-651 | 4-Hydroxyphenylacetyl- | d(FFFVL) | -nh$_2$ | 2.1 |

TABLE X

| Ref. # | N-Term. Mod. | Peptide | C-Term. Mod. | ΔLag 5 μM |
|---|---|---|---|---|
| PPI-504 | H- | d(LV[iodo-Y]FA) | -nh$_2$ | 1.4 |
| PPI-533 | H- | d(FFFLV) | -nh$_2$ | >6 |
| PPI-571 | H- | d(A[homoPhe][homoPhe]VL) | -nh$_2$ | >6 |
| PPI-577 | H- | d(AFFLL) | -nh$_2$ | >6 |
| PPI-578 | H- | d(LFFVL) | -nh$_2$ | 3.2 |
| PPI-579 | H- | d(FFFVL) | -nh$_2$ | >6 |
| PPI-589 | H- | d(FFFFL) | -nh$_2$ | >6 |
| PPI-598 | H- | d(AFFFL) | -nh$_2$ | >6 |
| PPI-602 | H- | d(FFVL) | -nh$_2$ | 1.6 |
| PPI-638 | H- | d(LFFFL) | -nh$_2$ | >6 |
| PPI-655 | H- | d(LVFFL) | -nh$_2$ | >6 |

TABLE XI

| Ref. # | N-Term Mod. | Peptide | C-Term Mod. | μM | ΔLag | % Inhib. Plateau |
|---|---|---|---|---|---|---|
| PPI-656 | H- | d(LVFFF) | -nh$_2$ | 5 | >2.5 | 60 |
|  |  |  |  | 1.5 | 6 | 60 |
|  |  |  |  | 0.5 | 2.3 | 0 |
| PPI-657 | H- | d(LVFFV) | -nh$_2$ | 5 | >10 | 100 |
|  |  |  |  | 1.5 | 4 | 42 |
|  |  |  |  | 0.5 | 1.7 | 0 |
| PPI-664 | 3,7-Dihidroxy-2-naphthol- | d(Pal-FFVL) | -nh$_2$ | 5 | 2 | 28 |
|  |  |  |  | 1.5 | 0 | 19 |
|  |  |  |  | 0.5 | 0 | 0 |
| PPI-665 | 4-Hydroxybenzoyl- | d(Pal-FFVL) | -nh$_2$ | 5 | 2 | 0 |
|  |  |  |  | 1.5 | 2 | 0 |
|  |  |  |  | 0.5 | 1.5 | 0 |
| PPI-730 | 3-Pyridylacetyl- | d(AFFVL) | -nh$_2$ | 5 | 2 | 50 |
| PPI-732 | Isonicotinoyl- | d(AFFVL) | -nh$_2$ | 5 | <2 | 0 |
| PPI-733 | H-Glycyl- | d(FFVL) | -nh$_2$ | 5 | 0 | 25 |
| PPI-734 | H-Glycyl- | d(AFFVL) | -nh$_2$ | 5 | >10 | 100 |
| PPI-741 | 4-Pyridylacetyl- | d(AFFVL) | -nh$_2$ | 5 | ND | 0 |
|  |  |  |  | 2.5 | 2.0 | ND |
| PPI-746 | 4-Quinoline-carboxyl- | d(AFFVL) | -nh$_2$ | 5 | 2 | 0 |
| PPI-748 | 1-Isoquinoline-carboxyl- | d(AFFVL) | -nh$_2$ | 5 | <3 | 0 |
| PPI-749 | 3-Isoquinoline-carboxyl- | d(AFFVL)) | -nh$_2$ | 5 | 3 | 28 |
| PPI-772 | 4-Hydroxybenzoyl- | d(LVFYA) | -nh$_2$ | 5 | 2 | 0 |
| PPI-774 | 4-Hydroxybenzoyl- | d(LVYFA) | -nh$_2$ | 5 | 1 | 0 |
| PPI-775 | 4-Hydroxybenzoyl- | d(LVYYA) | -nh$_2$ | 5 | 1 | 0 |

Pal = pyridylalaline
ND = not done

EXAMPLE 10
Brain Uptake of PPI-558

A brain uptake assay was used to measure the brain uptake of tritium-labelled PPI-558 ($^3$H-PPI-558) (having the structure: 4-Hydroxybenzoyl-D-Leu-D-Val-D-Phe-D-Phe-D-Ala-NH$_2$). The tritium-labelled PPI-558 was prepared via the synthesis of the iodo-phenylalanine analog of PPI-558, followed by reductive tritiolysis of the label and HPLC purification. Such labeling can be performed as a commercial service by, for example, Amersham or New England Nuclear.

Male Sprague-Dawley rats (259–280 g) received a single subcutaneous injection in the nape of the neck (4.6 mg/kg at 1 ml/kg=4.6 mg/ml in 100% Sesame Oil). At various time points post administration (2, 8 and 24 hours; n=4/time point), the animals were anesthetized. Trunk blood was taken to determine plasma levels of the parent compound and the left side of the brain was perfused with 1 ml of saline over 30 seconds via the left sommon carotid artery. The brain was rapidly removed and the left forebrain (perfused) was subjected to capillary depletion. This technique, plus perfusion, removes blood and brain capillaries from the parenchyma and thus allows the accurate determination of the levels of PPI-558 that have traversed the blood brain barrier into the parenchyma.

Figure 2:
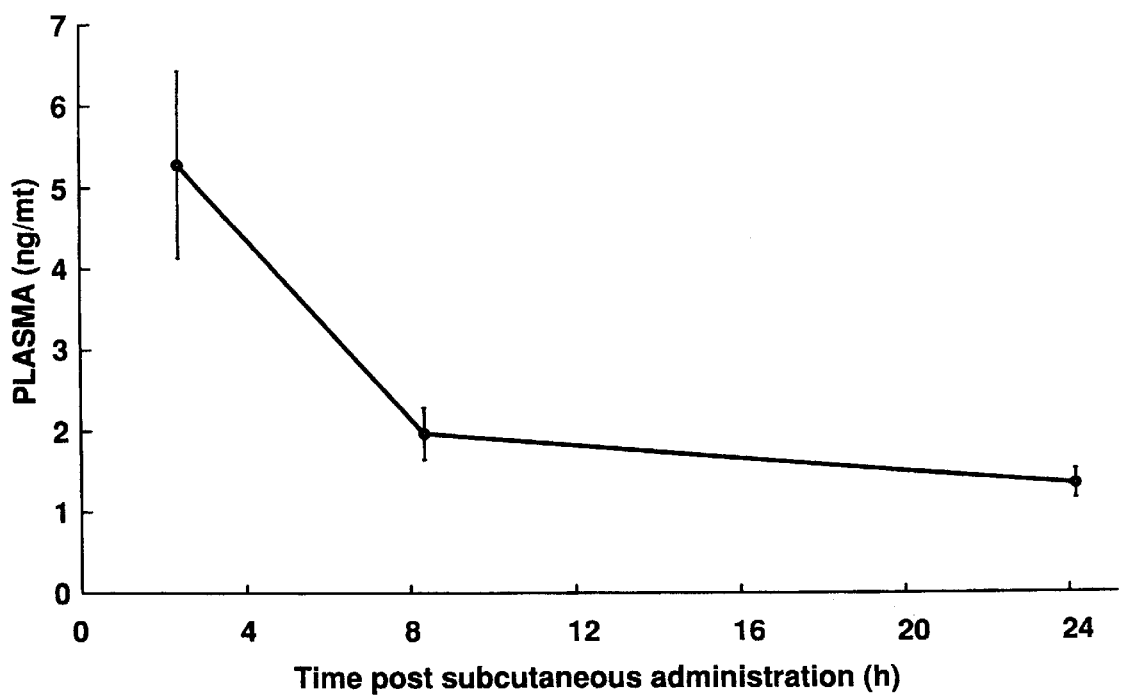
FIG. 2 is a graph depicting the levels of PPI-558 in the plasma at 2, 8 and 24 hours following a single subcutaneous injection of PPI-558 (4.6 mg/kg) to male Sprague-Dawley rats. Each point is the mean±standard error for four rats.
Figure 3:
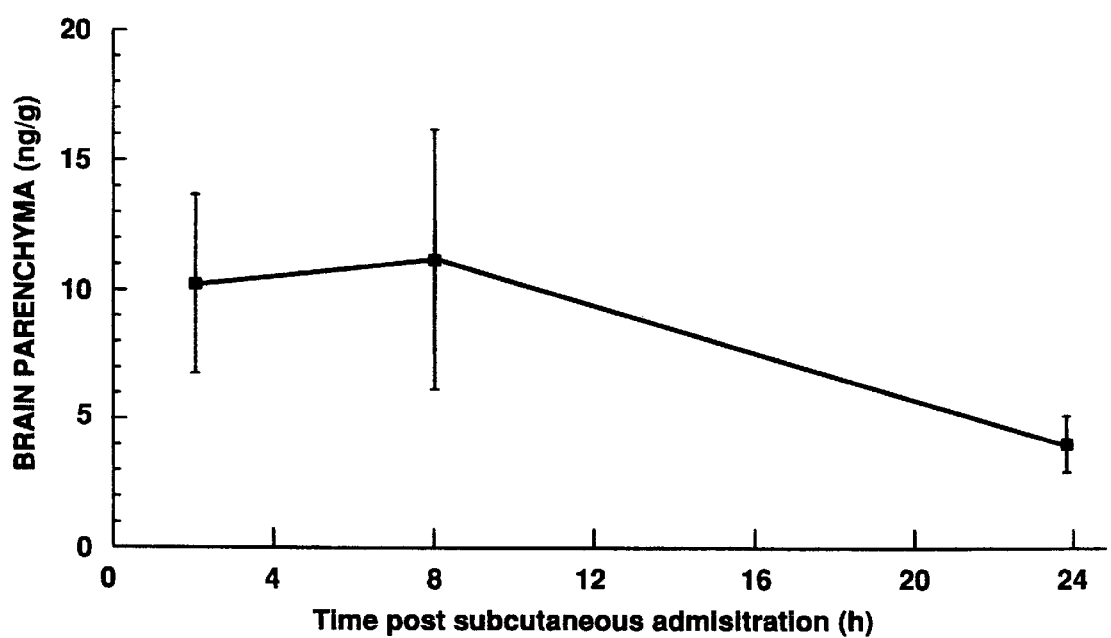
FIG. 3 is a graph depicting the levels of PPI-558 in the brain parenchyma (void of blood and brain capillaries) at 2, 8 and 24 hours following a single subcutaneous injection of PPI-558 (4.6 mg/kg) to male Sprague-Dawley rats. Each point is the mean±standard error for four rats.

The concentration of the parent compound ($^3$H-PPI-558) (mean±sem) was determined in the plasma (results shown in the graph of FIG. 2) and in the brain parenchyma (results shown in the graph of FIG. 3).

Figure 4:
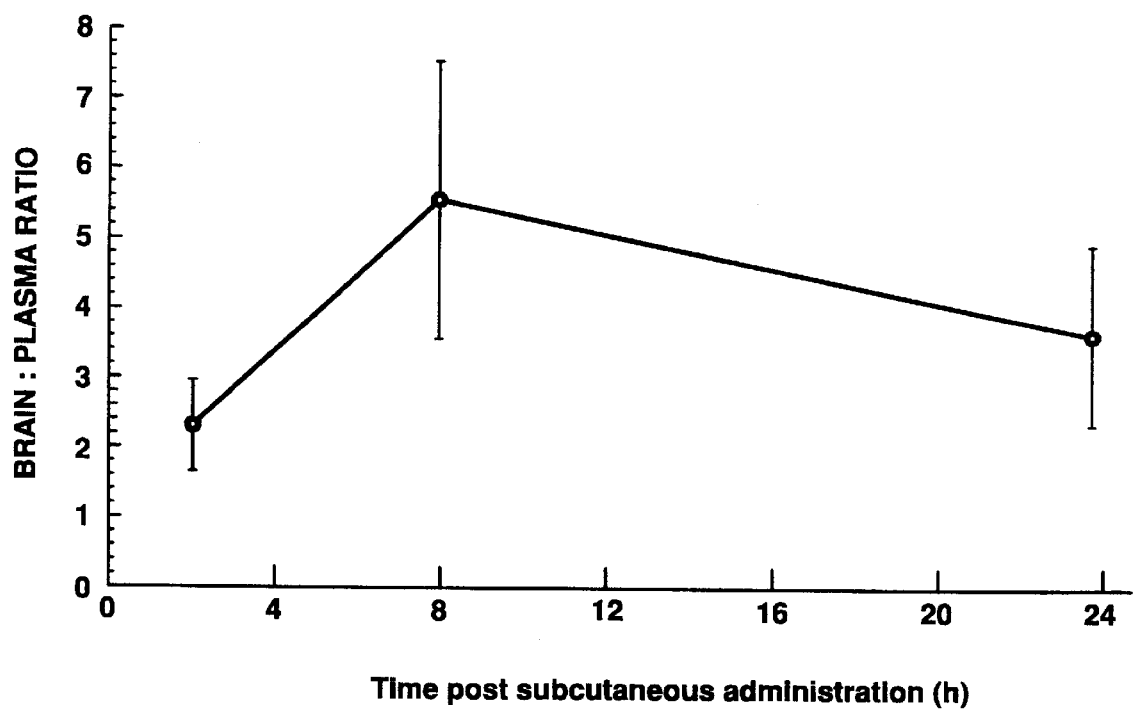
FIG. 4 is a graph depicting the ratio of brain parenchyma versus plasma levels of PPI-558 at 2, 8 and 24 hours following a single subcutaneous injection of PPI-558 (4.6 mg/kg) to male Sprague-Dawley rats. Each point is the mean±standard error for four rats.

As highlighted in FIG. 4 (which shows the ratio of brain versus plasma levels of PPI-558), the data shows that following a single subcutaneous injection of 4.6 mg/kg of PPI-558, there was 7.4 nM in the plasma at 2 hours with brain parenchymal levels of almost twice that (14.1 nM). Similar profiles were seen at 8 and 24 hours post administration.

The data confirms the possibility that brain clearance is slower than that at plasma (seen in i.v. bolus studies) and that by maintaining plasma levels, brain levels can be maintained.

EXAMPLE 11
Safety Profile for PPI-558

PPI-558 at 3 and 30 mg/kg (in 100% Sesame Oil) was administered to female Sprague-Dawley rats as a single subcutaneous injection each day for 14 days. On day 15, animals were sacrificed 1 hour post administration. Via Mass Spectroscopy plasma levels 4.9±1.1 ng/ml and 21.8±2.0 ng/ml were observed for the 3 and 30 mg/kg groups, respectively. No overt toxicity was observed. Blood chemistry, hematology was within normal ranges and histological analysis of various organs revealed no problems.

Forming part of this disclosure is the appended Sequence Listing, the contents of which are summarize in the Table below.

| SEQ ID NO: | Aβ Amino Acids | Peptide Sequence |
|---|---|---|
| 1 | 43 amino acids | Aβ$_{1-43}$ |
| 2 | 103 amino acids | APP C-terminus |
| 3 | Aβ$_{17-21}$ | LVFFA |
| 4 | Aβ$_{17-21}$ retro-inverso isomer | d(AFFVL) |
| 5 | Aβ$_{17-21}$ (V$_{18}$→L) retro-inverso isomer | d(AFFLL) |
| 6 | Aβ$_{17-21}$ (A$_{21}$→L) retro-inverso isomer | d(LFFVL) |
| 7 | Aβ$_{17-21}$ (A$_{21}$→F) retro-inverso isomer | d(FFFVL) |
| 8 | Aβ$_{17-20}$ | LVFF |
| 9 | Aβ$_{17-20}$ inverso isomer | d(LVFF) |
| 10 | Aβ$_{17-19}$ inverso isomer (C-term. mod.) | d(LVF)phenethyl-amide |
| 11 | Aβ$_{17-20}$ (F$_{19}$→Y) inverso isomer | d(LVYF) |
| 12 | Aβ$_{17-26}$ (F$_{19}$→IodoY) inverso isomer | d(LV(IodoY)F) |
| 13 | Aβ$_{17-20}$ (F$_{20}$→Y) inverso isomer | d(LVFY) |
| 14 | Aβ$_{17-20}$ (F$_{20}$→IodoY) inverso isomer | d(LVF(IodoY)) |
| 15 | Aβ$_{17-20}$ (F$_{20}$→A) inverso isomer | d(LVFA) |
| 16 | Aβ$_{17-21}$ inverso isomer | d(LVFFA) |
| 17 | Aβ$_{17-21}$ (L$_{17}$→A; A$_{21}$→L) inverso isomer | d(AVFFL) |
| 18 | Aβ$_{17-21}$ (F$_{19}$→Y) inverso isomer | d(LVYFA) |
| 19 | Aβ$_{17-21}$ (F$_{19}$→IodoY) inverso isomer | d(LV(IodoY)FA) |
| 20 | Aβ$_{17-21}$ (F$_{20}$→Y) inverso isomer | d(LVFYA) |
| 21 | Aβ$_{17-21}$ (F$_{20}$→IodoY) inverso isomer | d(LVF(IodoY)A) |
| 22 | Aβ$_{17-20}$ retro-inverso isomer | d(FFVL) |
| 23 | Aβ$_{18-21}$ retro-inverso isomer | d(AFFV) |
| 24 | Aβ$_{17-21}$ (L$_{17}$→V; V$_{18}$→L; A$_{21}$→F) retro-inverso isomer | d(FFFLV) |
| 25 | Aβ$_{17-21}$ (V$_{18}$→F; A$_{21}$→F) retro-inverso isomer | d(FFFFL) |
| 26 | Aβ$_{17-21}$ (V$_{18}$→F) retro-inverso isomer | d(AFFFL) |
| 27 | Aβ$_{17-21}$ (A$_{21}$→F) | d(LVFFF) |
| 28 | Aβ$_{17-21}$ (A$_{21}$→V) | d(LVFFV) |
| 29 | Aβ$_{17-21}$ (F$_{19}$→Y, F$_{20}$→Y) | d(LVYYA) |
| 30 | Aβ$_{17-21}$ (V$_{18}$→F, A$_{21}$→L) | d(LFFFL) |
| 31 | N/A | DDIIL-Adp |
| 32 | Aβ$_{17-21}$ (F$_{19}$→Y) | LVYFA |
| 33 | Aβ$_{17-21}$ | cholyl-LVFFA-amide |
| 34 | Aβ$_{17-21}$ | cholyl-LVFFA-OH |

Equivalents

Those skilled in the art will recognize, or be able to ascertain using no more than routine experimentation, many equivalents to the specific embodiments of the invention described herein. Such equivalents are intended to be encompassed by the following claims.

We claim:
1. A compound having the structure:

A-(Xaa)-B wherein (Xaa) is a peptidic structure selected from the group consisting of D-Leu-D-Val-D-Phe-D-Phe, D-Leu-D-Val-D-Phe-phenethylamide, D-Leu-D-Val-D-Tyr-D-Phe, D-Leu-D-Val-D-IodoTyr-D-Phe, D-Leu-D-Val-D-Phe-D-Tyr, D-Leu-D-Val-D-Phe-D-IodoTyr, D-Leu-D-Val-D-Phe-D-Ala, D-Leu-D-Val-D-Phe-D-Phe-D-Ala, D-Ala-D-Val-D-Phe-D-Phe-D-Leu, D-Leu-D-Val-D-Tyr-D-Phe-D-Ala, D-Leu-D-Val-D-IodoTyr-D-Phe-D-Ala, D-Leu-D-Val-D-Phe-D-Tyr-D-Ala, D-Leu-D-Val-D-Phe-D-IodoTyr-D-Ala, D-Phe-D-Phe-D-Val-D-Leu, D-Ala-D-Phe-D-Phe-D-Val, D-Ala-D-Phe-D-Phe-D-Val-D-Leu, D-Ala-D-Phe-D-Phe-D-Leu-D-Leu, D-Leu-D-Phe-D-Phe-D-Val-D-Leu, D-Phe-D-Phe-D-Phe-D-Val-D-Leu, D-Phe-D-Phe-D-Phe-D-Leu-D-Val, D-Phe-D-Phe-D-Phe-D-Phe-D-Leu and D-Ala-D-Phe-D-Phe-D-Phe-D-Leu;

A is an amino-terminal modifying group selected from the group consisting of phenylacetyl, diphenylacetyl, triphenylacetyl, butanoyl, isobutanoyl, hexanoyl, propionyl, 3-hydroxybutanoyl, 4-hydroxybutanoyl, 3-hydroxypropionoyl, 2,4-dihydroxybutyroyl, 1-Adamantanecarbonyl, 4-methylvaleryl, 2-hydroxyphenylacetyl, 3-hydroxyphenylacetyl, 4-hydroxyphenylacetyl, 3,5-dihydroxy-2-naphthoyl, 3,7-dihydroxy-2-naphthoyl, 2-hydroxycinnamoyl, 3-hydroxycinnamoyl, 4-hydroxycinnamoyl, hydrocinnamoyl, 4-formylcinnamoyl, 3-hydroxy-4-methoxycinnamoyl, 4-hydroxy-3-methoxycinnamoyl, 2-carboxycinnamoyl, 3,4,-dihydroxyhydrocinnamoyl, 3,4-dihydroxycinnamoyl, trans-Cinnamoyl, (±)-mandelyl, (±)-mandelyl-(±)-mandelyl, glycolyl, 3-formylbenzoyl, 4-formylbenzoyl, 2-formylphenoxyacetyl, 8-formyl-1-naphthoyl, 4-(hydroxymethyl)benzoyl, 3-hydroxybenzoyl, 4-hydroxybenzoyl, 5-hydantoinacetyl, L-hydroorotyl, 2,4-dihydroxybenzoyl, 3-benzoylpropanoyl, (±)-2,4-dihydroxy-3,3-dimethylbutanoyl, DL-3-(4-hydroxyphenyl)lactyl, 3-(2-hydroxyphenyl)propionyl, 4-(2-hydroxyphenyl)propionyl, D-3-phenyllactyl, 3-(4-hydroxyphenyl)propionyl, L-3-phenyllactyl, 3-pyridylacetyl, 4-pyridylacetyl, isonicotinoyl, 4-quinolinecarboxyl, 1-isoquinolinecarboxyl and 3-isoquinolinecarboxyl;

and B is a carboxy-terminal modifying group selected from the group consisting of an amide group, an alkyl amide group, an aryl amide group and a hydroxy group.

2. A compound having the structure:

A-(Xaa)-B wherein (Xaa) is a peptidic structure selected from the group consisting of D-Leu-D-Val-D-Phe-D-Phe, D-Leu-D-Val-D-Phe-phenethylamide, D-Leu-D-Val-D-Tyr-D-Phe, D-Leu-D-Val-D-IodoTyr-D-Phe, D-Leu-D-Val-D-Phe-D-Tyr, D-Leu-D-Val-D-Phe-D-IodoTyr, D-Leu-D-Val-D-Phe-D-Ala, D-Ala-D-Val-D-Phe-D-Phe-D-Leu, D-Leu-D-Val-D-Tyr-D-Phe-D-Ala, D-Leu-D-Val-D-IodoTyr-D-Phe-D-Ala, D-Leu-D-Val-D-Phe-D-Tyr-D-Ala, D-Leu-D-Val-D-Phe-D-IodoTyr-D-Ala, D-Phe-D-Phe-D-Val-D-Leu, D-Ala-D-Phe-D-Phe-D-Val, D-Ala-D-Phe-D-Phe-D-Val-D-Leu, D-Ala-D-Phe-D-Phe-D-Leu-D-Leu, D-Leu-D-Phe-D-Phe-D-Val-D-Leu, D-Phe-D-Phe-D-Phe-D-Val-D-Leu, D-Phe-D-Phe-D-Phe-D-Leu-D-Val, D-Phe-D-Phe-D-Phe-D-Phe-D-Leu and D-Ala-D-Phe-D-Phe-D-Phe-D-Leu;

A is an amino-terminal modifying group selected from the group consisting of cholyl, lithocholyl, hyodeoxycholyl, chenodeoxycholyl and ursodeoxycholyl; and B is a carboxy-terminal modifying group selected from the group consisting of an amide group, an alkyl amide group, an aryl amide group and a hydroxy group.

3. The compound of claim 2, wherein A is selected from the group consisting of lithocholyl, hyodeoxycholyl, chenodeoxycholyl and ursodeoxycholyl.

4. A compound having the structure: 3,5-Dihydroxy-2-Naphthoyl-(D-leucine-D-valine-D-phenylalanine-D-phenylalanine-D-alanine)-NH$_2$.

5. A compound having the structure: 3,7-Dihydroxy-2-Napthtpoyl-(D-leucine-D-valine-D-phenylalanine-D-phenylalanine-D-alanine)-NH$_2$.

6. A compound having the structure: 4-Hydroxybenzoyl-(D-leucine-D-valine-D-phenylalanine-D-phenylalanine-D-alanine)-NH$_2$.

7. A compound having the structure: 4-Hydroxyphenylacetyl-(D-leucine-D-valine-D-phenylalanine-D-phenylalanine-D-alanine)-NH$_2$.

8. A compound having a structure selected from the group consisting of:

Diphenylacetyl -D-leucine-D-valine-D-phenylalanine-D-phenylalanine-NH$_2$;

Triphenylacetyl-D-leucine-D-valine-D-phenylalanine-D-phenylalanine-NH$_2$;

Isobutanoyl-D-leucine-D-valine-D-phenylalanine-D-phenylalanine-D-phenylalanine-NH$_2$;

4-Methylvaleryl-D-leucine-D-valine-D-phenylalanine-D-phenylalanine-D-phenylalanine-NH$_2$;

3-Hydroxyphenylacetyl-D-leucine-D-valine-D-phenylalanine-D-phenylalanine-NH$_2$;

3,5-Dihydroxy-2-naphthoyl-D-leucine-D-valine-D-phenylalanine-D-phenylalanine-NH$_2$;

3,5-Dihydroxy-2-naphthoyl-D-leucine-D-valine-D-phenylalanine-D-phenylalanine-D-alanine-NH$_2$;

2-Hydroxyphenylacetyl-D-leucine-D-valine-D-phenylalanine-D-phenylalanine-NH$_2$;

3,4-Dihydroxycinnamoyl-D-leucine-D-valine-D-phenylalanine-D-phenylalanine-NH$_2$;

(±)-Mandelyl-D-leucine-D-valine-D-phenylalanine-D-phenylalanine-NH$_2$;

(±)-Mandelyl-(±)-Mandelyl-D-leucine-D-valine-D-phenylalanine-D-phenylalanine-D-alanine-NH$_2$;

Glycolyl-D-leucine-D-valine-D-phenylalanine-D-phenylalanine-D-alanine-NH$_2$;

Glycolyl-D-phenylalanine-D-phenylalanine-D-phenylalanine-D-valine-D-leucine-NH$_2$;

D-alanine-D-phenylalanine-D-phenylalanine-D-valine-D-leucine-NH$_2$;

D-leucine-D-valine-D-iodotyrosine-D-phenylalanine-D-alanine-NH$_2$;

D-alanine-D-phenylalanine-D-phenylalanine-D-leucine-D-leucine-NH$_2$;

D-leucine-D-phenylalanine-D-phenylalanine-D-valine-D-leucine-NH$_2$;

D-phenylalanine-D-phenylalanine-D-phenylalanine-D-valine-D-leucine-NH$_2$;

D-phenylalanine-D-phenylalanine-D-phenylalanine-D-leucine-D-valine-NH$_2$;

D-phenylalanine-D-phenylalanine-D-phenylalanine-D-phenylalanine-D-leucine-NH$_2$;
D-alanine-D-phenylalanine-D-phenylalanine-D-phenylalanine-D-leucine-NH$_2$;
D-alanine-D-homophenylalanine-D-homophenylalanine-D-valine-D-leucine-NH$_2$;
D-phenylalanine-D-phenylalanine-D-valine-D-leucine-NH$_2$;
D-leucine-D-phenylalanine-D-phenylalanine-D-phenylalanine-D-leucine-NH$_2$;
D-leucine-D-valine-D-phenylalanine-D-phenylalanine-D-leucine-NH$_2$;
D-leucine-D-valine-D-phenylalanine-D-phenylalanine-D-phenylalanine-NH$_2$;
D-leucine-D-valine-D-phenylalanine-D-phenylalanine-D-valine-NH$_2$;
Hyodeoxycholyl-D-leucine-D-valine-D-phenylalanine-D-phenylalanine-D-alanine-NH$_2$;
Chenodeoxycholyl-D-leucine-D-valine-D-phenylalanine-D-phenylalanine-D-alanine-NH$_2$;
Ursodeoxycholyl-D-leucine-D-valine-D-phenylalanine-D-phenylalanine-D-alanine-NH$_2$;
2,4-Dihydroxybenzoyl-D-leucine-D-valine-D-phenylalanine-D-phenylalanine-D-alanine-NH$_2$;
2-Hydroxycinnamoyl-D-leucine-D-valine-D-phenylalanine-D-phenylalanine-D-alanine-NH$_2$;
3-Hydroxycinnamoyl-D-leucine-D-valine-D-phenylalanine-D-phenylalanine-D-alanine-NH$_2$;
4-Hydroxycinnamoyl-D-leucine-D-valine-D-phenylalanine-D-phenylalanine-D-alanine-NH$_2$;
5-Hydantoinacetyl-D-leucine-D-valine-D-phenylalanine-D-phenylalanine-D-alanine-NH$_2$;
3,4-Dihydroxycinnamoyl-D-leucine-D-valine-D-phenylalanine-D-phenylalanine-D-alanine-NH$_2$;
3-Formylbenzoyl-D-leucine-D-valine-D-phenylalanine-D-phenylalanine-D-alanine-NH$_2$;
2-Formylphenoxyacetyl-D-leucine-D-valine-D-phenylalanine-D-phenylalanine-D-alanine-NH$_2$;
4-Hydroxy-3-methoxycinnamoyl-D-leucine-D-valine-D-phenylalanine-D-phenylalanine-D-alanine-NH$_2$;
3,5-Dihydroxy-2-naphthoyl-D-alanine-D-phenylalanine-D-phenylalanine-D-valine-D-leucine-NH$_2$;
3,4-Dihydroxycinnamoyl-D-alanine-D-phenylalanine-D-phenylalanine-D-valine-D-leucine-NH$_2$;
(±)-Mandelyl-D-alanine-D-phenylalanine-D-phenylalanine-D-valine-D-leucine-NH$_2$;
4-Hydroxycinnamoyl-D-alanine-D-phenylalanine-D-phenylalanine-D-valine-D-leucine-NH$_2$;
Glycolyl-D-alanine-D-phenylalanine-D-phenylalanine-D-valine-D-leucine-NH$_2$;
3,4-Dihydroxycinnamoyl-D-leucine-D-phenylalanine-D-phenylalanine-D-valine-D-leucine-NH$_2$;
Glycolyl-D-phenylalanine-D-phenylalanine-D-phenylalanine-D-valine-D-leucine-NH$_2$;
DL-3-(4-Hydroxyphenyl)Lactyl-D-leucine-D-valine-D-phenylalanine-D-phenylalanine-D-alanine-NH$_2$;
D-3-Phenyllactyl-D-alanine-D-phenylalanine-D-phenylalanine-D-valine-D-leucine-NH$_2$;
L-3-Phenyllactyl-D-alanine-D-phenylalanine-D-phenylalanine-D-valine-D-leucine-NH$_2$;
3-(2-Hydroxyphenyl)propionyl-D-alanine-D-phenylalanine-D-phenylalanine-D-valine-D-leucine-NH$_2$;
4-(2-Hydroxyphenyl)propionyl-D-alanine-D-phenylalanine-D-phenylalanine-D-valine-D-leucine-NH$_2$;
D-3-Phenyllactyl-D-phenylalanine-D-phenylalanine-D-valine-D-leucine-NH$_2$;
3-(2-Hydroxyphenyl)propionyl-D-phenylalanine-D-phenylalanine-D-valine-D-leucine-NH$_2$;
3-(4-Hydroxyphenyl)propionyl-D-phenylalanine-D-phenylalanine-D-valine-D-leucine-NH$_2$;
Hydrocinnamoyl-D-phenylalanine-D-phenylalanine-D-valine-D-leucine-NH$_2$;
4-Hydroxybenzoyl-D-alanine-D-phenylalanine-D-phenylalanine-D-valine-D-leucine-NH$_2$;
D-3-Phenyllactyl-D-phenylalanine-D-phenylalanine-D-phenylalanine-D-valine-D-leucine-NH$_2$;
Hydrocinnamoyl-D-phenylalanine-D-phenylalanine-D-phenylalanine-D-valine-D-leucine-NH$_2$;
4-Hydroxybenzoyl-D-leucine-D-phenylalanine-D-phenylalanine-D-phenylalanine-D-leucine-NH$_2$;
Acetyl-D-leucine-D-phenylalanine-D-phenylalanine-D-phenylalanine-D-leucine-NH$_2$;
3,7-Dihydroxy-2-naphthoyl-D-leucine-D-phenylalanine-D-phenylalanine-D-valine-D-leucine-NH$_2$;
4-Hydroxyphenylacetyl-D-leucine-D-phenylalanine-D-phenylalanine-D-valine-D-leucine-NH$_2$;
3,7-Dihydroxy-2-naphthoyl-D-phenylalanine-D-phenylalanine-D-phenylalanine-D-valine-D-leucine-NH$_2$;
4-Hydroxyphenylacetyl-D-phenylalanine-D-phenylalanine-D-phenylalanine-D-valine-D-leucine-NH$_2$;
3,7-Dihydroxy-2-naphthoyl-D-Pyridylalanine-D-phenylalanine-D-phenylalanine-D-valine-D-leucine-NH$_2$;
4-Hydroxybenzoyl-D-Pyridylalanine-D-phenylalanine-D-phenylalanine-D-valine-D-leucine-NH$_2$;
3-Pyridylacetyl-D-alanine-D-phenylalanine-D-phenylalanine-D-valine-D-leucine-NH$_2$;
Isonicotinoyl-D-alanine-D-phenylalanine-D-phenylalanine-D-valine-D-leucine-NH$_2$;
H-Glycyl-D-phenylalanine-D-phenylalanine-D-valine-D-leucine-NH$_2$;
H-Glycyl-D-alanine-D-phenylalanine-D-phenylalanine-D-valine-D-leucine-NH$_2$;
4-Pyridylacetyl-D-alanine-D-phenylalanine-D-phenylalanine-D-valine-D-leucine-NH$_2$;
4-Quinolinecarboxyl-D-alanine-D-phenylalanine-D-phenylalanine-D-valine-D-leucine-NH$_2$;
1-Isoquinolinecarboxyl-D-alanine-D-phenylalanine-D-phenylalanine-D-valine-D-leucine-NH$_2$;
3-Isoquinolinecarboxyl-D-alanine-D-phenylalanine-D-phenylalanine-D-valine-D-leucine-NH$_2$;
4-Hydroxybenzoyl-D-leucine-D-valine-D-phenylalanine-D-tyrosine-D-alanine-NH$_2$;
4-Hydroxybenzoyl-D-leucine-D-valine-D-tyrosine-D-phenylalanine-D-alanine-NH$_2$; and
4-Hydroxybenzoyl-D-leucine-D-valine-D-tyrosine-D-tyrosine-D-alanine-NH$_2$.

9. A pharmaceutical composition comprising a therapeutically effective amount of a compound of any of claims 1–7, or 8 and a pharmaceutically acceptable carrier.

10. A method for inhibiting aggregation of natural β-amyloid peptides, comprising contacting the natural β-amyloid peptides with the compound of claim 1 such that aggregation of the natural β-amyloid peptides is inhibited.

11. A method for detecting the presence or absence of natural β-amyloid peptides in a biological sample, comprising:

contacting a biological sample with the compound of claim 1, wherein the compound is labeled with a detectable substance; and detecting the compound bound to natural β-amyloid peptides to thereby detect the presence or absence of natural β-amyloid peptides in the biological sample.

12. The method of claim 11, wherein the compound and the biological sample are contacted in vitro.

13. The method of claim 11, wherein the compound is contacted with the biological sample by administering the compound to a subject.

14. The method of claim 11, wherein the compound is labeled with radioactive technetium or radioactive iodine.

15. A method for treating a subject for a disorder associated with β-amyloidosis, comprising:

administering to the subject a therapeutically effective amount of the compound of claim 1 such that the subject is treated for a disorder associated with β-amyloidosis.

16. The method of claim 15, wherein the disorder is Alzheimer's disease.

17. A compound having the structure: D-leucine-D-phenylalanine-D-phenylalanine-D-valine-D-leucine-$NH_2$.

18. A compound having the structure: D-leucine-D-valine-D-phenylalanine-D-phenylalanine-D-leucine-$NH_2$.

19. A compound having the structure: D-leucine-D-valine-D-phenylalanine-D-phenylalanine-D-valine-$NH_2$.

* * * * *